(12) United States Patent
Inouye et al.

(10) Patent No.: US 6,610,533 B1
(45) Date of Patent: Aug. 26, 2003

(54) COLD-SHOCK REGULATORY ELEMENTS, CONSTRUCTS THEREOF, AND METHODS OF USE

(75) Inventors: Masayori Inouye, Piscataway, NJ (US); Nan Wang, Piscataway, NJ (US); Kunitoshi Yamanaka, Highland Park, NJ (US)

(73) Assignee: University of Medicine and Dentistry of New Jersey, NJ (US)

( * ) Notice: Subject to any disclaimer, the term of this patent is extended or adjusted under 35 U.S.C. 154(b) by 0 days.

(21) Appl. No.: 09/516,667

(22) Filed: Mar. 1, 2000

(51) Int. Cl.$^7$ .......................... C12N 15/00; C07H 17/00
(52) U.S. Cl. .................... 435/320.1; 530/23.1
(58) Field of Search ................. 536/23.1; 435/320.1

(56) References Cited

PUBLICATIONS

Blattner et al. 1977; Science 277:1453–1474.*
Wang et al. Mar. 1999; J. Bacteriology 181(5): 1603–1609.*

* cited by examiner

*Primary Examiner*—Karen Cochrane Carlson
(74) *Attorney, Agent, or Firm*—Piper Rudnick LLP

(57) ABSTRACT

A fourth cold shock protein of the *Escherichia coli* CspA family is disclosed, as are the regulatory elements of the 5' UTR of the corresponding gene. The cspI gene is located at 35.2 min on the *E. coli* chromosome map, and CspI shows 70, 70, and 79% identity of CspA, CspB, and CspG, respectively. The 5'-untranslated region of the cspI mRNA consists of 145 bases and causes a negative effect on cspI expression at 37° C. The cspI mRNA was very unstable at 37° C. but was stabilized upon cold shock. The 5' UTR of cspI can enhance the translation of cold shock inducible genes under conditions that elicit a cold shock response in bacteria.

9 Claims, 48 Drawing Sheets

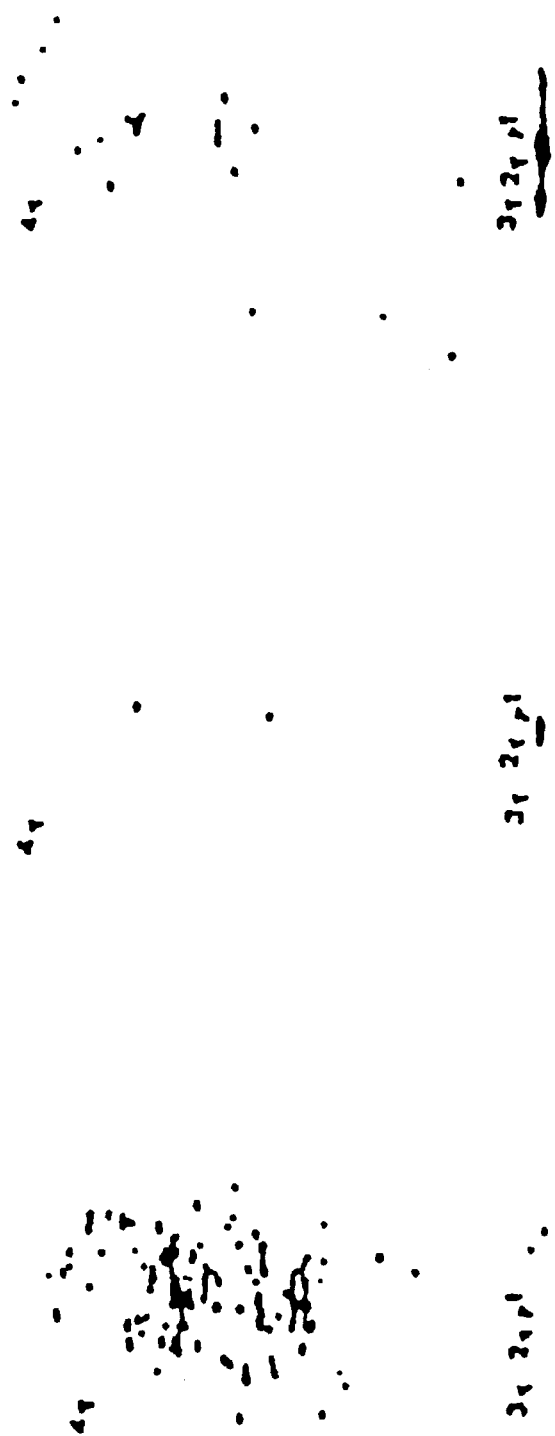

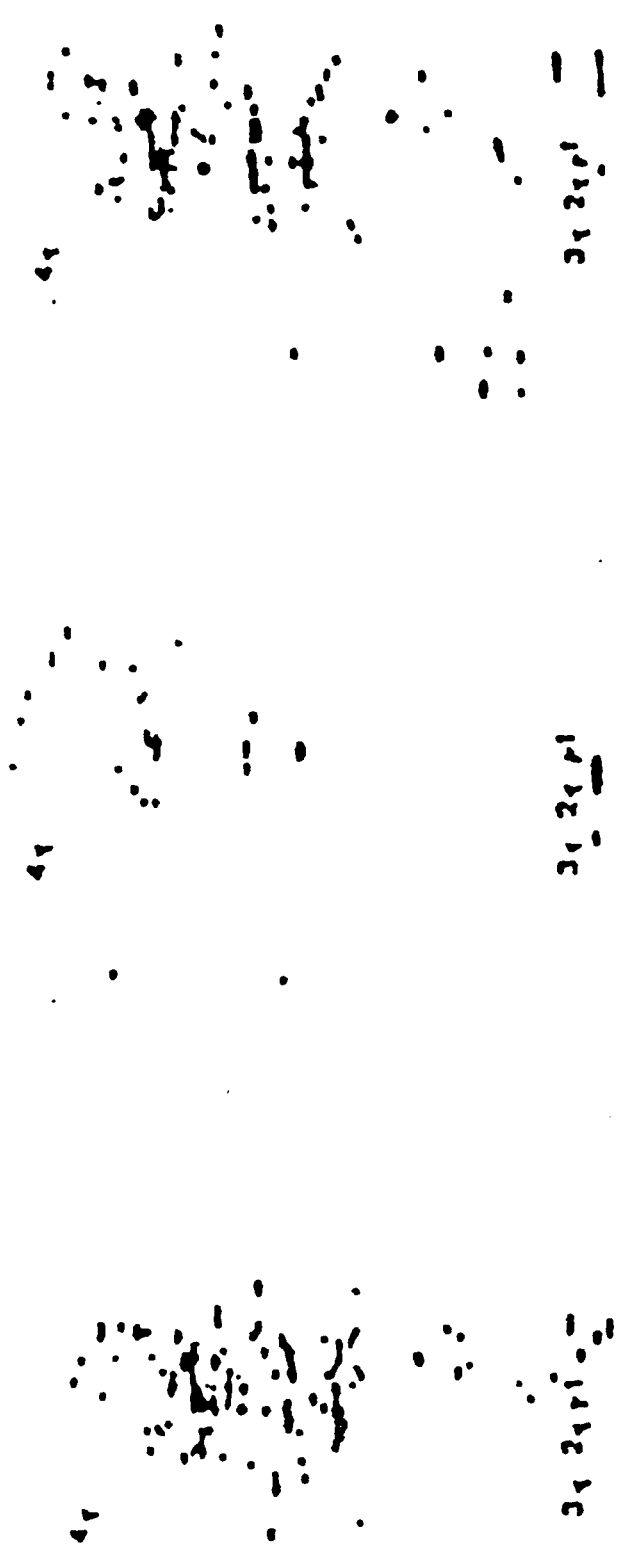

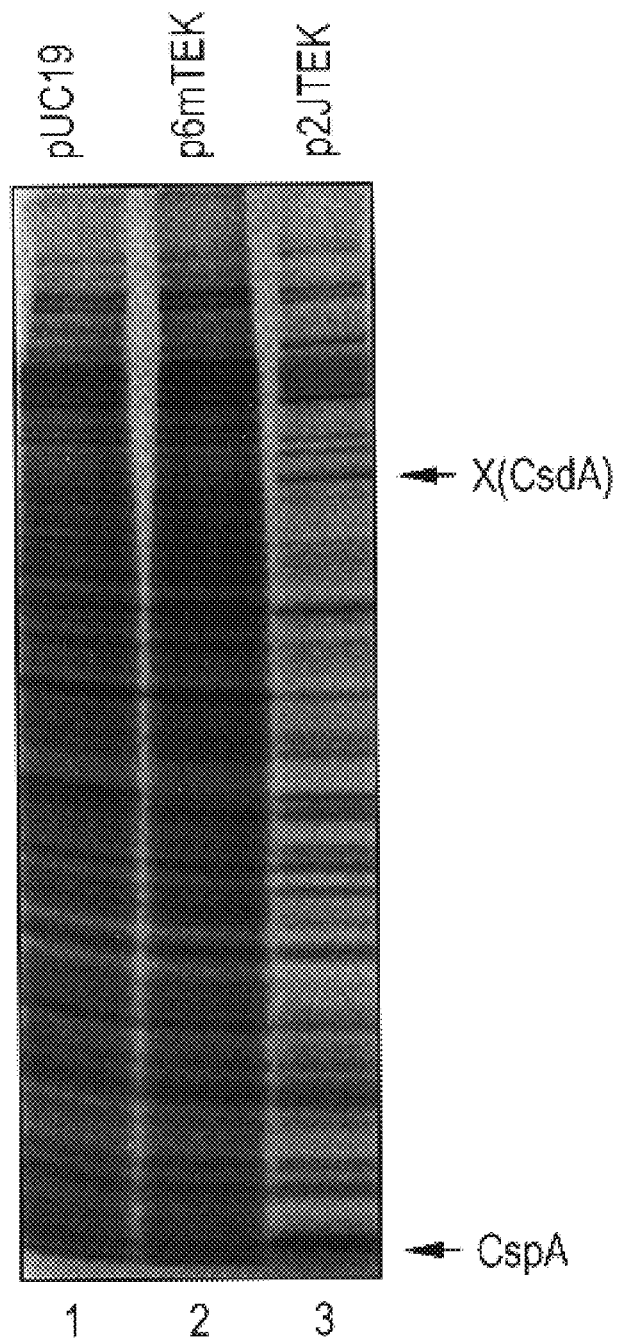

pMM67 pMM022 pMM023 pMM024 pMM025 pMM026

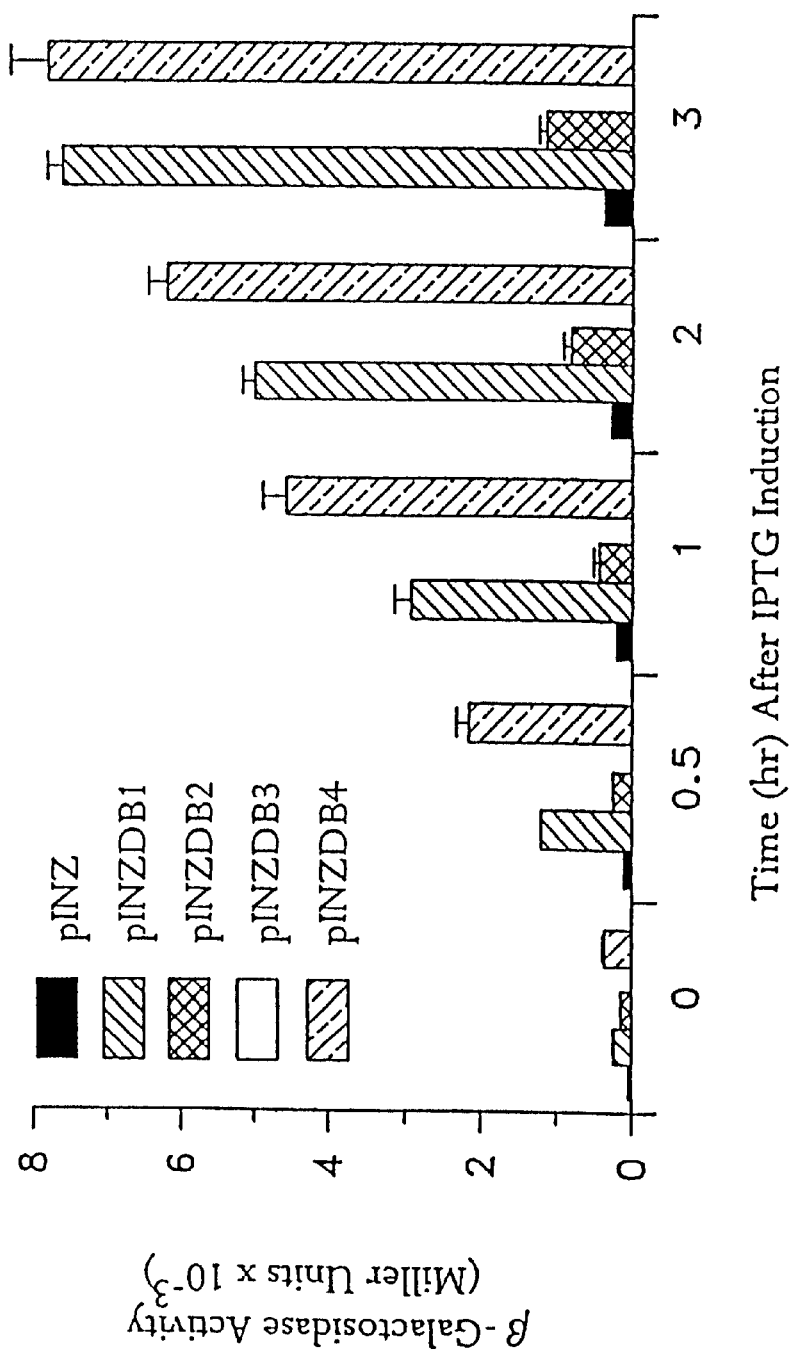

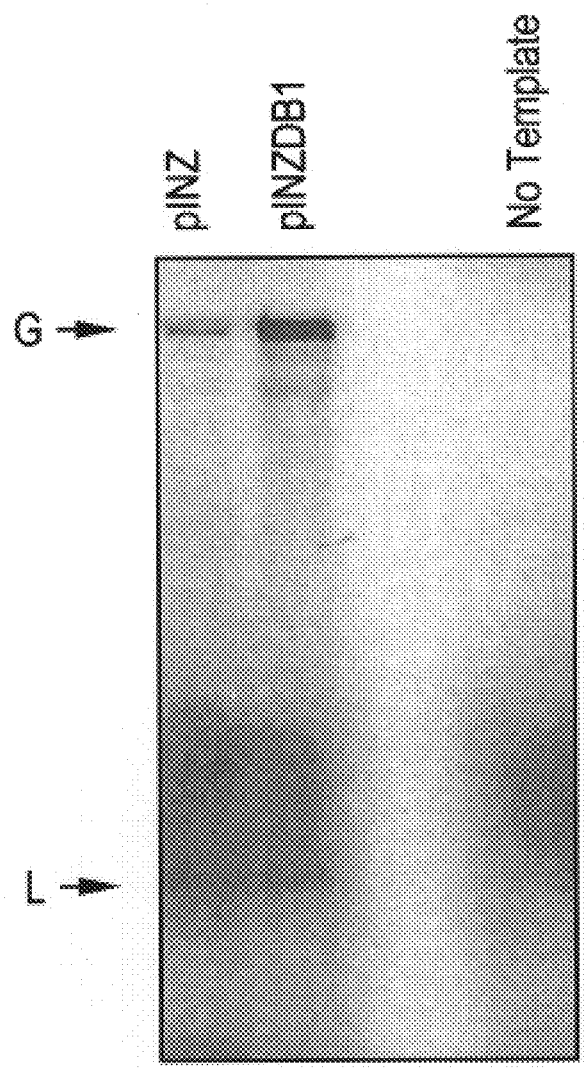

lacZ mRNA

FIG. 21A

```
                                                                        Identity (%)
                                                                         to CspI
CspI  MSNKMTGLVKWFNPEKGFGFITPKDGSKDVFVHFSAIQSNDFKTLTENQEVEFGIENGPKGPAAVHVVAL  100
CspG  .........AD.................................T.L..E.R..N...K...S..Q.QR.....AN..T.  79
CspB  .........AD.........S.V......................NDNYR.F.G.K.T.S..S.A.......AN.IITD  70
CspA  ...G.....I........AD.........................NDGY.S.D.G.K.S.T..S.A.......GN.TS.  70
                      RNP1                    RNP2
```

FIG. 21B

```
             UP                          -35                              -10               +1    Cold Box
cspI  TTTTCTTTACAAAAGTAATCCTTGCTATGGGTGGTTAATCATGGTTAATGCGTTGTT--CT-GGTTTGTTACAAATTTATCTGAAGCAGTCATTGT
cspG  GCCGGACGG.T...A....AAT......TAATC.CAA.T............TG......-AGC.GC-G.C..........AA.G.C.GAC.G.AT.CAA...AG..TA
cspB  GC.GGA.GT.T...A....A.A.......TCATA..T.C..CT........A.......-AT.GC-G.C..........AAGA.C.GACGATAT.C.A...AG..TA
cspA  CA..AAA.ATG....A...........TG......ATCACCC.CCA.TG.G...GC...CACA.CAA-C..........ACGT.C.GAC--.AT-TAA..CAG.GTA cspI  TATAA--TTTTATTATTGTACCTCTTGAGATTTCCTTGTTGGTTT--TCTCTCT---GA-----TA----TTT-T--TT-TT-CGGACCATTC
cspG  CTA...GCAG...C.CA-...-..T.AGGCATT.TCC....-C-T-...GAG.......CCT..A-CAC..AGTAG....C.-G..A..AGTAG....C..G.-A..AAA.C..TG.T
cspB  CTA...GCAG...C.C....C-..GG.G..ATTCAC.TA..CC.TC...GAG..........CAATT.AGTACG.AGTCG...C.G..A.GCAAAC.AT..A
cspA  GTA.GGCAAG.CCCT.C-AAGAGA.TA.CGTTGA.A.CCC.C.TAG.GCACA.TC.TTTAACGCTTCA.AATCTG.AAAGC-AC-----.C.ATA..

SD                  Downstream
      Upstream                     Box
      Sequence
cspI  TGCCCAAGGGCTAATTTCTTCAA--AAGGTAATAAT-TATGTCTAACAAAATGACTGGTTTAGTGAAATGGTTTAAC
cspG  ....G..A....CC------AA..TG...A.G....AA........T.................A............
cspB  ....G..A....TC------A..GTT....A.-GTAGA....A..T..................A............
cspA  ....G..A....AC.C...AA.T.TTA....T.A..CAC.....CGGT................A.C.A........C
```

COLD-SHOCK REGULATORY ELEMENTS, CONSTRUCTS THEREOF, AND METHODS OF USE

STATEMENT OF FEDERALLY-SPONSORED RESEARCH

The research reporting the disclosure of the present application was federally-sponsored by National Institute of Health under Grant Number GM 19430.

BACKGROUND OF THE INVENTION

1. Field of the Invention

The invention relates to the control of bacterial gene expression, especially the regulation of bacterial gene expression under conditions of physiologic stress. More specifically, the invention relates to the regulation of bacterial gene expression under conditions of physiologic stress that induce the cold shock response of a bacterium.

2. Description of the Related Art

The regulation of bacterial gene expression occurs at many levels, including transcriptional control, or control of the synthesis of mRNA from a given gene; translational control, or the regulation of the efficiency by which the mRNA is translated into polypeptide sequence by the ribosome; and mRNA stability, or the efficiency at which a given mRNA population within the cell is degraded and rendered inactive. The control of bacterial gene expression under conditions of physiologic stress that elicit the cold shock response of the bacterium involve regulation at all three of the levels described above.

The response of bacteria to physiologic stress involve the tightly controlled expression of a small number of genes that function to allow the cell to adapt to and multiply under stress conditions. For example, when bacterial cells are exposed to temperatures above the normal physiologic temperature for that organism, a set of genes, designated the heat shock genes, are expressed. This response to elevated temperatures is well known and described in the prior art. Conversely, when bacterial cells are exposed to lower than physiologic temperatures, a different set of genes, designated as cold shock (cs) genes, are expressed. Expression of the cs genes allow the cell to first adapt to the physiologic stress, and subsequently grow under conditions of physiologic stress. This invention relates to the specific processes that regulate the expression of cs genes.

When a culture of *Escherichia coli* is shifted from 37° C. to 15 or 10° C., a number of proteins, called cold-shock proteins, are transiently induced during its growth lag period (Jones et al., 1987; for review, see Thieringer et al., 1998; Yamanaka et al., 1998). cspA, consisting of 70 amino acid residues, has been identified as a major cold-shock protein (Goldstein et al., 1990) and its three-dimensional structure has been determined by both X-ray crystallography (Schindelin et al., 1994) and nuclear magnetic resonance spectroscopy (Newkirk et al., 1994; Feng et al., 1998) to consist of a five-antiparallel β-stranded structure. cspA can bind to single-stranded DNA and RNA without high sequence specificity and has been proposed to function as an RNA chaperone at low temperature (Jiang et al., 1997).

To date, more than 50 proteins homologous to cspA have been identified in a large varieties of prokaryotes. Moreover, a region called cold-shock domain of eukaryotic Y-box protein family, such as human YB-1 and Xenopus FRGY-2, shares more than 40% identity with *E. coli* cspA (for review, see Wolffe et al., 1992), indicating that the cold-shock domain is well conserved throughout evolution. In *E. coli*, nine genes encoding cspA-like proteins, cspA to cspI, have been identified (for review, see Yamanaka et al., 1998). Among them, cspA, cspB and cspG are cold-shock inducible (Goldstein et al., 1990; Lee et al., 1994; Nakashima et al., 1996) and interestingly, cspD is induced during stationary phase and upon nutrition starvation (Yamanaka and Inouye, 1997). It was proposed that the large cspA family of *E. coli* may have a function to respond to different environmental stresses (for review, see Yamanaka et al., 1998).

cspA expression is transiently induced upon cold shock during the growth lag period called acclimation period. This period is considered to be required for cells to adapt to a new environmental condition. Indeed, during the acclimation period proteins involved in translation such as csdA (Jones et al., 1996), RbfA (Jones and Inouye, 1996) and cspA (Goldstein et al., 1990) are specifically produced, which are considered to play important roles in enhancing translation efficiency for non-cold-shock proteins at low temperature (for review, see Yamanaka et al., 1998). Among these cold-shock proteins, cspA has been quite extensively investigated for the mechanism of its cold-shock induction (for review, see Yamanaka et al., 1998). The cspA promoter is highly active at 37° C., even if cspA is hardly detected at this temperature (Fang et al., 1997; Mitta et al., 1997). Even if the cspA promoter was replaced with the lpp promoter, a constitutive promoter for a major outer membrane protein, cspA expression is still cold-shock inducible (Fang et al., 1997), indicating that the cspA induction at low temperature occurs mainly at levels of mRNA stability and its translation. The cspA promoter, however, contains an AT-rich upstream element (UP element) (Ross et al., 1993) immediately upstream of the −35 region (Fang et al., 1997; Goldenberg et al., 1997; Mitta et al., 1997), which is considered to play an important role in efficient transcription initiation at low temperature. It has been demonstrated that the cspA mRNA becomes extremely stable upon cold shock, indicating that the mRNA stability plays a crucial role in cold-shock induction of cspA (Brandi et al., 1996; Goldenberg et al., 1996; Fang et al., 1997).

An important and unique feature of the cspA mRNA is its unusually long 5'-untranslated region (5'-UTR) consisting of 159 bases (Tanabe et al., 1992). This feature is also shared with other Class I cold-shock genes, which are dramatically induced after temperature downshift (for review, see Thieringer et al., 1998), such as cspB (Etchegaray et al., 1996) and cspG (Nakashima et al., 1996). The 5'-UTR is considered to play a crucial role in the cold-shock induction of cspA (Brandi et at., 1996; Jiang et at., 1996; Goldenberg et al., 1996; Bae et al., 1997; Fang et al., 1997; Goldenberg et al., 1997; Mitta et al., 1997).

Furthermore, it was recently shown that the 14-base downstream box (DB) located 12 bases downstream of the rt codon of the cspA mRNA, which is partially complementary to a region called anti-downstream box of 16S rRNA (Sprengart et al., 1996), plays an important role in efficient translation at low temperature (Mitta et al., 1997). This region of the RNA sequence designated as the downstream box (DB) is complementary to bases 1469–1483 within the *E. coli* 16S rRNA (anti-DB sequence). It is speculated that formation of a duplex between the DB and anti-DB of 16S rRNA is responsible for translational enhancement (Sprengart et al., 1996). The DB sequence has also been implicated in the translation of the mRNA, a mRNA that lacks any untranslated region and the SD sequence (Shean and Gottesman, 1992; Powers et al., 1988). Interestingly λc1 translation was enhanced at 42° C. in a temperature sensitive strain in which the amount of ribosomal protein S2 decreased at 42° C. It was proposed that the anti-DB sequence in S2 deficient ribosomes indirectly becomes more accessible to DB, resulting in enhancement of translation initiation of the λc1 mRNA. However, the role of the DB in λc1 translation initiation was disputed by Resch and coworkers (Resch et al., 1996). These authors constructed lacZ translational fusions with the λc1 gene to test the DB function. Since a deletion of 6 bases encompassing a portion of the DB sequence did not reduce the formation of the translation initiation complex, they disputed the existence of DB. Despite these elusive roles of DB (Sprengart and Porter, 1997) we have shown that the presence of a DB sequence in cold-shock mRNAs plays an important role in translation efficiency, and proposed that the DB is involved in the formation of a stable initiation complex at low temperature before the induction of cold-ribosomal factors (Mitta et al., 1997). Thus, cspA expression is regulated in a complex manner at levels of transcription, mRNA stability and translation.

BRIEF DESCRIPTION OF THE FIGURES

FIGS. 6A–6F show the effects of over-production of the 5' untranslated region of the cspA mRNA on the production of other cold-shock proteins and non-cold-shock protein.

FIG. 8 shows the effects of overproduction of the first 25-base sequence of the cspA 5' UTR on CspA production.

(B) β-Galactosidase activity of the cspA-lacZ fusion constructs after cold shock at 15° C. E. coli AR137 cells transformed with pJJG78, pJJG78DB1 or pJJG78DB2 were grown in LB medium, and at mid-log phase ($OD_{600}$=0.4) cultures were shifted from 37° C. to 15° C. β-galactosidase activity was measured before (time 0) and 1, 2 and 3 hr after the shift.

(C) Detection of the cspA-lacZ mRNAs. Total RNA from E. coli AR137 cells carrying pJJG78, pJJG78DB1 or pJJG78DB2 was extracted at the same time points indicated above (FIG. 1C) and used as a template for primer extension.

(D) Complementarity between DB and anti-DB of the pJJG78DB1 (12 matches) and pJJG78 (15 matches) mRNAs.

FIG. 17 shows that a perfectly matching DB enhances translation at 37° C.: (A) pIN-lacZ constructs. The XbaI-SalI fragment from pJJG78 or pJJG78DB2 was inserted into the XbaI-SalI sites of pIN-III to create pINZ and pINZDB1, respectively which then were used to create pINZDB2, pINZDB3 and pINZDB4; mRNA sequences of the pIN-lacZ constructs showing the position of SD, AUG and DB. The lacZ in pJJG78 has a 10-match DB. The perfect match DB located after the 5$^{th}$ codon has 16 residues complementary with the anti-DB.

(B) β-Galactosidase activity of the pINZ-lacZ constructs. Cultures of E. coli AR137 cells transformed with pINZ, pINZDB1, pINZDB2, pINZDB3 and pINZDB4 were grown at 37° C. under the same conditions described in FIG. 1. IPTG (1 mM) was added at mid-log phase to each culture. β-Galactosidase activity was measured before (time 0) and at 0.5, 1, 2 and 3 hr after IPTG addition.

(C) Shows ratio of β-Galactosidase synthesis of pINZDBI and pINZ.

Figure 18A:
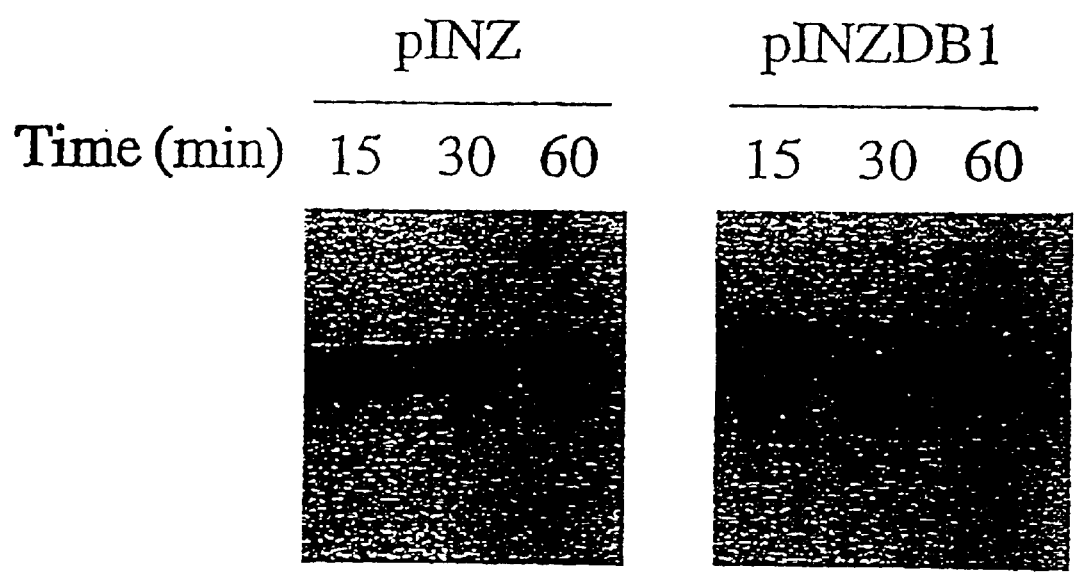

FIGS. 18A and 18E show the rate of β-galactosidase synthesis of the pINZ-lacZ constructs. Cultures of E. coli AR137 cells carrying pINZ or pINZDB1 were grown at 37° C. under the same conditions described above. IPTG (1 mM) was added at mid-log phase to each culture. Rate of β-galactosidase synthesis was measured before (time 0) and 0.5, 1, 2, 3 and 4 hr after IPTG addition. Cells were pulse-labeled with trans-[$^{35}$S]-methionine. Cell extracts from each time point were analyzed by 5% SDS-PAGE and the β-galactosidase synthesis was measured by phosphorimager. The rate of β-galactosidase synthesis from pINZ (filled circle) and pINZDB1 (open circle) is shown at each time point.

Figure 19B:
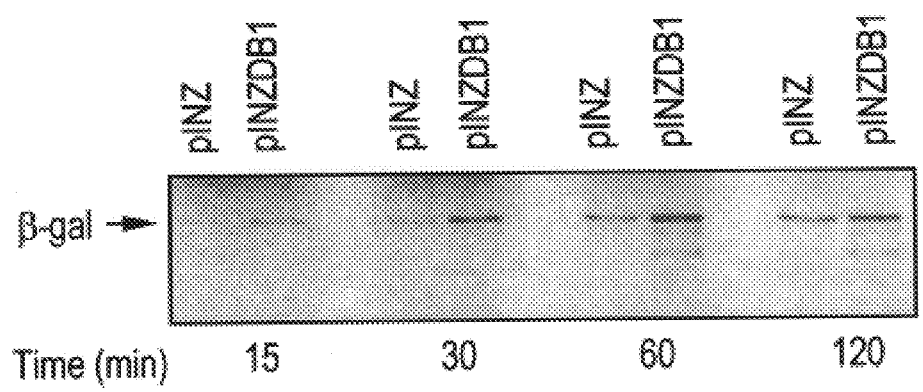
Figure 19C:
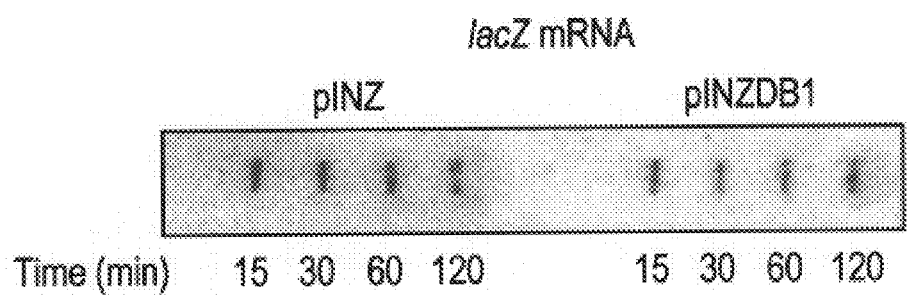

FIGS. 19A–19C show ribosomal fractionation of E. coli JM83 cells transformed with pINZ or pINZDB1. Ribosomal particles were isolated as described by Dammel and Noller, 1995. Cultures of E. coli JM83 cells carrying pINZ or pINZDB1 were grown at 37° C. in LB medium containing 50 mg/ml of ampicillin. At mid-log phase ($OD_{600}$=0.4) 1 mM of IPTG was added to each culture. Chloramphenicol (0.1 mg/ml) was added at 15, 30 and 60 min after IPTG addition. The cell extracts were then layered on top of a 5–40% (w/w) sucrose gradient. The polysomes and ribosomal subunits were separated by centrifugation at 151,000×g for 2.5 hr at 4° C. The polysome profiles were then detected by using a FPLC system. 0.2 ml from each fraction (0.5 ml) were spotted on a Nitrocellulose membrane using the Minifold II Slot-Blot System (Schleicher and Schuell). The lacZ mRNA was detected by hybridization using the [$^{32}$P]-labeled M13-47. Phosphorimager values from the hybridization are plotted at the right side. The pINZ and pINZDB1 mRNAs are shown in closed and open squares, respectively.

Figure 20A:
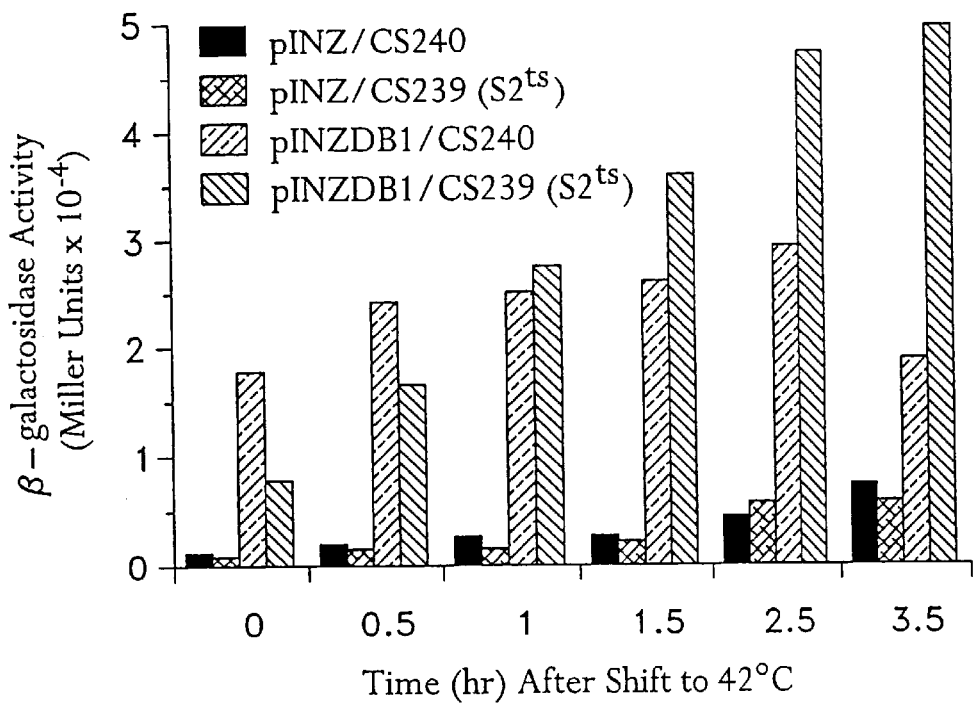
Figure 20B:
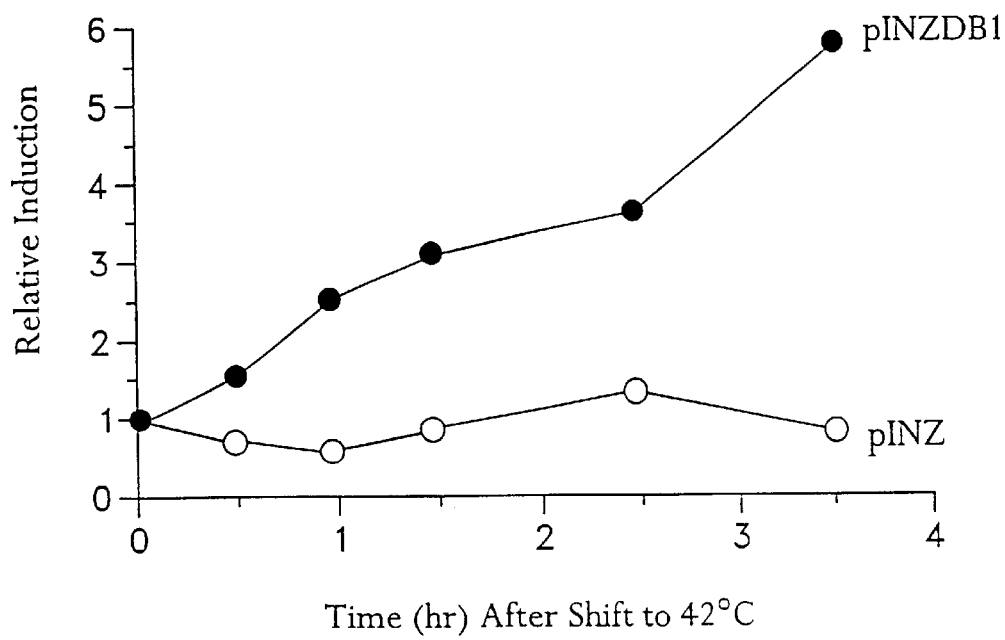

FIG. 20 shows translational enhancement by a perfectly matching DB at 42° C. (A) Estimation of pINZ and pINZDB1 mRNAs. Cultures of E. coli JM83 carrying pINZ or pINZDB1 were grown at 42° C. under the same conditions described in FIG. 4. Total RNA extracted at 15, 30 and 60 min after IPTG (1 mM) addition was used as a template for primer extensions according to the procedure described previously. (B) β-Galactosidase activity of pINZ and pINZDB1 in multi-copy expression system. E. coli JM83 cells transformed with pINZ or pINZDB1 were grown at 42° C. under the same condition described in FIG. 20A. β-Galactosidase activity was measured before (time 0) and 0.5, 1, 1.5, 2 and 2.5 hr after IPTG (1 mM) addition (open circles and squares). Closed circles and squares represent the activities in the absence of IPTG.

FIGS. 21A and 21B are a sequence comparison of four cold-shock-inducible members of the E. coli CspA family.

Figure 22:
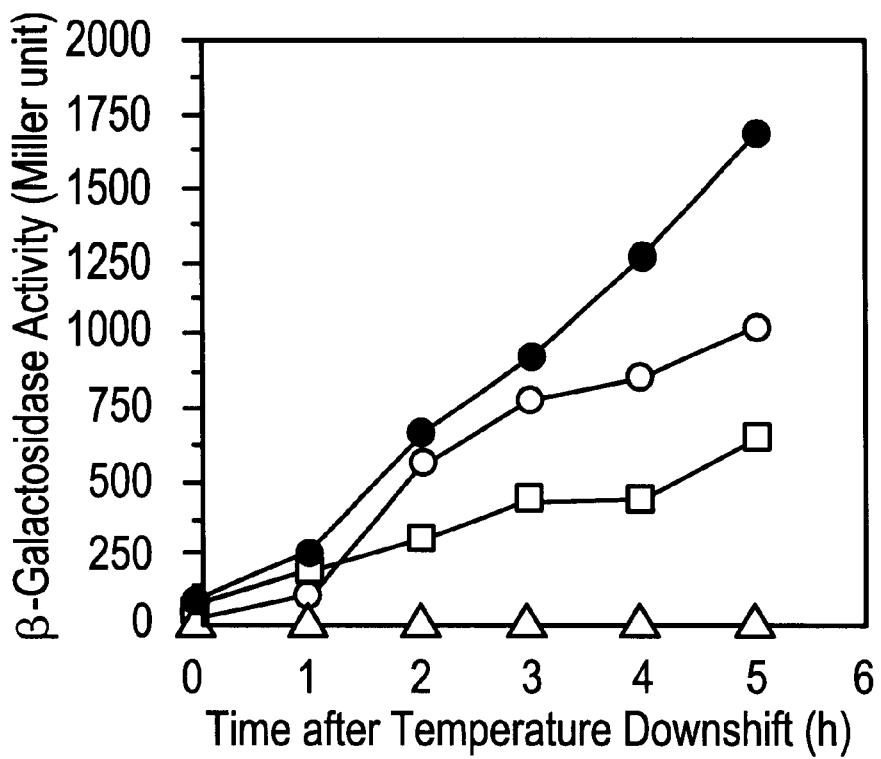

FIG. 22 is a graph of the cold shock induction of β-galactosidase activity of various plasmids.

Figure 23:
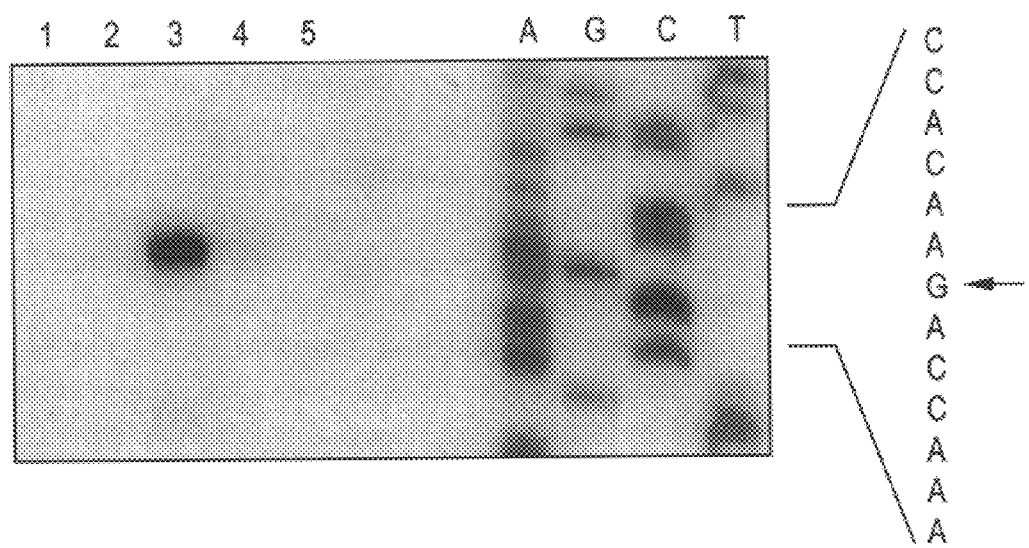
Figure 24A:
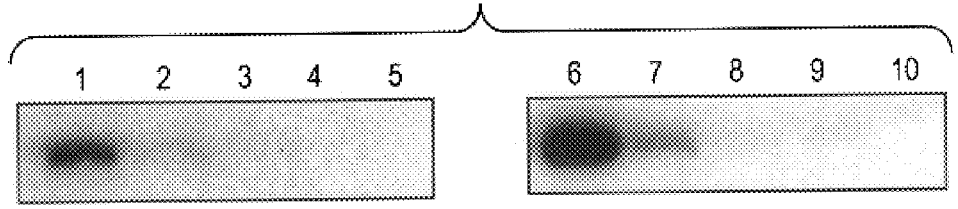
Figure 24B:
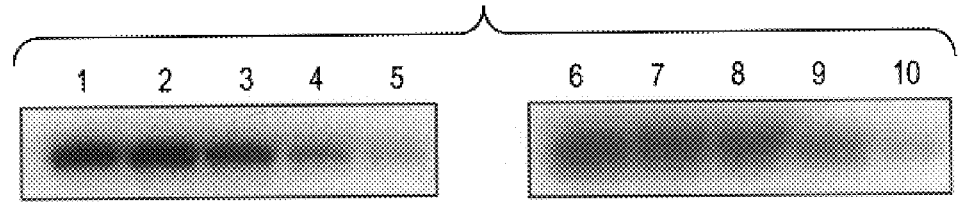
Figure 24C:
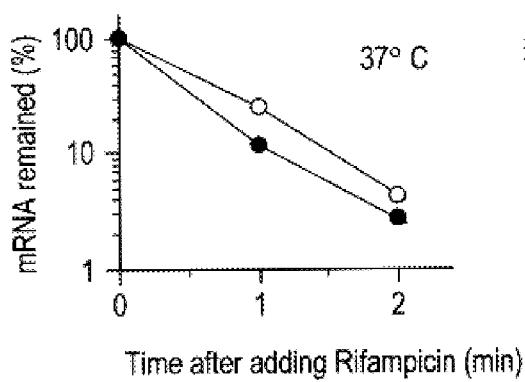
Figure 24D:
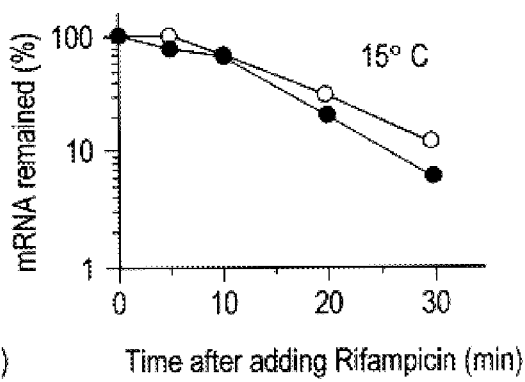

FIG. 23 is a photograph of a primer extension analysis of the cspI mRNA.

FIGS. 24A–24D have panels A and B which include photographs an analysis of mRNA stability, along with panels C and D which are graphical representations of the same analysis.

Figure 25A:
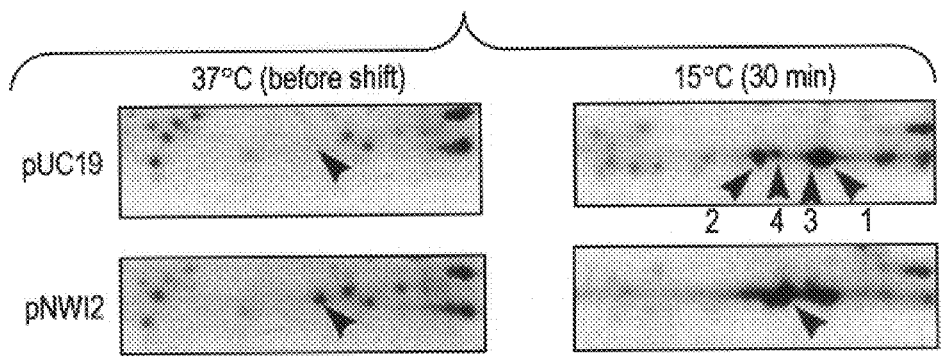
Figure 25B:
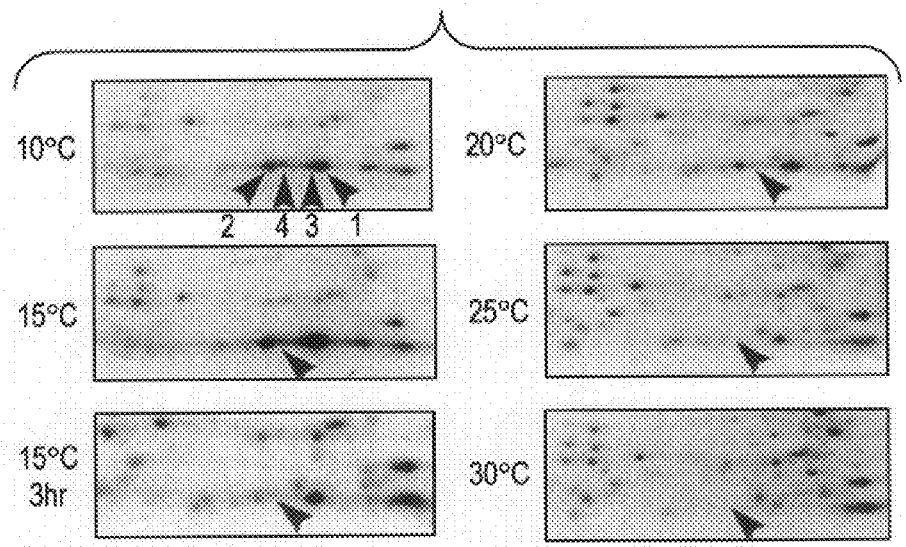

FIGS. 25A and 25B have photographs of 2D gel electrophoresis of CspI protein.

Figure 26A:
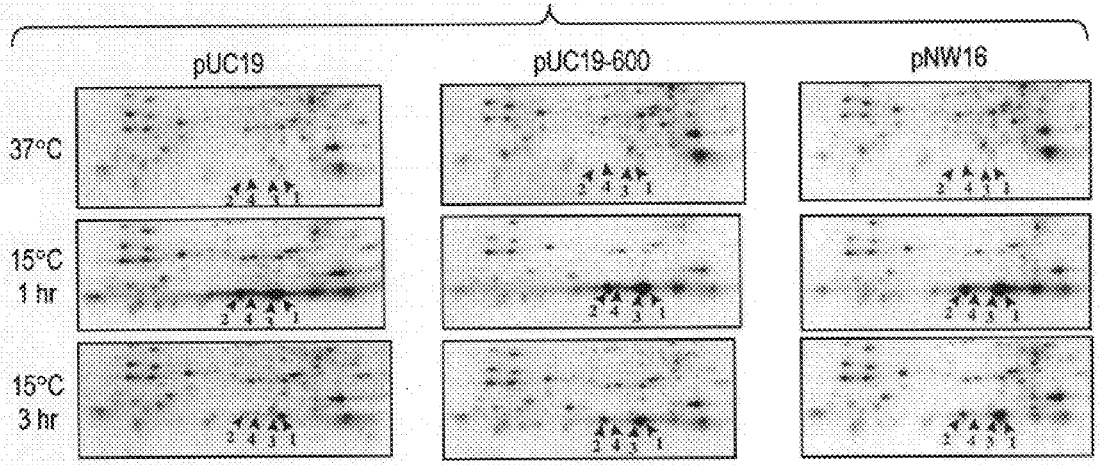

FIGS. 26A$a$–26A$i$ and 26B$a$–26B$c$ includes panel A which has photographs of the effect of cspI 5'-UTR overexpression on CspA, CspB, CspG, and cspI expression, and panel B which includes bar graphs of derepression rates.

SUMMARY OF THE INVENTION

The invention comprises an isolated nucleic acid molecule that prolongs the expression of a cold-shock inducible gene under conditions of physiologic stress that elicit the cold-shock response in bacteria.

The invention further comprises an isolated nucleic acid molecule that represses the expression of a cold-shock inducible gene under physiologic conditions.

The invention further comprises an isolated nucleic acid molecule that enhances translation of a cold-shock inducible gene under conditions of physiologic stress that elicits a cold shock response in bacteria.

What has been discovered is that three of the essential processes that govern the regulation of a genes that are expressed under conditions of physiologic stress that elicit the cold shock response of a bacterium are mediated by the 5'-untranslated region (5'-UTR) of the mRNA transcript encoding a cold shock inducible protein. It has been discovered that specific regions of the 5'-UTR of cold shock inducible mRNA transcripts mediate (A) the transient nature of cold shock gene expression after exposure of the cells to physiologic stress that induces the cold shock response, (B) the repression of cold shock gene expression at physiologic temperatures, and (C) enhancement of the translation of cold shock inducible mRNA transcripts by the ribosome.

It has also been discovered that DNA constructs encoding this regulatory element, either alone or in combination with themselves, or with other regulatory sequences known in the art, e.g., promoters, downstream boxes and transcriptional terminator sequences, can be exploited to prolong the expression and increase the efficiency of translation of a cold shock gene or of a heterologous gene under conditions of physiologic stress that induce the cold shock response of a bacterium, and repress the expression of the genes under normal physiologic conditions. This is advantageous for the hyper-expression of a desired protein product which may be unstable at physiologic temperatures, or may fold improperly and exist in inclusion bodies within the host cell at physiological temperatures, or may be degraded by the host cell.

The invention offers a further advantageous trait in that the translation of normal cellular proteins is inhibited under the conditions where the desired protein product is being hyper-expressed. This allows the desired product to accumulate in the host cell and simplifies the purification of the desired product from host cell polypeptides.

Accordingly, the invention also comprises transformed bacteria carrying the vectors which contain the above described element and transformed bacteria carrying a vector with the above described element and a target gene sequence for expression. Such target sequence can be a cold-shock gene sequence or a heterologous gene sequence.

DETAILED DESCRIPTION OF THE INVENTION

As reported by Sprengart et al., the downstream box (DB) of bacteria plays an important role in the translation of mRNA to produce proteins. The DB binds to a portion of the bacterial 16S rRNA near the 3' end and is thought to help position the mRNA and rRNA in proper relative position for translation to occur.

It has been discovered that during the time when the ADB is annealed to the DB of an overexpressed mRNA, the 16S rRNA is not capable of participation in the translation of cellular mRNAs other than the annealed overexpressed mRNA. It has been further discovered that the entire protein-making machinery of a bacterium may be shut down by providing to the bacterium an mRNA, which encodes a DB which is substantially complementary to the ADB of the 16S rRNA, which anneals to all or substantially all of the bacterial 16S rRNA.

The term "complementary" is used herein, it is intended to include "substantially complementary". Thus, the term "complementarity" does not require perfect complementarity. It is sufficient that the two sequences be "complementary" as defined in Kahl, Dictionary of Gene Technology, VCH Publishers, Inc. (1995), which is incorporated herein by reference. That is, two nucleotide sequences are complementary if they are capable of forming a hydrogen-bonded duplex with each other according to Watson-Crick base-pairing rules. Two complementary RNA sequences, or an RNA and a DNA sequence, will form pairings of A-U, G-C, or G-U. "Complete complementarity" is not required.

"Homologous" as used herein refers to molecules which have substantially the same molecular sequence of the referenced nucleic acid sequence, but may contain additions deletions, or substitutions. Homologous molecules are defined as those molecules which hybridize under low or high stringency conditions to a nucleic acid molecule that is precisely complementary to the referenced nucleic acid molecule and which performs the same function as the referenced nucleic acid.

By way of example, and not limitation, low stringency conditions for hybridization are: Filters containing DNA are pretreated for 6 hours at 40° C. in a solution of 35% formamide, 5×SSC, 50 mM Tris-HCL (pH 7.5), 5 mM EDTA, 0.1% PVP, 0.1% Ficoll, 1% BSA, and 500 μg/ml salmon sperm DNA, 10% (wt/vol) dextran sulfate, and 5–20×10$^6$ cpm $^{32}$P-labeled probe. Filters are then incubated in hybridization mixture for 18–20 hours at 40° C., and washed for 1.5 hours at 55° C. in a solutions containing 2×SSC, 25 mM Tris-HCL (pH 7.4), 5 mM EDTA, and 0.1%

SDS. The wash solution is replaced with fresh wash solution and incubated for an additional 1.5 hours at 60° C. The filters are blotted dry and exposed for autoradiography. If desired, or if required, a third wash step may be conducted for 1.5 hours at a temperature of 65–68° C. and the filters can be reexposed to film.

For example, and not by way of limitation, high stringency conditions may be as follows: Prehybridization of filters containing the nucleic acid to be probed is carried out for 8 hours to overnight at 65° C. in buffer containing 6×SSC, 50 mM Tris-HCL (pH 7.5), 1 mM EDTA, 0.02% PVP, 0.02% Ficoll, 0.02% BSA and 500 µg/ml denatured salmon sperm DNA. The filters are hybridized for 48 hours at 65° C. in a prehybridization mixture containing 100 µg/ml denatured salmon sperm DNA and 5–20×106 32P-labeled probe. Washing of filters is performed for 1 hour in a solution of 2×SSC, 0.01 PVP, 0.01% Ficoll, and 0.01% BSA at 37° C., followed by a wash for 45 minutes in 0.1×SSC at 50° C. The filters are blotted dry and exposed for autoradiography. Other protocols for high and low stringency hybridization known in the art may be substituted.

As is known, the ADB is a nucleotide sequence of about 14 bases which is positioned in the 3' end of the 16S rRNA, in close proximity to the decoding region of 16S rRNA. The 16S rRNA nucleotide sequence of known bacteria is known and can be found in the GenBank database. Thus, for a selected bacterium, the ADB can be readily identified by comparison to the sequence of the ADB in a bacterium in which the sequence is known, for example $E.$ $coli$. Once the ADB is identified, a DB complementary to the ADB can be constructed, and incorporated into an appropriate mRNA, as described below.

The mRNA of the invention is an isolated mRNA or an mRNA which has been transcribed from an isolated DNA. The mRNA comprises an initiation codon, which codon is preferably AUG. Other suitable initiation codons for the mRNA include GUG and UUG.

The mRNA of the invention further comprises a downstream box sequence, which is typically 3' to the initiation codon. The codons of the DB may or may not be in phase with the initiation codon. The DB sequence may be immediately adjacent to the initiation codon so that there are no intervening nucleotides. Generally, the DB is separated from the initiation codon by an intervening nucleotide sequence between 1 and 30 nucleotides long. The base sequence of the intervening sequence is immaterial and may be constituted of any sequence of nucleotides. Preferably, the intervening nucleotide sequence is 9 to 15 nucleotides in length, with a most preferred length of 12 nucleotides. Alternatively, the DB may overlap the initiation codon. That is, any one of the three nucleotides of the initiation codon of the mRNA of the invention may form the 5' end of the DB.

The DB sequence of the mRNA of the invention is a nucleotide sequence which is complementary to the ADB of the 16S rRNA of a bacterium. Generally, the DB is between 6 and 20 bases long, preferably between 8 and 14 bases long, although the DB may be longer than 20 bases. For example, the DB may comprise nucleotides which are complementary to nucleotides 3' or 5', or both, to the ADB. Regardless of length of the DB, a higher degree of complementarity between the DB and the ADB is associated with more effective annealing, resulting in more efficient inhibition of bacterial protein synthesis, in accordance with the method of the invention.

In addition to the initiation codon, the DB, and any intervening sequence, the mRNA construct of the invention may comprise a nucleotide sequence 5' to the initiation codon or 3' to the DB. For example, the mRNA construct may comprise a sequence 3' to the DB which encodes a polypeptide or may comprise a termination codon. Likewise, the mRNA construct may comprise an untranslated sequence and/or a Shine-Dalgarno sequence 5' to the initiation codon.

The length of the mRNA construct, including the initiation codon, any intervening sequence, and DB, and exclusive of any additional nucleotides at the 5' or 3' end, may be any length between 8 nucleotides to about 45 nucleotides. Of course, if the mRNA comprises a 5' or 3' sequence in addition to the above essential components, such as a Shine-Dalgarno sequence, the mRNA may be much longer, up to several hundreds of nucleotides in length.

Preferably, although not necessarily, the mRNA construct is free of sites for RNA endonucleases. It is especially preferred that the portion of the mRNA construct comprising the essential portions of the construct, that is the initiation codon and the DB, be free of sites for RNA endonucleases, which might otherwise degrade the mRNA construct and free the bacterial 16S rRNA to bind to bacterial mRNAs.

The mRNA construct of the invention may have a sequence which is similar or identical to an mRNA sequence found naturally in a bacterium. For example, the mRNAs for several cold-shock proteins, such as the mRNAs for $E.$ $coli$ proteins cspA, CspB, CspG, CsdA, and RbfA, comprise a Shine-Dalgarno sequence, an initiation codon, and a downstream box substantially complementary to the anti-downstream box of the $E.$ $coli$ 16S rRNA. Other $E.$ $coli$ mRNAs which contain a Shine-Dalgarno sequence, an initiation codon, and a downstream box complementary to the $E.$ $coli$ ADB include RecA, Hns, NusA, InfB, and CspD.

Below are several non-limiting examples of suitable DBs for the mRNA construct. Each of the following DB is substantially complementary to the ADB of the $E.$ $coli$ 16S rRNA which ADB has the sequence:

| | | |
|---|---|---|
| ADB | 3' (-1481)UACUUAGUGUUUCA(-1469) 5' | (SEQ ID NO: 1) |
| DB #1: | 5' AUGACUGGUAUCGU 3' | (SEQ ID NO: 2) |
| DB #2: | 5' AUGACUGGUUUCGU 3' | (SEQ ID NO: 3) |
| DB #3: | 5' AUGACUGGUUUAGU 3' | (SEQ ID NO: 4) |
| DB #4: | 5' AUGAGUUAUGUAGA 3' | (SEQ ID NO: 5) |
| DB #5: | 5' AUGGCGAAAAGAAU 3' | (SEQ ID NO: 6) |

A suitable mRNA construct according to the invention can be constructed using any one of the above DBs, or other suitable DB, for example:

5' AUGX$_{(n)}$AUGACUGGUAUCGU 3' (SEQ ID NO: 7)
where n is a whole number from 0 to 30, and X is G, C, U, or A, wherein each occurrence of X may be the same as or different from any other occurrence of X. Alternatively, the 5' end of the DB overlaps the initiation codon.

The DNA of the invention is any isolated DNA which encodes for an mRNA which is suitable for the mRNA construct of the invention, as described above. The DNA may further comprise an additional nucleotide sequence 5' to the initiation codon, which sequence may include a promoter sequence. Such promoter sequences may be used to control transcription of the mRNA construct. The DNA may comprise a sequence 5' to the initiation codon which sequence has a function other than as a promoter, such as a Shine-Dalgarno sequence, and/or a sequence which has no known function. The DNA may comprise a sequence 3' to the portion encoding the DB of the mRNA construct, which sequence may include, for example, a termination codon, or may encode a polypeptide, and a sequence required for transcription termination.

An example of a suitable DNA which encodes for the mRNA construct of the invention is: 5' ATGY$_{(n)}$ ATGACTGGTATCGT 3' (SEQ ID NO: 8) where n is a whole number from 0 to 30, and Y is G, C, T, or A, wherein each occurrence of Y may be the same as or different from any other occurrence of Y. Alternatively, the 5' end of the DB overlaps the initiation codon, ATG. The DNA may contain additional sequences, as stated above, at the 5' and/or 3' end of the DNA.

The DNA sequence of the invention may be contained within a vehicle or cloning vector, such as in a plasmid or phage vector. The DNA sequence in the vector may be under the control of a promoter sequence located 5' to the initiation codon. These vectors containing the DNA of the invention may be used to transform a host bacterium which may be used to overexpress the mRNA of the invention, that is to produce the mRNA in the bacterium at levels higher than produced in similar non-transformed bacteria. Any bacterium which may be transformed by means of a cloning vector is a suitable host for the DNA sequence of the invention. Methods of producing cloning vectors and transforming bacteria are known in the art and are taught, for example, in Ausubel et al., Current Protocols in Molecular Biology, J. Wiley & Sons, Inc. (1995), which is incorporated herein by reference.

Overexpression of the mRNA sequence of the invention results in the production of the mRNA in an amount which is higher than that found normally in the bacteria. To whatever extent the mRNA is overexpressed, the production of bacterial proteins is inhibited. If the mRNA is expressed at a high enough level, production of bacterial proteins will be completely stopped, which may lead ultimately to death of the bacterium.

Therefore, the construct producing the mRNA is useful as an antibiotic to kill or to stop the growth of bacteria. The construct producing the mRNA may be packaged in a bacteriophage which would permit the mRNA to be used as a disinfectant or as a topical antibiotic preparation. It is conceivable that strategies for delivery will be devised to permit transformation of bacteria which are causing infection of a plant or animal, such as a mammal like humans, dogs, cats, cattle, horses, and livestock. Such antibiotics are safe for use in eukaryotes, as eukaryotes lack the 16S rRNA that is present in bacteria.

According to the method of the invention, an mRNA comprising an initiation codon and a DB which is complementary to the ADB of the 16S rRNA of a bacterium, is caused to be overexpressed in a bacterium, and is then allowed to anneal to the ADB of the 16S rRNA of the bacterium, thereby inhibiting production of proteins encoded by other mRNAs in the bacterium.

Any means of delivery which results in overexpression of the mRNA of the invention is suitable for the method of the invention. For example, the bacterium may be transformed by means of a vehicle harboring a DNA sequence which codes for the mRNA of the invention.

If desired, expression of the mRNA sequence of the invention is controlled by placing the DNA sequence under the control of an inducible promoter. For example, if it is desired to kill a harmful bacterium or block its growth while sparing a beneficial bacterium, the DNA sequence may be placed under the control of a promoter which is responsive to a product which is present only in the first bacterium. In this way, the lethal antibiotic effect of the mRNA of the invention will affect only the undesirable, harmful bacterium.

Another means of controlling the expression of the protein production-inhibiting mRNA sequence is to employ a DNA sequence which codes for an mRNA which is unstable under certain conditions.

For example, the 5' untranslated region (5' UTR) of the mRNA of the E. coli cold-shock protein, cspA, contains a region immediately 5' to the Shine-Dalgarno region which is susceptible to degradation, presumably by RNAase E, at physiologic growth temperatures of about 37° C. Therefore, the cspA mRNA containing the 5' UTR is unstable under normal growth conditions, having a half life estimated to be approximately 12 seconds. Other cold-shock proteins, such as E. coli CspB and CsdA, are similarly unstable at physiologic growth temperatures due to instability of their mRNA. Upon cold shock, such as when the temperature is reduced to 15° C., the half life of the cspA mRNA increases dramatically, to about 15 minutes, an increase in stability of about 75 times over the mRNA at normal physiologic growth temperatures.

Because of the instability at 37° C. of an mRNA containing the 5' UTR of cspA mRNA, this region, or the 5' UTR of the cspB or csdA mRNA, can be used to control the expression of the mRNA sequence of the invention, so that its antibiotic effect occurs only below physiologic growth temperatures, such as under cold-shock conditions. The antibiotic effect of the method of the invention is augmented at cold-shock conditions because a cold-shocked bacterium requires new ribosomal factors, whose synthesis is blocked by overproduction of an mRNA containing the DB sequence.

The antibiotic effect of the method of the invention in which the mRNA of the invention is caused to be overexpressed within a bacterium is increased concomitantly with an increase in copy number of the mRNA which is to be expressed. That is, whereas a minimal overexpression of the mRNA of the invention will inhibit the production of proteins by the bacterium, such an inhibition may not be sufficient to prevent further growth of the bacterium or to kill the bacterium. Higher levels of expression of the mRNA result are positively correlated with increased inhibition of protein production. When the copy number is sufficiently high in the bacterium, protein production will be completely blocked.

A similar effect is noted with respect to complementarity of the DB of the overexpressed mRNA and the ADB of the bacterial 16S rRNA. Overexpression of an mRNA comprising a DB with 100% complementarity will be more efficient in binding to the ADB than will be an mRNA comprising a DB with lesser (75%) complementarity. Thus, the protein blocking effect of an mRNA having a more highly complementary DB will be more pronounced compared to that of an mRNA having a less complementary DB. Therefore, when using an mRNA having a less complementary DB, it may be useful to express the mRNA in a higher copy number to achieve the same or similar antibiotic results as with an mRNA having a more complementary DB.

The translational inhibitory properties of the downstream box are also advantageous for overexpressing a heterologous gene in a transformed bacterium after cold shock. Inhibition of the translation of endogenous bacterial proteins will allow the heterologous gene product to accumulate to very high levels in the transformed organism. Furthermore, a construct containing the downstream box in conjunction with a strong promoter and the 5' untranslated region of a cold shock inducible gene, which functions to stabilize the mRNA transcript at reduced temperature, will direct efficient high level expression of the heterologous gene at reduced temperature.

Another important embodiment of the invention relates to the role of the 5'-end untranslated region of the mRNA for cspA, the major cold-shock protein of *Escherichia coli*, in cold shock adaption.

When the culture temperature of exponentially growing *Escherichia coli* cells are shifted from 37 to 10° C., there is a growth lag period before reinitiation of cell growth (Jones et al. 1987). Similar to the heat-shock response, *E. coli* responds to the temperature downshift by inducing a specific pattern of gene expression called cold-shock response, which includes induction of a set of proteins defined as cold-shock proteins (Jones et al. 1992; for review, see Jones and Inouye 1994). The cold-shock response occurs during the lag period of cell growth, and is considered to be required for cellular adaptation to low temperature.

cspA, the major cold-shock protein in *E. coli*, is dramatically induced upon temperature downshift, whose production reaches as high as 13% of total protein synthesis (Goldstein et al. 1190). Interestingly, however, cspA production during cold-shock response is transient and drops to a basal level at the time of reinitiation of cell growth at low temperature. cspA consists of 70 amino acid residues, and shows 43% identity to the "cold-shock domain" of the eukaryotic Y-box protein family which is known to be associated with gene regulation and mRNA masking (for review, see Wolffe et al. 1992; Wolffe 1993). The three-dimensional structure of cspA has been determined, consisting of five anti-parallel B-sheets which form a B-barrel structure (Newkirk et al. 1994; Schindelin et al. 1994). Two RNA binding motifs, RNP1 and RNP2, are identified on B2 and B3 sheets, respectively. In the structure, seven out of eight aromatic residues are located on the same surface and a single-stranded DNA was shown to interact with these surface aromatic residues (Newkirk et al. 1994). It has been proposed that cspA function as an RNA chaperone to facilitate translation efficiency at low temperature (for review, see Jones and Inouye 1994).

*E. coli* contains a large cspA family, including cspB, cspC, cspD, and cspE (Lee et al. 1994; Dongier et al. 1992; Yamanaka et al. 1994). Among them, only cspA and cspB have been shown to be cold-shock inducible (Lee et al. 1994).

CspA was revealed to cooperatively bind to RNAs and single-stranded DNAs and is considered to function as an RNA chaperone, which may prevent the formation of secondary structures of mRNAs for efficient translation at low temperatures.

The cspA promoter is highly active at 37° C., although CspA protein is hardly detected at this temperature, indicating that cspA expression at low temperatures is regulated posttranscriptionally. It should be mentioned, however, that the AT-rich sequence immediately upstream of the 35 region of the cspA promoter functions as a UP element to enhance cspA transcription. The cspA mRNA is extremely unstable at 37° C. but is dramatically stabilized upon cold shock. The cspA mRNA possesses an unusually long 5' untranslated region (5'-UTR) consisting of 159 bases. Mutation analyses have shown that the 5'-UTR of the cspA mRNA plays a crucial role in its cold shock inducibility. In addition, translation initiation of the cspA mRNA appears to be very efficient at low temperature in comparison with mRNAs of non-cold-shock proteins. Thus, the cspA expression is regulated in a complex manner, that is, at the levels of transcription, mRNA stability and translation efficiency.

cspA induction occurs transiently during the acclimation phase upon cold shock, as mentioned above. At the end of the acclimation phase, cspA expression is repressed to a new basal level. It has been proposed that the cold box sequence, which is located in the 5'-UTR, and a factor which might bind to the cold box to repress the cspA expression at the level of transcription are responsible for autoregulation of cspA expression.

Six additional cspA homologues in *E. coli*, cspB to cspG, have been identified by means of Southern analysis with cspA as a probe (cspB and cspC), isolation of multicopy suppressors of a chromosome partition mutant (cspC and cspE) and cold shock induction (cspG). Of these, cspA, cspB, and cspG are cold shock inducible and cspC and cspE are expressed at both high and low temperatures. cspD is located upstream of cspA and is induced during stationary phase and upon nutrition starvation. cspF is closely linked to cspB; however, its function is not known. cspA, cspB, and cspG mRNAs share a highly conserved, long 5'-UTR sequence, suggesting that the expression of cspB and cspG is regulated in a similar way to that of cspA. It should be noted, however, that CspB and CspG are induced in a narrower range of low temperature than is CspA. cspA is dispensable for growth at either 37 or 15° C., and the production of CspB and CspG increased in a cspA deletion strain, suggesting that they may have similar functions.

Upon completion of *E. coli* genome sequencing, two more CspA homologues, designated CspH and CspI, were found. They show the highest similarity to CspF and CspG, respectively. Although the primary amino acid sequence of CspI shows high identity not only to CspG (79%) but also to CspA (70%) and CspB (70%), the region corresponding to the highly conserved 5'-UTR of cspA, cspB, and cspG is less highly conserved in cspI.

Here we demonstrate that cspI is another cold shock gene, as judged by lacZ expression of both the transcriptional and the translational cspI-lacZ fusions and by cspI production, determined by two-dimensional gel electrophoresis. As shown for cspA, the cspI mRNA was dramatically stabilized upon cold shock and the overproduction of the cspI 5'-UTR caused derepression of cspA, cspB, cspG, and cspI. In addition, the cspI gene was induced in the lowest temperature range (15 to 10° C.), suggesting that CspI may play an important physiological role in growth at very low temperature.

Cold Box

In one embodiment of the invention, a DNA sequence is capable of prolonging the normally transient expression of the cold shock genes during the adaptation of a bacterium to physiologic stress that elicits the cold shock response. Thus, the transient nature of the cold shock response and the normally transient expression of the cold shock inducible gene is blocked and expression is continued at high levels for an extended period of time, such as at least 2 to 3 hours. The DNA sequence that is competent to confer this activity comprises the 5'-UTR or at least a portion of the 5'-UTR of a cold shock inducible mRNA transcript and a promoter, active under conditions of physiologic stress that induce the cold shock response in a bacterium. Furthermore, it was found that not the entire 5'-UTR was essential, but that the sequence responsible for blocking the transient expression of the cold shock genes, like cspA, resides within the first twenty five nucleotides of the 5'-UTR.

Comparison of this nucleotide sequence which is competent for this activity with other cold shock genes showed that cspB, cspG and csdA possessed similar sequences within their respective 5'-UTR and were expressed in a transient manner in response to physiologic stress that induces the cold shock response. This suggests that these genes are regulated in a similar manner to cspA. Based upon these sequence comparisons, the sequence responsible for this activity, hereafter designated the cold box, was shown to be situated between nucleotides +1 and +11 of the 5'-UTR of cspA, cspB, cspG and csdA.

The cold box normally functions to down regulate the expression of cold shock genes. This was shown by hyperexpression of just the cspA 5'-UTR in E. coli, which resulted in a prolongation of the expression of cold shock inducible genes in these cells. The cold box functions probably by interacting with the CspA protein itself, or with another protein whose function is dependent upon cspA. This was shown by subsequently hyper-expression the CspA protein in the E. coli cells described above and observing a suppression of the prolonged expression. Therefore, the cold box appears to comprise a repressor binding site that functions to repress the expression of cold shock genes after their induction, resulting in transient expression of these genes. As the levels of CspA protein increase after induction of its gene, the cspA begins to interact with the cold box, either directly by binding the cold box sequence or indirectly by stimulating another factor to interact with the cold box, resulting in repression of the cold shock inducible genes.

Repressor of Cold Shock Gene Expression at Physiologic Temperatures

The 5' UTR is unique is that it is longer than most E. coli UTRs. It plays multiple functions in cspA expression. It represses cspA expression at 37° C. These different activities have been mapped by Mitta et al (unpublished manuscript) by constructing and analyzing defined deletions through the 5'-UTR region. The sequences mediating repression of cspA expression at 37° C. reside between +56 and +117 of the 5'-UTR of cspA (see Mitta, unpublished manuscript). It is likely that optimal repression requires other sequences in the 5'-UTR as well. In other words, the effect of deleting the +56 to +117 region was significant, but did not account for the entire level of repression observed with the intact 5'-UTR. Thus, his conclusion that other sequences may also play a role in repressing cspA expression at 37° C. However, the localization of at least a portion of the repression activity to a specific region of the 5'-UTR is novel. The 5'-UTR is starting to be dissected into functional domains and the +56 to +117 region represents a new functional region.

The UTR also has a positive effect on mRNA stability at 15° C. This was determined by noting an increase in steady state levels of mRNA of constructs having the UTR. However, even though more mRNA was present in these experiments, the mRNA was not translated unless the DB was present.

The effects of increasing RNA stability and increasing RNA translatability are thus mediated by independent sequences of the cspA transcript. However, the specific sequences that mediate mRNA stability are not well characterized in this region.

Translational Enhancement of Cold Shock mRNA

The 5'-UTR enhances the translatability of cspA transcripts through a sequence situated between +117 and +143 of the 5' UTR. Comparison of this region between different cold shock inducible revealed a 13 base sequence (+123–+135) having the sequence 5'-GCCGAAAGGCACA-3' (SEQ ID NO:9) that was conserved among cspA, cspB, and cspG and may represent enhancer of translation. Thus, this sequence mediates efficient translation of the mRNA that possesses it. This 13 base region exhibits homology with the 16S rRNA, similar to what was previously observed with the DB, but the new translational enhancer region is complementary to a different region of the 16S rRNA than DB. Therefore, this region of the 5'-UTR may also assist in translating csp mRNAs by a mechanism similar to the downstream box interactions with ribosomal RNA.

In another embodiment of the invention, expression plasmids, capable of high level expression of cold shock inducible genes, or of a heterologous gene, are constructed. Such expression plasmids contain DNA fragments encoding the 5' UTR or a portion or portions thereof of a cold shock inducible gene, comprising one or more of the regulatory elements described above, positioned downstream of a promoter that is functional under conditions of physiologic stress that induce the cold shock response in a bacterium. Such promoters may be selected from the group including the cspA, cspB, cspG or csdA promoters, the E. coli llp promoter, or any other such promoter that is active under conditions of physiologic stress. Such expression plasmids may also contain, downstream of the promoter and DNA fragment encoding the 5'-UTR comprising one or more of the regulatory elements described, a transcriptional terminator sequence. Examples of transcriptional terminator sequences are well known in the art and include sequences such as the E. coli rrnB terminator.

The expression plasmids of the invention may also comprise a restriction site, or a sequence comprising multiple restriction sites, such site or sites situated between the 5'-UTR encoding one or more of the regulatory elements and the transcriptional terminator to facilitate the insertion of a heterologous gene.

Finally, the expression plasmids of the invention may comprise additional sequences known in the art to facilitate the efficient translation of the expressed gene. Such sequences may include a Shine-Dalgarno sequence, situated between the 5' UTR sequence and the restriction site(s) and/or a DNA fragment encoding a downstream box, situated between the Shine-Dalgarno sequence and the restriction site(s). The source of the Shine-Dalgarno sequence is not especially limited, and may be derived from cold shock proteins or may be from another gene. Such expression plasmids are capable of directing high level expression of a heterologous gene for a prolonged period of time under conditions of physiologic stress that elicit the cold shock response of a bacterium. Under these conditions, the synthesis of endogenous proteins by the host bacterium is blocked, allowing the product of the heterologous gene to accumulate to high levels within the cell.

In a preferred embodiment of the invention, the expression vector comprises a promoter, a 5' UTR, cold box, Shine-Dalgarno sequence and a downstream box (DB). This expression vector may be used so that a nucleic acid molecule encoding a target protein may be ligated into the expression vector using at least one restriction site.

In another embodiment of the invention, nucleic acid molecules encoding proteins that are unstable, or that fold improperly in the bacterial host cell at physiologic temperatures can be expressed at temperatures below the physiologic temperature of the host bacterium. Such nucleic acid molecules may be inserted, preferably in-frame to the restriction site or sites to allow transcription of the nucleic acid and translation of the resulting mRNA. Such conditions may facilitate the proper folding, increase the stability or decrease the rate of degradation of the expressed product.

The plasmids or vectors may be used to transform bacteria by any method known in the art, including, but not limited to calcium chloride transformation, electroporation, and the like. The bacterial species which may be transformed is not particularly limited. In a preferred embodiment, *Escherichia coli* is used. The transformed bacteria may be used to overexpress a target protein of interest, or may be used to produce large amounts of the plasmids or vectors for subsequent isolation and purification.

In a preferred embodiment for overexpression of a target protein, a nucleic acid molecule encoding a target protein is ligated into the plasmid using one or more restriction sites, preferably in-frame to the initiation codon, if an initiation codon is provided upstream of the insertion site for the target protein. Alternatively, if the nucleic acid molecule encoding the target protein has its own initiation codon, the nucleic acid encoding the target protein may be ligated into the plasmid such that its own initiation codon will serve as the initiation codon in the transcript.

The constructs may be designed and assembled to include a selectable marker. That is, for example, a drug resistance gene which allows transformed bacteria to grow in the presence of a drug which does not permit the growth of non-transformed bacteria. Any selectable marker known in the art may be used. Examples of selectable markers include, but are not limited to ampicillin resistance, neomycin resistance, kanamycin resistance and tetracycline resistance.

The constructs may also include an inducible promoter. The inducible promoter may direct the synthesis of the target protein upon induction. For example, and not by way of limitation, a lacZ promoter may be included which may be induced by the addition of IPTG to the culture medium.

In a preferred embodiment, the constructs will contain a promoter which is active under conditions that elicit a cold-shock response in bacteria, such as by shifting the temperature of the culture medium containing the transformed bacteria to 10–15° C. Preferably, overexpression of a target protein in conditions that elicit a cold-shock response reduces the synthesis of at least one native bacterial protein. More preferably, the synthesis of many native proteins is reduced or blocked.

The following examples are provided to illustrate aspects of the invention and are not to be construed in any way as limiting the scope of the invention, which is defined in the appended claims.

EXAMPLES

Bacterial strains, plasmids, and media. *E. coli* JM83 and AR134 (MC4 100 pcnB80) were used. Plasmid pUC19 was used for cloning. Plasmids pRS414 and pRS415 were used for construction of lacZ fusions. Plasmid pCspA-LacZ, in which the cspA upstream region and the first 13 codons of cspA were fused translationally to lacZ on the pRS414 vector, as described previously, was used as a control.

Luria-Bertani (LB) and M9 media, supplemented with 0.4% glucose, 0.4% Casamino Acids, and 50 µg/ml of thiamine, were used for bacterial growth. When necessary, ampicillin was added at a final concentration of 50 µg/ml.

General techniques. DNA cloning was carried out by the method described previously. PCR amplification was carried out as specified in the manufacturer's instruction manual (Boehringer) with 30 cycles of amplification steps each of 1 min at 95° C., 2 min at 50° C., and 2 min at 72° C. Restriction enzymes and DNA modification enzymes were purchased from Boehringer, Gibco BRL, and New England Biolabs.

Example 1

Construction of Plasmids pJJG02 was constructed from pJJG01 (Goldstein et al., 1990) as follows: A 998-bp fragment which contains the entire cspA gene was obtained from pJJG01 by HindIII and XmnI digestion. This fragment was then treated with the Klenow fragment of DNA polymerase (Life Technologies), and inserted into the SmaI site of pUC9.

pJJG21 was constructed from pJJG02 by creating an XbaI site immediately upstream of the Shine-Dalgarno sequence of cspA as follows: +13AAT<u>T</u>T(A)<u>C</u>(T)TA<u>G</u>(A)AGGTAA+153 (SEQ ID NO: 9) (the original nucleotides in the parentheses were substituted by the underlined nucleotides; ref. 1). pJJG81 was constructed from pJJG02 by creating an XbaI site immediately downstream of the transcription initiation site of cspA as follows: +1ACGGTTCTAGACGTA+15 (SEQ ID NO: 10) (nucleotides underlined represent the inserted bases).

pJJG78 is a transcriptional fusion of the 0.6-kb cspA upstream region and lacZ as follows: the 1-kb EcoRI/BamHI fragment containing cspA from pJJG2I was filled in with Klenow enzyme and ligated into the SmaI site of pUC19. Then, the 0.6-kb XbaI fragment containing the cspA regulatory region (from −457 to +143) was excised and ligated into the XbaI site in pKM005 (Inouye, M. et al., 1983) in the correct orientation.

pUC19-600 was constructed by insertion of the 0.6-kb EcoRI/XbaI fragment from pJJG21 into the EcoRI/XbaI sites of pUC19. pJJG81/X,S containing fragment 1 (FIG. 3) was constructed by removing the 0.74-kb XbaI/SalI fragment from pJJG81. Both ends were treated with Klenow fragment, followed by self-ligation. All the other constructs shown in FIG. 3 were made by PCR (Boehringer Mannheim protocol). PCR amplified fragments were inserted into the SmaI site of pUC19. All PCR products were confirmed by DNA sequencing (Sanger et al., 1977).

p2JTEK was constructed as follows: PCR product by primer 3549 5'-CGGCATTAAGTAAGCAGTTG-3' (SEQ ID NO: 11) and primer 4428 5'-CTGGATCCTTTAATGGTCTGTACGTCAAACCGT-3' (SEQ ID NO: 12) was cloned into the SmaI site of pUC19. This PCR product contains cspA from −146 to +25 as the cspA transcription start site is defined as +1. Then the transcriptional terminator of cspA was amplified by PCR using primer 6290 5'-CGGAATTCAGCCTGTAATCTCT-3' (SEQ ID NO: 13) and 4860 5'-CTGTCGACTTACTTACGGCGTTGC-3' (SEQ ID NO. 14). The PCR product was then digested with EcoRI then cloned into the plasmid described above which was digested with EcoRI and SspI. The 52-bp KpnI and EcoRI fragment from Bluescript II SK was then cloned into the EcoRI and KpnI site. All PCR products were confirmed by DNA sequencing (Sanger et al., 1977).

p6mTEK was constructed in the same way as p2JTEK except that the first PCR was carried out with different primers: primer 3552 5'-GACAGGATTAAAAATCGAG-3' (SEQ ID NO: 15) and 6196 5'-AACCGTTGATGTGCA-3' (SEQ ID NO: 16). This PCR product encompasses cspA from −278 to +6 as the cspA transcription start site is defined as +1. All PCR products were confirmed by DNA sequencing (Sanger et al., 1977).

The pulse-labeling experiments were carried out as described previously (Jiang et al., 1993). Proteins were analyzed either by polyacrylamide SDS-gel electrophoresis (Inouye S. et al., 1982) or by two-dimensional electrophoresis as described previously (Jones et al., 1987).

Each 5'-UTR deletion was introduced by two step PCR. For the first step, two PCRs were carried out for each mutation. One reaction was done with a combination of primer 67F, 5'-ccttgctagCCGATTAATCATAAATATG-3' (SEQ ID NO: 17) (nucleotides −67 to −49 of cspA), and mutation primer R, which contains desired mutated sequence and is complimentary to cspA, and the other was done with primer #4311, 5'-ccggatccagGTTGAACCATTTT-3' (SEQ ID NO: 18) (complementary to +186 to +198) and mutation primer F, which also contains the same mutation and is same direction to cspA. The lower cases are extra nucleotides to create NheI or BamHI site (underlined) and the numbers are given using major transcription initiation site at +1, which was determined by Tanabe et al. (1992). For construction of pMM022, pMM023, pMM024, pMM025, and pMM026, primer DIR, 5'-ACTACACT/TTGATGTGCATTAGC-3' (SEQ ID NO: 19) (complementary to −15 to +1/+28 to +35), primer D2R, 5'-CAACGATAA/GCTTTAATGGTCTGT-3' (SEQ ID NO: 20) (complementary to +13 to +27/+56 to +64), primer D3R, 5'-TAAAGG/CTCTTGAAGGGACTT-3' (SEQ ID NO: 21) (complementary to +41 to +55/+86 to +91), primer D4R, 5'-CGGCGATAT/AATGTGCACTACGAGGG-3' (SEQ ID NO: 22) (complementary to +69 to +85/+118 to +126), and primer D5R, 5'-TACCTTTAA/GGCGTGCTTTACAGATT-3' (SEQ ID NO: 23) (complementary to +101 to +117/+144 to +152) was used as the mutation primer R and primer D1F, 5'-GCACATCAA/AGTGTAGTAAGGCAA-3' (SEQ ID NO: 24) (nucleotide −8 to +1/+28 to +42), primer D2F, 5'-TAAAGC/TTATCGTTGATACCC-3' (SEQ ID NO: 25) (nucleotide +22 to +27/+56 to +70), primer D3F, 5'-TCAAGAG/CCTTTAACGCTTCAAAA-3' (SEQ ID NO: 26) (nucleotide +49 to +55/+86 to +102), primer D4F, 5'-GCACATT/ATATCGCCGAAAGGC-3' (SEQ ID NO: 27) (nucleotide +79 to +85/+118 to +132), and primer D5F, 5'-AAAGCACGCC/TTAAAGGTAATACACT-3' (SEQ ID NO 28) (nucleotide +108 to +117/+144 to +159), was used as the mutation primer F, respectively, where the position of each deletion is indicated by a slash. A plasmid, pJJG02 (Goldstein et al. (1990), which contains the wild-type cspA, was used as template DNA. Then, each set of the first PCR products were mixed, heat denatured, annealed, and extended by Taq polymerase. The resulting products were further amplified by PCR using primer 67F and primer #4311. The final PCR products were digested with NheI and BamHI, and inserted into the XbaI-BamHI site of pKM005 (Inouye 1983). For pKNJ37, the PCR fragment was cloned into the XbaI-BamHI site of pRS414X, a pRS414 derivative (Simons et al., 1987), in which the unique SmaI site has been changed to an XbaI site.

For the construction of pMM007, PCR was carried out using primer 67F and primer #4311 as primers and pJJG02 as a template. The PCR fragment was digested with NheI and BamHI, and inserted into the XbaI-BamHI site of pRS414X.

pKNJ38 was constructed as follows: oligonucleotide #8509, 5'-CTAGCCGAAAGGCACAAATTAAGAGGG TATTAATAATGAAAGGGGGAATTCCA-3' (SEQ ID NO: 29), and oligonucleotide #8510, 5'- AGCTTGGAATTC-CCCCTTTCATTATTAATACCCTCTTAATTT GTGCCTTTCGG-3' (SEQ ID NO: 30) were first annealed and then cloned into pKM67 (Mitta et al., 1997) digested with XbaI and HindIII.

The DNA sequences of all the constructs were confirmed by DNA sequencing using the chain-termination method (Sanger et al., 1977). The DNA sequences of all the constructs were confirmed by DNA sequencing using the chain-termination method (Sanger et al., 1997).

E. coli AR137 harboring different plasmids was grown at 37° C. to mid-log phase in 15 ml of M9-Casamino acid medium using a 125-ml flask. The culture was then transferred to a 15° C. shaking water bath. Culture temperature reached 15° C. from 37° C. within 2 to 3 min under the condition used. A 1.5-ml culture was taken immediately before the temperature downshift (0 hr), and at 1, 2, 3, 5, 7, and 10 hr after the temperature downshift. β-galactosidase activity of the culture was measured according to Miller (1972). The assay was done in duplicate at each time points.

Plasmid Construction cspB DNA fragments were amplified by PCR using synthetic oligonucleotide primers containing the BamHI site at the 5' end. A plasmid, pSJ7 (Lee et al., 1994) carrying the wild-type cspB gene was used as a template DNA to create the PCR fragments B3, B13 and B17. The 5'-end oligonucleotide primer used in each of the above PCR reactions is 5'-CCGGATCCAGCTTTAATATAGCT-3' (SEQ ID NO: 43). The 3'-end oligonucleotide primers for the PCR products B3, B13, and B17 were 5'-CCGGATCCAGATTTGACATTCTACA-3' (SEQ ID NO: 44), 5'-CCGGATCCAGGTTAAACCATTTT-3' (SEQ ID NO: 45), and 5'-CCGGATCCAGACCTTTATCAGCGTT-3' (SEQ ID NO: 46), respectively. A deletion of the SD sequence in the cspB gene was created by site-directed mutagenesis using the QuickChange™ Site Directed Mutagenesis Kit (Stratagene). The PCR reaction was carried out using the pSJ7 plasmid as a template and the oligonucleotides Bsd1 (5'-GAAAGGCTCAAGTTACTTCATGTAGAATG-3') (SEQ ID NO: 47) and Bsd2 (5'-CATTCTACATGAAGTAACTTGAGCCTTTC-3') (SEQ ID NO: 48) to create pSJ7sd. pSJ7sd was used as a template to make the PCR fragments B13sd and B17sd. The 5' and 3' end oligonucleotide primers used in these PCR reactions are the same as the ones used for the PCR fragments B13 and B17. All of the above PCR products were cloned at the BamHI site of pRS414 vector (Simmons et al., 1987; Lee et al., 1994) to create the pB3, pB13, pB13sd, pB17, and pB17sd constructs.

The cspA-lacZ fusion constructs were made by the insertion of annealed oligonucleotides at the EcoRI site of the pJJG78 (Jiang et al., 1996). Annealed oligonucleotides DB1 (5'-AATTAATCACAAAGTGGG-3') (SEQ ID NO 31) with DB1 (5'-AATTCCCACTTTGTGATT-3') (SEQ ID NO: 32) or DB2 (5'-AATTATGAATCACAAAGTGGG-3') (SEQ ID NO: 33) with DB2' (5' AATTCCCACTTTGTGATTCAT-3') (SEQ ID NO: 34) were used to create pJJG78DB1' or pJJG78DB2 constructs, respectively.

The pIN-lacZ constructs were made by inserting the XbaI-SalI fragments from pJJG78 or pJJG78DB2 into the XbaI-SalI sites of pIN-III (Jiang et al., 1996) to create pINZ and pINZDB1, respectively. Then, the annealed oligonucleotides ZDB2 (5'-CTAGCCCTTATTAATAA TGAAAGGGGGAATTATGAATCACAAAGTGGG-3') (SEQ ID NO: 35) with ZDB2' (5'-AATTCCCACTTTGTGATTCATAATTCCCCCTTTCATT ATTAATAAGGG-3') (SEQ ID NO: 36) were inserted at the XbaI-EcoRI sites of pINZ to create pINZDB2. Annealed oligonucleotides ZDB3 (5'-CTAGCCCTTATTAATAATGAATCACAAAGTGGG-3') (SEQ ID NO: 37) with ZDB3' (5'-AATTCCCACTTTGTGATTCATTATTAATAAGGG-3') SEQ ID NO: 38) or ZDB4 (5'-CTAGAGGG-TATTAATAATGAATCACAAAGTGGG-3') (SEQ ID NO: 39) with ZDB4' (5'-AATTCCCACTTTGTG-ATTCATTATTAATACCCT-3') (SEQ ID NO: 40) were inserted at the XbaI-EcoRI sites of pINZ to construct pINZDB3 and pINZDB4, respectively.

cspI was amplified by PCR with synthetic oligonucleotide primers, 8188 (5'-aagaattcAACATTTACATCGCGGAA-3') (SEQ ID NO: 49) and 8187 (5'-tt gggatCCTCAAAGCGCCACTA-3') (SEQ ID NO: 50), where the 5' tails are shown in lowercase type and the EcoRI and BamHI sites, respectively, are underlined. Genomic DNA from prototype strain W3110 was used as a template. The PCR fragment was directly cloned into the SmaI site of pUC19, yielding pNWI2. To construct a plasmid that can express only the 5'-UTR of cspI but not its coding region, pNWI2 was digested with StyI and SacI, blunt ended with T4 DNA polymerase, and then self-ligated, yielding pNWI6.

To construct the transcriptional and translational cspI-lacZ fusions, PCR was first carried out with primers 8188 (see above) and 8010 (5'-ggg ggatccGGGTTAAACCATTTCACT-3') (SEQ ID NO: 51), where the 5' tail is shown in lowercase type and the BamHI site is underlined. The PCR fragment was digested with EcoRI and BamHI and then cloned into pRS414 for the construction of a translational fusion and into pRS415 for the construction of a transcriptional fusion, yielding pNWI3 and pNWI4, respectively. For the deletion construct of the entire 5' untranslated region of the cspI-lacZ fusion, PCR was carried out with primers 8188 (see above) and 8404 (5'-ggggatcCAGAACACCATTAACGC-3') (SEQ ID NO: 52), where the 5' tail is shown in lowercase type and the BamHI site is underlined. The PCR fragment was cloned into pRS415 in a similar way to that described above, yielding pNWI5. All the constructs were confirmed by DNA sequencing with Sequenase version 2.0 (Amersham).

β-Galactosidase Activity

E. coli AR137 (pcnB$^-$) (Harlocker et al., 1993) or JM83 (pcnB$^+$) harboring different plasmids were grown at 37° C. to mid-log phase in 20 ml of LB medium containing 50 mg/ml of ampicillin in a 125 ml flask. The cultures were then transformed to a 15° C. shaking water bath or isopropyl-β-D-thiogalactopyranoside (IPTG; 1 mM) was added to a final concentration of 1 mM. A 100 ml culture was taken at each time point. β-galactosidase activity was measured according to Miller's procedure (Miller, 1972).

The cspI-lacZ fusion constructs were introduced into strain AR134. Cells were grown in LB or M9 medium at 37° C. to mid-log phase and then transferred to 15° C. Portions of culture were taken immediately before the temperature downshift (0 h) and at 1, 2, 3, and 5 h after the temperature downshift. β-Galactosidase activity was measured as described in Miller, "A short course in bacterial genetics—a laboratory mammal and handbook for Escherichia coli and related bacteria," Cold Spring Harbor Laboratory Press, Cold Spring Harbor, N.Y. (which is incorporated by reference herein in its entirety). The assay was done at least in duplicate at each time point.

Example 2

Isolation of RNA, Primer Extension and Ribosome Analysis

E. coli AR137 harboring different plasmids was grown under the same conditions used for the β-galactosidase assay described above. In order to estimate the amount of cspA-lacZ mRNA, a 1.5-ml culture was taken at each time point and RNA was extracted by the hot-phenol method as described by Sarmientos et al., 1983.

For the mRNA stability experiments at 15° C., rifampicin was added at 1 hr after the temperature downshift at a final concentration of 200 μg/ml to stop transcription, and a 1.5-ml culture was taken at each time point. For the mRNA stability at 37° C., the culture was first shifted to 15° C. for 30 min to accumulate the mRNAs. Then, a 5-ml culture was taken and mixed with a 5 ml of the medium containing 400 μg/ml rifampicin in a glass flask kept in 37° C. shaking water bath. The medium was prewarmed at 60° C. Using this method, the culture temperature immediately changed to 32° C. and reached 37° C. within 1 min.

The cspA-lacZ mRNAs were detected by the primer extension method as described previously (Jiang et al. 1993) using a $^{32}$P-labeled primer M13-47, 5'-CGCCAGGGTTTTCCCAGTCACGAC-3' (SEQ ID NO: 41), which is complementary to a 5'-end coding sequence of lacZ. The products were separated on a denatured polyacrylamide gel (6%) and quantified by the use of Phosphorimager (BioRad).

Strain JM83 was grown in LB medium at 37° C. to mid-log phase and then transferred to 15° C. RNA was extracted from a 1.5-ml culture by the hot-phenol method described previously (1). Primer 8272 (5'-CCAAAACCTTTTTCAGGG-3') (SEQ ID NO: 53) for detection of cspI and primer 4593 (5'-ACATAGTGTATTACCTTTAA-3') (SEQ ID NO:54) for detection of cspA were labeled with [γ-32P]ATP (>5,000 Ci/mmol; DuPont-New England Nuclear) by using T4 polynucleotide kinase (Gibco BRL). Primer extension was carried out with 5 μg of RNA at 42° C. for 1 h in a final volume of 10 μl, which contained 50 mM Tris-HCl (pH 8.5), 8 mM MgCl2, 30 mM KCl, 1 mM dithiothreitol, 0.4 pmol of 32P-labeled primer, 0.5 mM dATP, 0.5 mM dGTP, 0.5 mM dCTP, 0.5 mM dTTP, 10 U of RNase inhibitor (Boehringer Mannheim), and 6.25 U of avian myeloblastosis virus reverse transcriptase (Boehringer Mannheim). Primer extension products were analyzed on a 6% polyacrylamide gel under denaturing conditions.

For measurement of the stability of mRNA at 15° C., rifampin was added 1 h after the temperature downshift to 15° C. at a final concentration of 200 μg/ml to stop transcription. For measurement of the stability of mRNA at 37° C., the culture was shifted to 15° C. for 30 min to accumulate mRNAs, a 5-ml sample was taken and mixed with 5 ml of the medium (which was prewarmed at 60° C.) in a glass flask kept at 37° C., rifampin was simultaneously added to a final concentration of 200 μg/ml, a 1.5-ml sample was taken at each time point, and RNA extraction and primer extension assays were done as described above. Primer extension products were quantitated by using a phosphorimager (Bio-Rad).

Pulse Labeling

Cultures of E. coli AR137 (pcnB$^-$) cells carrying pINZ or pINZDB1 were grown at 37° C. under the same conditions used for the β-galactosidase assay. IPTG (1 mM) was added at mid-log phase to each culture. At each time point, 1 ml of the culture was labeled for 5 min with 100 mCi of trans-[$^{35}$S]methionine (1,175 Ci/mmol) (NEN Life Science Products) as described previously (Jones et al., 1996). Cell extracts from each time point were loaded on a 5% SDS-PAGE and β-galactosidase synthesis was measured by phosphorimager.

Cells were grown in M9 medium supplemented with glucose, 19 amino acids (no methionine), and thiamine at 37° C., and then transferred to an indicated temperature. Cells were labeled with [$^{35}$S]methionine (1092 Ci/mmol; Amersham) for 30 min at lower temperatures and then chased for 5 min by adding nonradioactive methionine to a final concentration of 0.2 M. Cell lysates were prepared and processed by two-dimensional gel electrophoresis as described previously.

Ribosome Isolation

Cultures of E. coli JM83 (pcnB$^+$) cells carrying pINZ or pINZDB1 were grown in 600 ml of LB medium in a 4-liter flask under the same condition as described above. At mid-log phase IPTG (1 mM) was added to each culture. Ribosomal particles were isolated by the procedure described by Dammel and Noller (1995), with some modifications: An 100-ml aliquot from the original culture was taken at each time point and chloramphenicol was added to a final concentration of 0.1 mg/ml to stop cell growth. Cells were immediately collected by centrifugation (5,000×g for 10 min at 4° C.), resuspended in buffer 1 [20 mM Tris-HCl (pH 7.6), 10 mM MgCl$_2$, 100 mM NH$_4$Cl, 6 mM β-mercaptoethanol and 1 mg/ml lysozyme] and frozen at −80° C. for few hours. The cells were lysed by the freeze-thaw method (Ron et al. 1996). The cell extracts (0.5 ml) were then layered on top of a 5–40% (w/w) sucrose gradient (7.5 ml) and the polysomes and ribosomal subunits were separated by centrifugation at 151,000×g for 2.5 hr at 4° C. using a Beckman SW-41 rotor. The polysome profiles were detected by a FPLC system and a total of 15 fractions of 0.5 ml each were collected.

Detection of the lacZ-mRNA

From each polysome fraction (0.5 ml) 0.2 ml was spotted on a Nitrocellulose membrane using the Minifold® II Slot-Blot System (Schleicher and Schuell). The lacZ-mRNA was detected by hybridization using the [$^{32}$P]-labeled M13-47 primer (S. Inouye and M. Inouye, 1991) and the amount of lacZ-mRNA was estimated by phosphorimager.

In Vitro Translation

Using the E. coli S30 Extract System for Linear Templates Kit (Promega), the transcription-translation coupled reaction was carried out according to the manufacturer's protocol as follows; To 20 ml of Pre-mix containing all the amino acids except for methionine, 10 mCi of trans-[$^{35}$S] methionine (1,175 Ci/mmol; NEN Life Science Products) and the E. coli S30 extracts, 160 ng of pINZ or pINZDB1 (1 ml) was added and the mixture was incubated at 37° C. for 45 min. The products were precipitated with acetone and analyzed by 15% SDS-PAGE.

Example 3

Multicopy Effects of the cspA Upstream Region on Cold-shock Adaptation

It has been shown that the cspA gene is induced immediately after the temperature downshift from 37° C. to either 15 or 10° C. and that the rate of cspA production reaches a peak after 1 hr at 15° C. and 2 hr at 10° C. after the temperature shift (Goldstein et al., 1990). After this time point, cspA production sharply drops to a new basal level. The period of this transient production of cspA corresponds to the duration of growth arrest, known as the lag period, which is observed after cold shock (Jones et al., 1987). Thus, such a transient expression of cspA is considered to be required for cellular adaptation to lower temperatures.

Figure 1A:
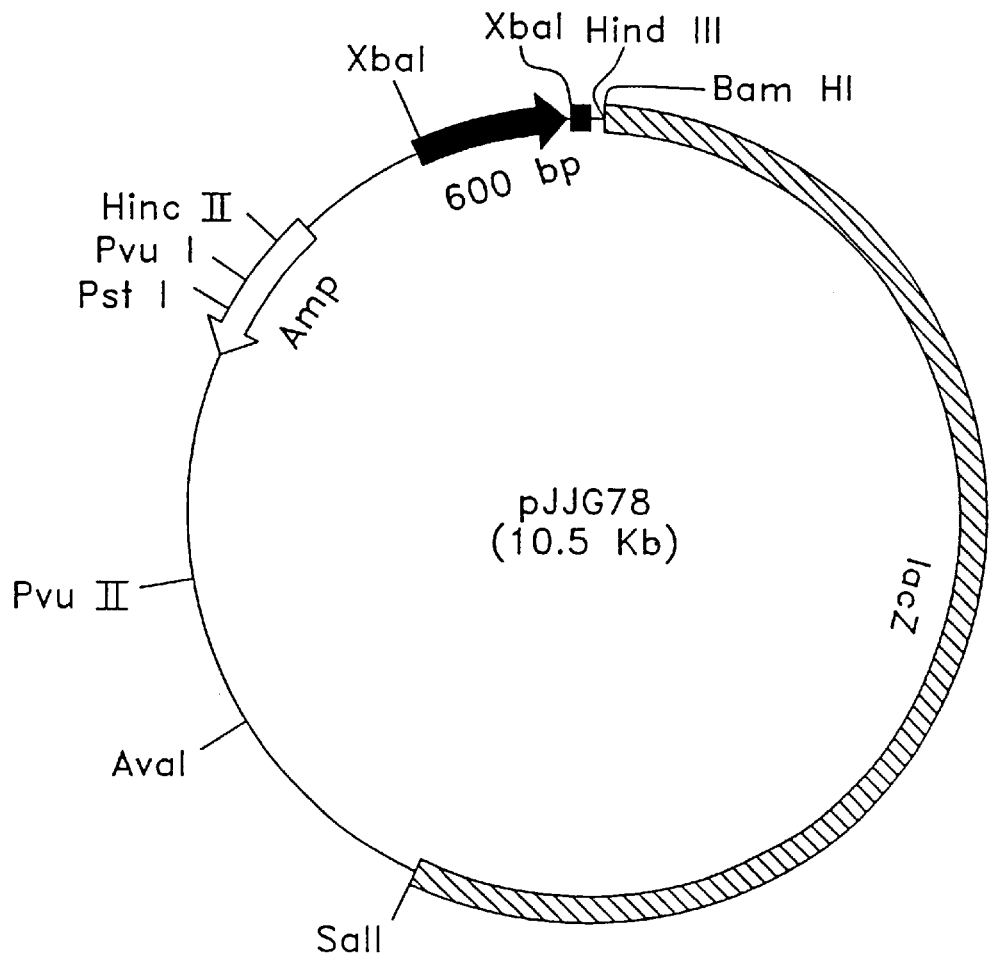
FIGS. 1A and 1B show the plasmid pJJG78 and the effects of the cspA upstream region on the chromosomal cspA expression and the synthesis of other cellular proteins: (A) pJJG78. (B) the effects of the cspA upstream region on the chromosomal cspA expression and the synthesis of other cellular proteins.
Figure 1B:
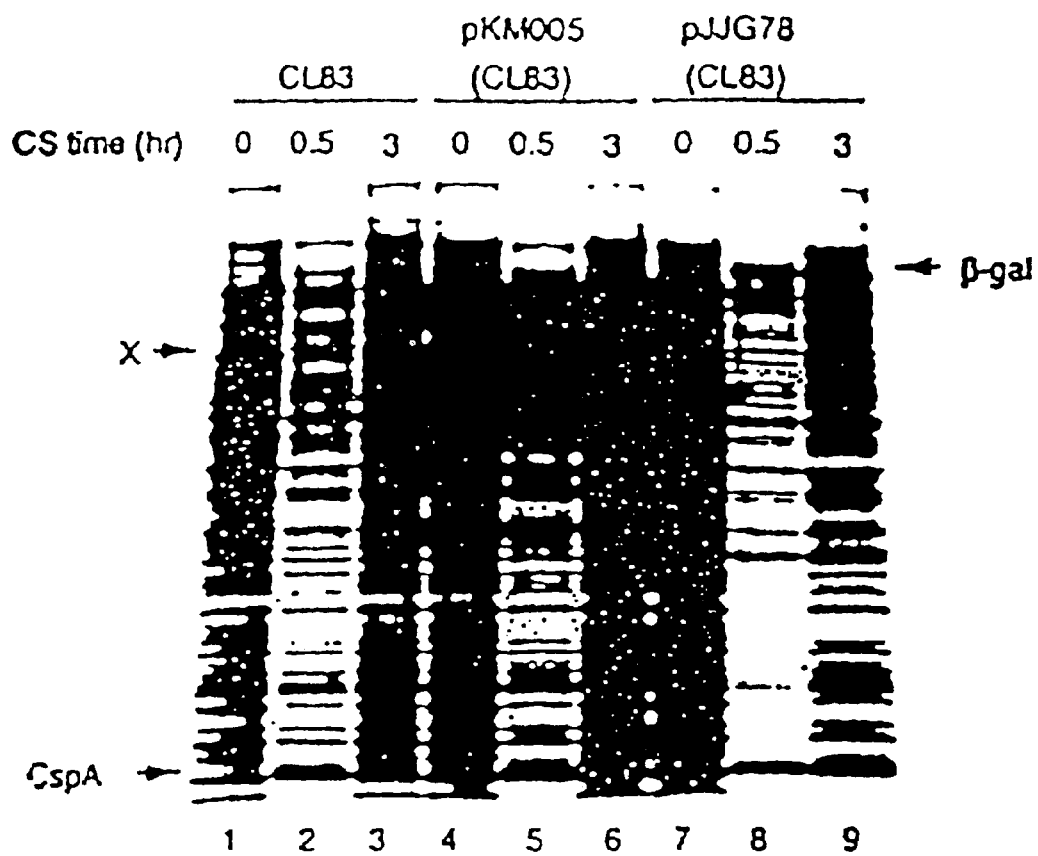

In order to characterize this transient expression of cspA, we attempted to identify the region required for the regulation of the cspA expression during the adaptation period. For this purpose, pJJG78 was first constructed, in which the 600-bp cspA upstream region was transcriptionally fused to the lacZ gene (FIG. 1A). This 600-bp upstream region of cspA encompasses the region from −457 to +143 which is right before the Shine-Dalgarno sequence of cspA, as the cspA transcription initiation site is defined +1 (Goldstein et al., 1990). E. coli strain CL83 was transformed with pJJG78 and the production of β-galactosidase was examined by pulse-labeling cells with [$^5$S]-methionine at 0, 0.5, and 3 hr after temperature downshift from 37 to 15° C. As controls, CL83 cells alone as well as CL83 cells transformed with vector pKM005 (Inouye 1983) were also used. As shown in FIG. 1B, for both CL83 and CL83/pKM005 the expression of cspA was highly induced at 0.5 hr after the temperature downshift (FIG. 1B, lanes 2 and 5, respectively). However, as shown previously (Goldstein et al., 1990), this high expression is transient and reduced to a new basal level at 3 hr (FIG. 1B, lanes 3 and 6, respectively). Note that no cspA expression was detected at 0 time point (FIG. 1B, lanes 1 and 4, respectively) and that β-galactosidase was not produced at any time point for both strains (FIG. 1B, lanes 1 to 6).

In contrast to CL83 and CL83/pKM005, β-galactosidase was clearly induced in the cells with pJJG78 upon the temperature downshift (FIG. 1B, lanes 7 to 9), indicating that the 600-bp upstream region of cspA is sufficient for the cold-shock induction. Surprisingly, the production of cspA was no longer transient but remained at a high level even 3 hr after cold shock in the cells harboring pJJG78 (FIG. 1B, compare lane 9 with lanes 3 and 6). Since pJJG78 does not contain the cspA coding sequence, the high production of cspA at 3 hr after temperature downshift is attributed to the chromosomal cspA gene. It appears that under the conditions used, the chromosomal cspA gene failed to be repressed, in other words it became derepressed. Interestingly, there is another band indicated by X in FIG. 1B, whose expression pattern was almost identical to that of cspA. It is a cold-shock protein and its production was also derepressed in the presence of pJJG78. This cold-shock protein X has been recently identified as CsdA which associates with ribosomes (Jones et al., 1994).

It should also be noted that the synthesis of most cellular proteins was blocked to a larger extent in the cells harboring pJJG78 at low temperature than that in the CL83 cells and CL83/pKM005 (FIG. 1B, compare lanes 8 and 9 to lanes 2, 3, 5, and 6). These results indicate that the cellular adaptation to the low temperature is impaired with a more severe cold-shock response when cells harbor a multicopy plasmid carrying a part of the cspA gene.

Figure 2:
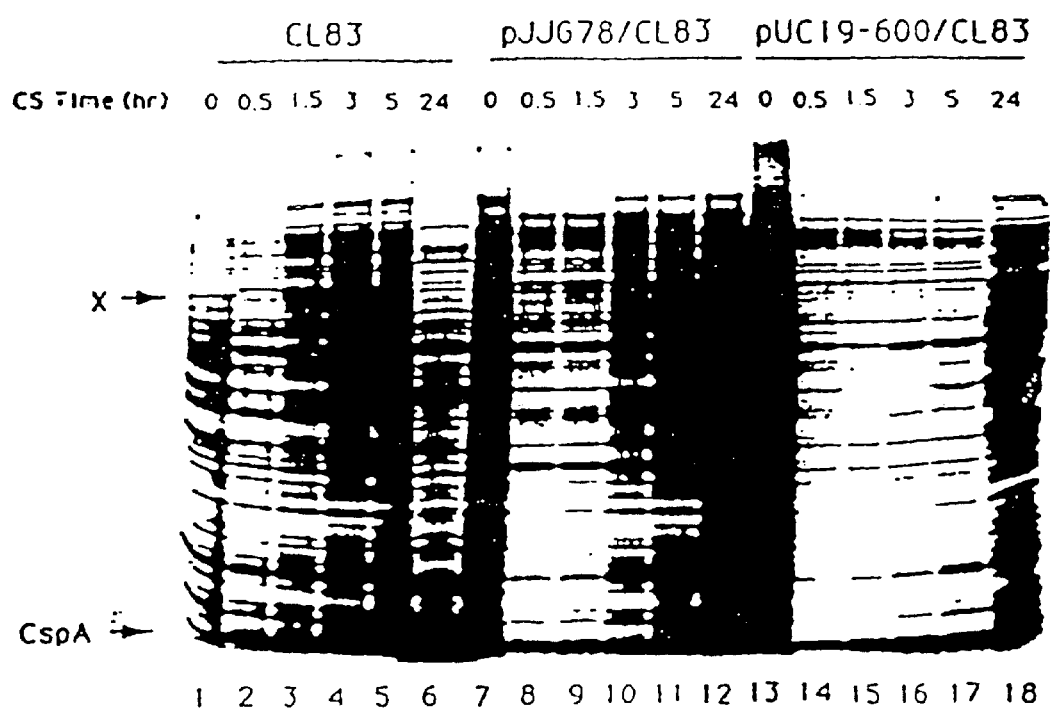
FIG. 2 shows the prolonged expression of CspA and inhibition of cold-shock adaptation by pJJG78 and pUC19-600.

Since the prolonged synthesis of cspA after cold shock was caused by pJJG78, it was hypothesized that the 600-bp cspA upstream region cloned in pJJG78 may sequester a factor responsible for the inhibition of cspA production after cold shock, resulting in the prolonged expression or the derepression of cspA. In order to examine this hypothesis, the 600-bp upstream region of cspA was re-cloned into pUC19. The plasmid is called pUC19-600. Note that the copy number of pUC19 (300 copies/cell) is about 10 times higher than pJJG78 derived from pBR322 (30 copies/cell). A pulse-labeling experiment was carried out as described previously (Jiang et al., 1993). As shown in FIG. 2, in the CL83 cells, cspA production increased up to 1.5 hr and was reduced to a basal level after 3 hr at 15° C. (FIG. 2, lanes 1 to 6). In CL83 cells with pJJG78, a certain level of cspA expression was still observed even after 24 hr at 15° C. (FIG. 2, lanes 7 to 12). Patterns of cspA production in CL83 cells with pUC19-600 are similar to those with pJJG78 (FIG. 2, lanes 13 to 18). However, the level of the cspA derepression was much higher with pUC19-600 than that with pJJG78, as judged from the production of cspA at 3 and 5 hr. Thus, the higher the copy number of the cspA upstream region, the stronger the derepression of the cspA expression. Again, CsdA (indicated by X) showed the exactly same expression pattern as cspA throughout all the lanes shown in FIG. 2.

As shown in FIG. 1B, the cells with pJJG78 showed a certain inhibition of general protein synthesis at low temperature (compare lanes 8 to 11 with lanes 2 to 5, respectively in FIG. 2). Significantly, this inhibition in the cells harboring pUC19-600 was even more evident than that in the cells harboring pJJG78, in terms of both the protein synthesis rate and the inhibition time (compare lanes 14 to 17 with lanes 8 to 11, FIG. 2). The higher copy number of the 600-bp of cspA upstream region results in the stronger inhibition of the synthesis of other cellular proteins, indicating that cold-shock adaptation is inhibited.

Example 4

Overproduction of the 5' Untranslated Region of the cspA mRNA

Figure 3:
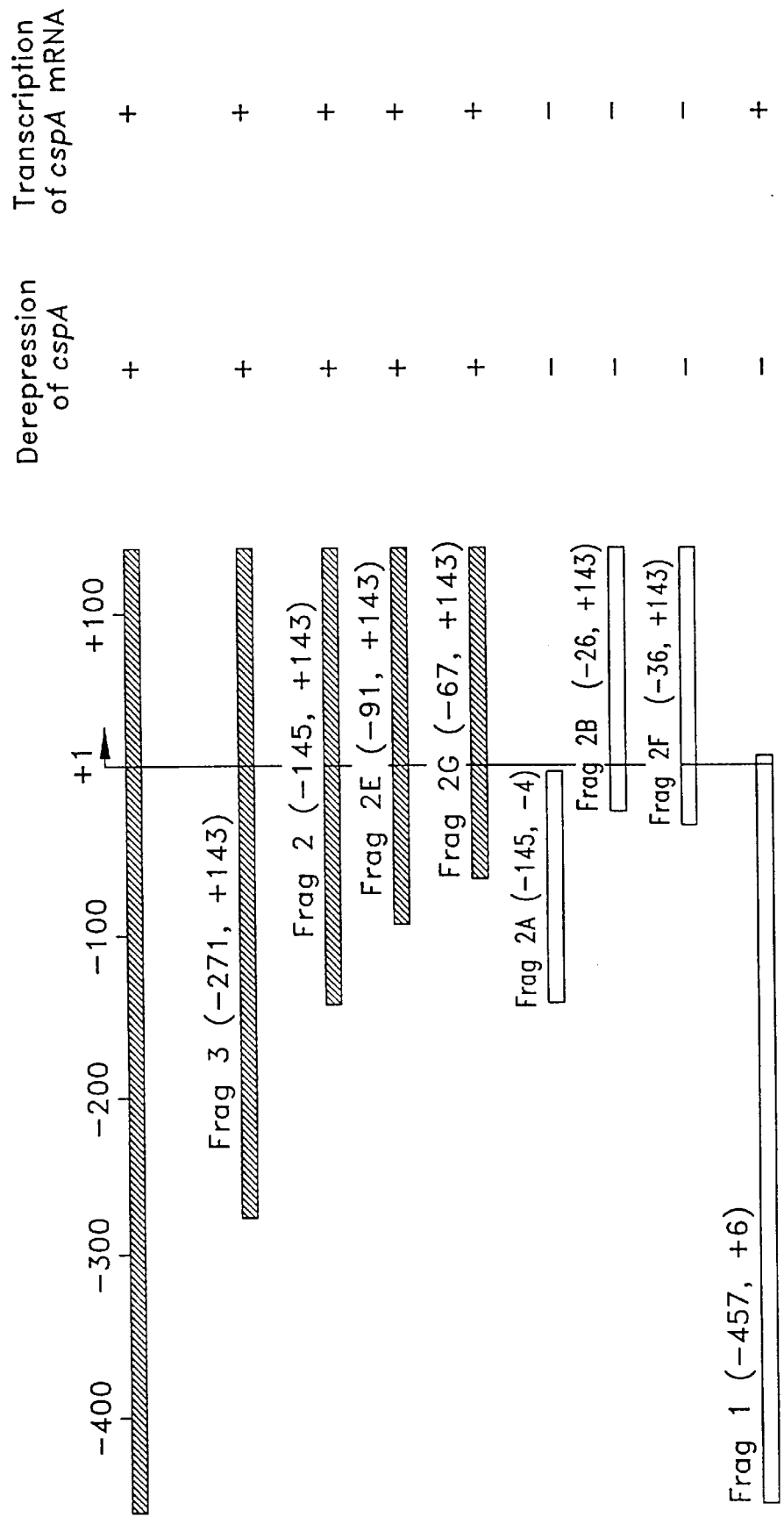
FIG. 3 shows deletion analysis of the cspA upstream region for the cspA derepression function and inhibition of cold shock adaptation.

In order to determine the precise region within the 600-bp sequence required for the derepression of cspA and the inhibition of cold-shock adaptation at low temperature, a series of internal fragments as shown in FIG. 3 were generated by PCR and cloned into the SmaI site of pUC19. Their sequences were confirmed by DNA sequencing. The ability to derepress expression of cspA and to inhibit cold-shock adaptation at 15° C. for each construct was examined by pulse-labeling experiment. First, deletion mutations were made from the 5' end of the 600-bp fragment. As shown in FIG. 3, fragment 3 (186-base deletion), fragment 2 (312-base deletion), fragment 2E (366-base deletion) and fragment 2G (390-base deletion) all still retained the derepression function. Next, fragment 2 was further dissected into fragment 2A and 2B which overlap by 23 bp as shown in FIG. 3. Surprisingly, both 2A and 2B lost the functions. Fragment 2F which is longer by 33 bp at the 5' end than fragment 2B was also constructed, was still incapable of the functions. It was found here that the constructs which are capable of the derepression of cspA also result in inhibition of the cold-shock adaptation, and vice versa.

The fact that fragment 2 is functional for both the cspA derepression and the inhibition of cold-shock adaptation, while fragment 2A is not, indicates that the cspA promoter region alone is not sufficient for the functions of the 600-bp fragment. Furthermore, the fact that functional fragment 2G is longer at the 5' end by 31 bp than the non-functional fragment 2F suggests a possibility that the both functions require the full cspA promoter for the transcription of the 5' UTR of the cspA mRNA. Note that the cspA mRNA has a 159-base untranslated sequence at the 5' end (Goldstein et al., 1990). In order to confirm this possibility, the cspA transcripts produced from the cloned fragments (fragments 2, 2A, 2B, 2E, and 2F) were examined by primer extension. Using the total RNA fraction isolated from cells harboring various plasmids incubated for 1 hr at 15° C., primer extension was performed with two independent primers; primer 3550 which corresponds to the sequence from +124 to +143 in the 5' UTR and primer 3551 which corresponds to a part of the cspA coding sequence from +224 to +243. The former primer detects the cspA mRNA transcribed from both the plasmid and the chromosome, while the latter detects the mRNA only from the chromosomal cspA gene, since none of the plasmids contains the cspA coding region.

Figure 4:
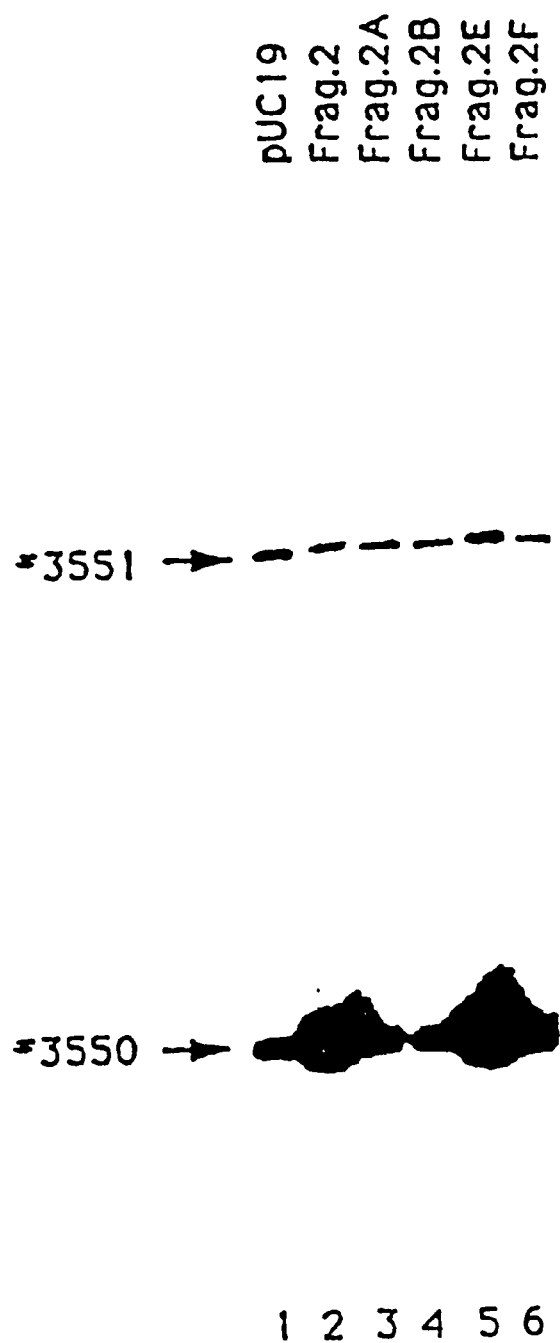
FIG. 4 shows the level of transcripts from the chromosomal and plasmid cspA.

As shown in FIG. 4, the amounts of the transcript from the chromosomal cspA gene indicated by primer 3551 were basically the same among all constructs (FIG. 4, lanes 1 to 6). In contrast, the amount of the cspA transcripts encompassing the 5' UTR indicated by primer 3550 showed two different levels. For those unfunctional constructs (pUC19-2A, pUC19-2B, and pUC-2F), the amounts of the transcripts detected by primer 3550 (lanes 3, 4, and 6 in FIG. 4, respectively) were almost identical to that with pUC19 (lane 1 in FIG. 4), indicating that the cspA regions cloned in these plasmids were not transcribed. On the other hand, for those functional constructs (pUC19-2 and pUC19-2E), much higher levels of the cspA transcripts detected by primer 3550 were observed (lanes 2 and 5 in FIG. 4, respectively) in comparison with the level with pUC19 (lane 1 in FIG. 4). These results demonstrate that the 5' UTR of the spA mRNA was transcribed in fragment 2 and 2E, but not in fragments 2A, 2B and 2F. Therefore, the ability to prolong cspA expression and to inhibit the cold-shock adaptation at low temperature is clearly correlated with the transcription of the 5' UTR of the cspA mRNA.

Figure 5B:
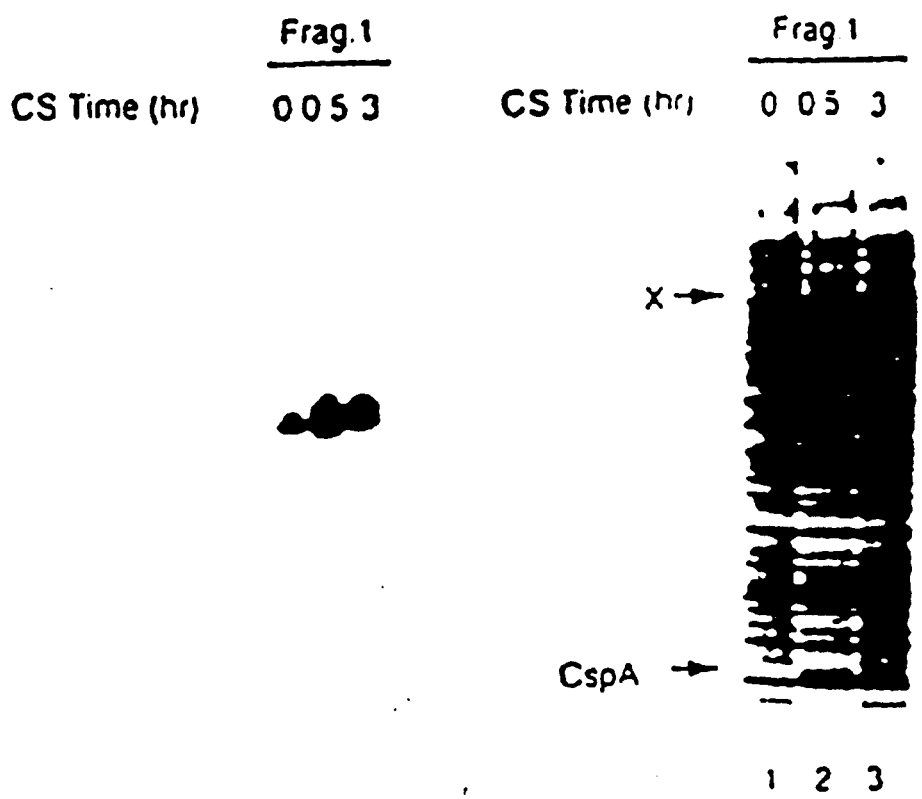
FIGS. 5A and 5B show the requirement for the transcription of the 5' untranslated region of the cspA mRNA for the prolonged expression of cspA and inhibition of cold-shock adaptation.
Figure 5A:

In order to unambiguously demonstrate that the transcription of the 5' UTR of the cspA mRNA is required for both the cspA derepression and the inhibition of cold-shock adaptation, the entire promoter fragment (−457 to −1) plus 6-base (+1 to +6) region from cspA was cloned into pUC19. This fragment was designated fragment 1 (see FIG. 3). Thus, most of the 5' UTR of the cspA mRNA was deleted in fragment 1. By pulse-labeling experiment shown in FIG. 5B, fragment 1 was incapable of derepressing cspA, in spite of the fact that the transcripts from the cspA promoter were clearly detectable by primer extension (FIG. 5A). From these results, it is concluded that at least a portion of the cspA untranslated region from +1 to +143 has to be transcribed to exert the effect on the cspA expression and the cold-shock adaptation.

Example 5

Cold-shock Genes Affected by the Overproduction of the 5' UTR of the cspA mRNA

Next the overproduction of the 5' UTR of the cspA mRNA was examined to determine if the cspA mRNA has any effects on the expression of other cold-shock genes. The protein expression pattern of the cold-shocked cells overproducing the cspA 5' UTR was analyzed by two-dimensional electrophoresis. The plasmid pJJG21/X,S contains the entire cspA promoter and most of the 5' UTR of the cspA mRNA (+1 to +143), while pJJG81/X,S contains the entire cspA promoter but only the first 6-base region of the cspA untranslated mRNA. The cells harboring these plasmids were pulse-labeled as described before (Jiang et al., 1993). At 37° C., the rate of protein synthesis and the protein pattern were very similar for both strains (FIGS. 6, A and B); note that no cold-shock proteins were detected. When these cells were shifted to 15° C. for 1 hr (FIGS. 6, C and D), the synthesis of cold-shock proteins (1. cspA; 2. CspB'; 3. CspB; and 4. CsdA) became very prominent. Note that CspB' was co-induced with CspB and has been speculated to be either a modified form of CspB or a yet unidentified cold-shock protein (Etchegaray et al., 1996). The rate of cold-shock protein synthesis for both constructs was comparable as judged from the densities of the spots. Although the synthesis of most other cellular proteins was significantly reduced for both strains compared with that at 37° C., much stronger inhibitory effects were observed in the cells transformed with pJJG21/X,S. When cells were incubated at 15° C. for 3 hr, synthesis of most cellular proteins recovered to a normal level with concomitant reduction of all the cold-shock proteins in the cells harboring pJJG81/X,S (FIG. 6F). In contrast, for the cells harboring pJJG21/X,S, the production of all the cold-shock proteins (marked by 1 to 4) was still maintained at a very high level along with reduced production of other cellular proteins (FIG. 6E). These results clearly demonstrated that overproduction of the 5' UTR of the cspA mRNA results in the derepression of not only cspA but also other cold-shock genes, suggesting that genes for cold-shock proteins are regulated by a common mechanism. It is also further confirmed that the inhibition of cold-shock adaptation is due to the overproduction of 5' UTR of the cspA mRNA by blocking the synthesis of other cellular proteins.

Based on the results described above, overproduction of the UTR of the cspA mRNA causes the concomitant inhibition of other cellular proteins. This implies that cell growth upon cold shock would be more severely inhibited with the cells overproducing the UTR of the cspA mRNA than that with the wild type cells. The growth of cells harboring pUC19-600 or pUC19-2G (see FIG. 3) was indeed severely inhibited. This was characterized by a longer lag period (data not shown).

Example 6

Effects of the Overproduction of cspA

Figure 7:
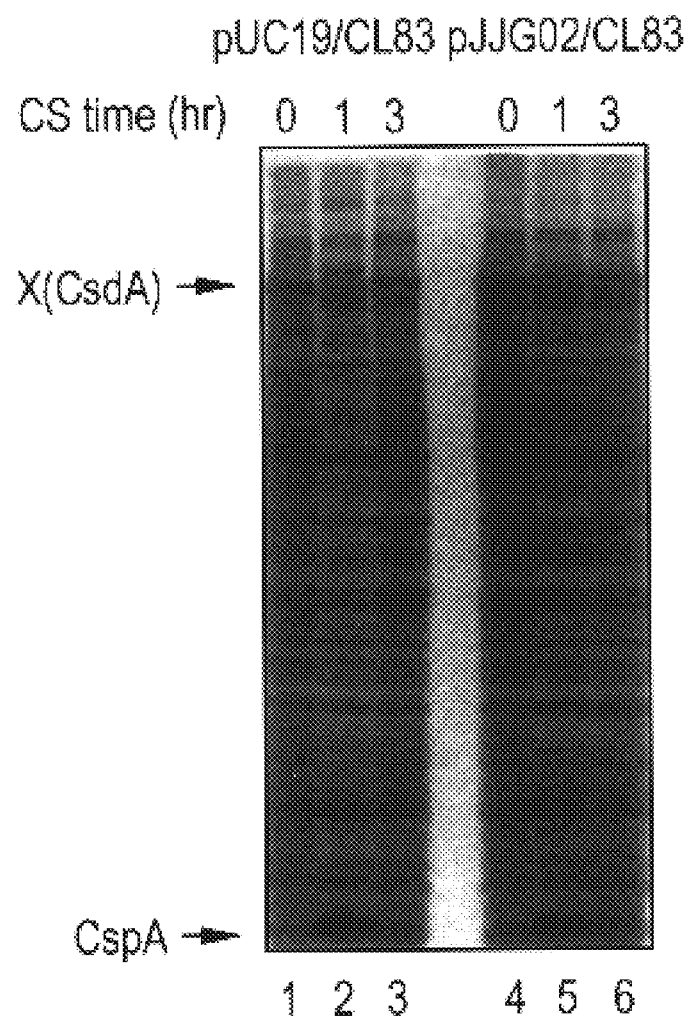
FIG. 7 shows the effects of co-overproduction of cspA together with the 5' untranslated region of the cspA mRNA on the cold-shock response.

The hyper-expression of the 5' UTR of the cspA mRNA resulted in the prolonged overproduction of cspA (see FIG. 2). Therefore, the effects observed above may be due to the overproduction of the CspA protein rather than the 5' UTR of the cspA mRNA. This possibility was examined using CL83 cells harboring pJJG02 which contains the entire cspA gene. Pulse-labeling experiments were carried out as described above. As shown in FIG. 7, with strain CL83 carrying pUC19, the expression of cspA and csdA (the gene for protein X) were induced at 1 hr after the temperature shift to 15° C. (lanes 1 and 2), and returned to a basal level at 3 hr after the temperature shift (lane 3). On the other hand, when the cells were transformed with pJJG02, the expression of cspA was not only induced at 15° C., but also significantly higher than that of cells with pUC19 as judged by two-dimensional gel electrophoresis (not shown). It should be noted that high cspA production is still observed even at 3 hr 15° C. (lane 6). Although this overproduction of cspA at 3 hr after cold-shock was very similar to the case with the overproduction of the 5' UTR of cspA as described earlier (FIG. 2), it is important to note that no prolonged lag period of cell growth and no prolonged production of other cold-shock proteins such as CspB and CsdA were observed at the same time point. These results indicate that the co-production of cspA with the 5' UTR of the cspA mRNA suppresses the effects of the overproduction of only the 5' UTR, and that the high levels of cspA production even at 3 hr after cold-shock are not the cause of this effect.

Example 7

Identification of a Repressor Binding Site

We attempted to identify the specific region responsible for the cspA derepression within the 5' UTR of cspA mRNA. Because of the 11-base sequence commonly found in the 5' UTR in cspA, cspB and csdA, the region containing this sequence from position +1 to +25 of the cspA 5' untranslated mRNA was tested. This region was put under the control of the cspA promoter in pUC19 to construct p2JTEK (FIG. 8). Cells harboring p2JTEK were then examined for the pattern of total protein synthesis at 3 hr after the temperature shift from 37 to 15° C. As shown in lane 3 in FIG. 8, CspA and CsdA production was clearly derepressed, with concomitant inhibition of other cellular proteins, as evident from the lighter background in comparison with cells harboring pUC19 (FIG. 8, lane 1). Cells harboring p6mTEK, which transcribes only the region from +1 to +6 of the cspA mRNA showed a pattern (FIG. 8, lane 2) identical to that of cells with pUC19 (FIG. 8, lane 1). This result indicates that the region responsible for the cspA derepression resides within the first 25-base sequence of the 5' UTR of cspA mRNA.

Example 8

Deletion Analysis of the cspA 5'-UTR

Previously, we constructed two cspA-lacZ fusions in which the lacZ gene was transcriptionally fused to cspA at +26 (pKM67; Mitta et al., 1997) or at +143 (pJJG78; Jiang et al., 1996) of the cspA mRNA. The β-galactosidase activity of the cells harboring pJJG78 was very low at 37° C., and increased about 10 fold at 2 h after temperature downshift to 15° C., whereas the β-galactosidase activity of the cells harboring pKM67 was very high even at 37° C. (Mitta et al., 1997). It has been proposed that the region from +26 to +143 in the 5'-UTR of cspA mRNA has three possible functions on cold-shock induction: (I) repression of cspA expression at 37° C., (ii) stabilization of its mRNA upon cold shock, and (iii) translation efficiency at 15° C. (Mitta et al., 1997).

Figure 9A:
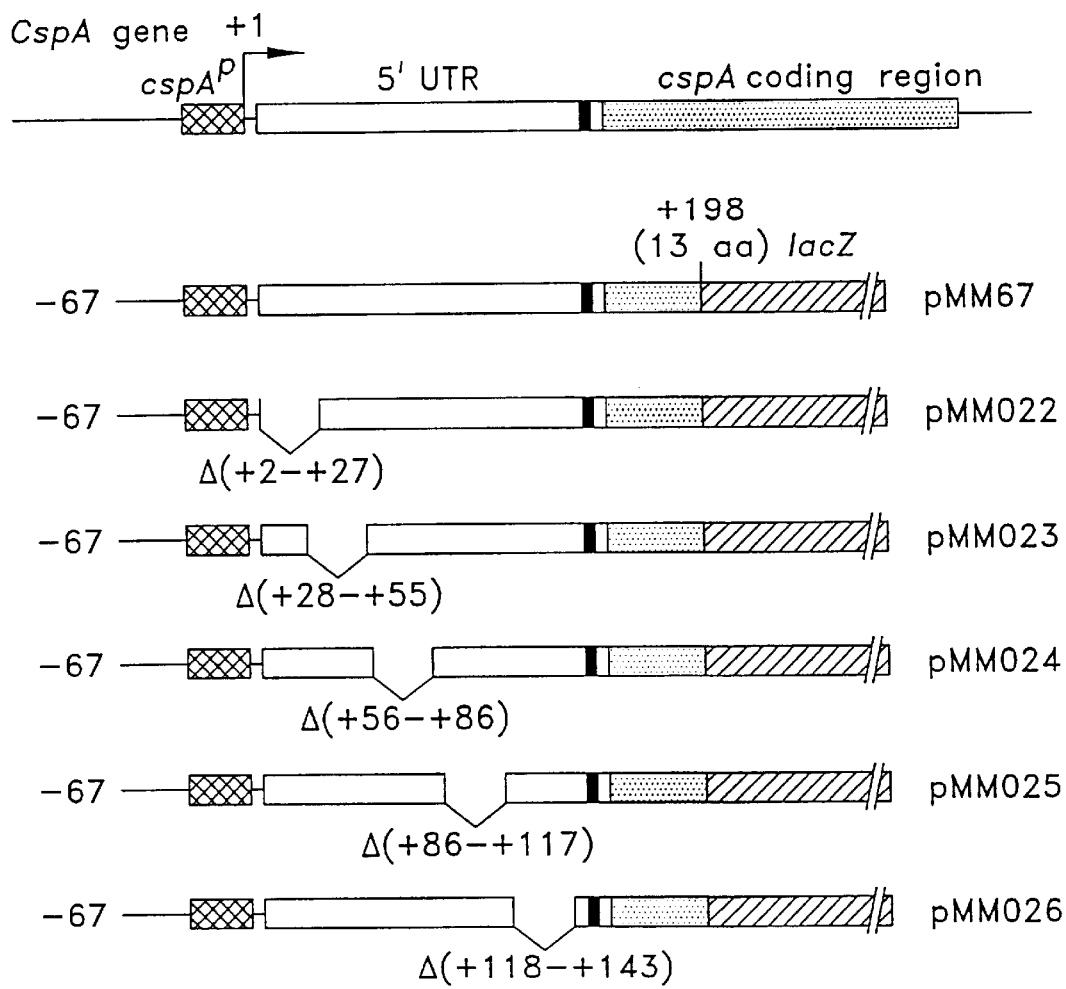
FIGS. 9A and 9B show cold-shock induction of β-galactosidase: (A) Construction of cspA-lacZ fusions. The wild-type cspA is shown on the top. The cspA-lacZ fusion in each expression plasmid is shown from the 5' end of the cspA promoter upstream region to lacZ. Nucleotide numbers are given starting from the transcription initiation site as +1, determined by Tanabe et al., 1992. The crossed hatched, open, dotted and slashed bars represent the cspA promoter, its 5' untranslated region, the cspA coding region and the lacZ coding region, respectively. The solid boxes indicate the SD sequence. The positions of deleted regions are shown with nucleotide numbers. (B) Induction patterns of various deletion constructs. At mid-log phase, cultures of E. coli AR137 harboring various plasmids were shifted from 37° C. to 15° C. Samples were taken at 0, 1, 2, 3, 5, 7 and 10 h after the shift and β-galactosidase activity was measured. The cspA-lacZ fusions: pMM67 (○); pMM022 (●); pMM023 (□); pMM024 (■); pMM025 (Δ); and pMM026 (▼).

In order to further investigate which part of the 5'-UTR is responsible for the positive or negative regulation of cspA expression, we attempted deletion analysis of the 5'-UTR and examined the effect of various deletions on cold-shock induction of cspA. For this purpose, a series of 5'-UTR deletion mutants were constructed, in which a 26- to 32-base deletion was created at every about 30 bases, and the resultant 5'-UTR was translationally fused to lacZ at the 13th amino acid residue of CspA. The resultant plasmids, pMM022, pMM023, pMM024, pMM025 and pMM026 contain deletion mutations in the 5'-UTR from +2 to +27, from +28 to +55, from +56 to +86, from +86 to +117, and from +118 to +143, respectively (FIG. 9A). In the case of pMM024, a deletion from +56 to +85 was originally designed, but all the transformants we analyzed contained an extra base deletion at position +86. Plasmid pMM67 (Mitta et al., 1997), which is the wild-type cspA-lacZ translational fusion construct, was used as a control. *E. coli* AR137, apcnB mutant, which is known to maintain pBR322 derivatives in a low copy number (Lopilato et al., 1986), was used as a host for transformation in order to avoid multicopy effects of the constructed gene on their expression.

Figure 9B:
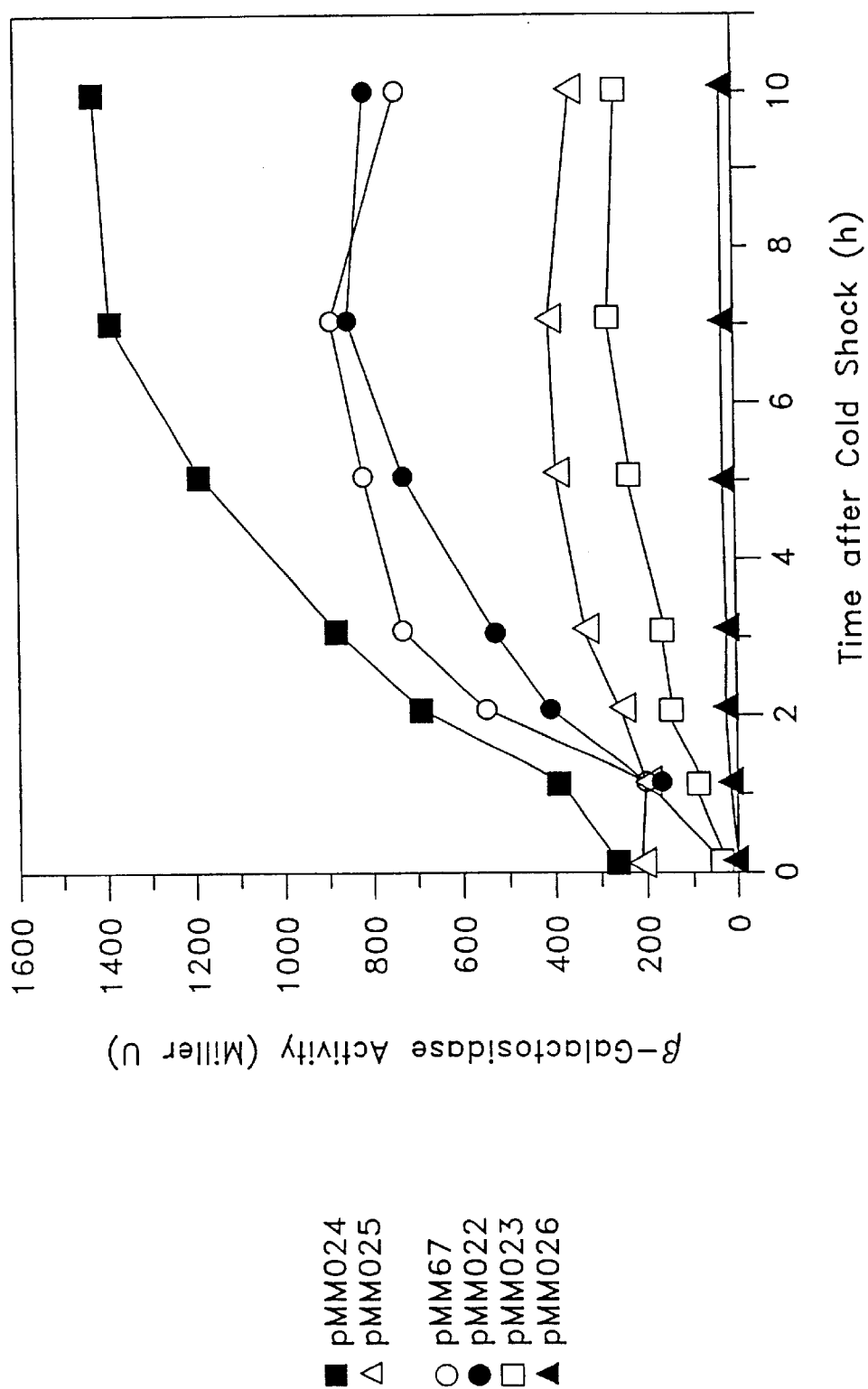

Transformed cells were grown in M9-Casamino acids medium at 37° C., and β-galactosidase activities were measured after temperature downshift from 37° C. to 15° C. At 37° C. (zero time point in FIG. 9B), β-galactosidase activities were 10 fold higher in cells harboring pMM024 (Δ56-86) and pMM025 (Δ86-117) than in cells harboring the wild-type pMM67, while other deletion mutants [pMM022 (Δ2-27), pMM023 (Δ28-55) and pMM026 (Δ118-143)] showed very low β-galactosidase activities. These results suggest that the 5'-UTR region from base +56 to +117 is involved in the repression of cspA expression at 37° C. Interestingly β-galactosidase activity increased almost 5 fold with pMM024 (Δ56-86) after temperature downshift, while it increased only less than 2 fold with pMM025 (Δ86-117), suggesting that the region deleted in pMM025 (Δ86-117) plays an important role in cold-shock induction of cspA. Similar to pMM025 (Δ86-117), β-galactosidase activity with pMM023 (Δ28-55) was poorly induced at low temperature. In particular, the region deleted in pMM026 (Δ118-143) appears to play a crucial role in cspA expression at both high and low temperatures, since β-galactosidase activity was very low at both 37° C. and 15° C. (FIG. 9B). The deletion of the region from base +2 to +27 (pMM022) containing the cold-box sequence involved in cspA autoregulation (Jiang et al., 1996) has little effect on the cold-shock induction of cspA as predicted (FIG. 9B).

Example 9

Analyses of cspA-lacZ mRNA

Figure 10A:
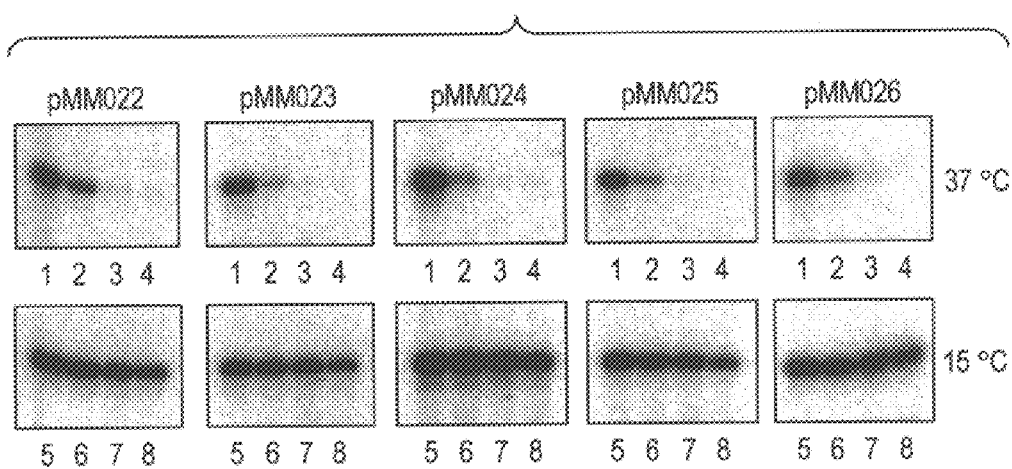
FIGS. 10A–10C show the analysis of the mRNA stability. (A) Primer extension analysis of the cells harboring the cspA-lacZ fusions. At mid-log phase, cultures of E. coli AR137 harboring various plasmids were shifted from 37° C. to 15° C. For measurement of the mRNA stability at 37° C., cultures were shifted back to 37° C. after 30 min incubation at 15° C. and rifampicin was added to the cultures to a final concentration of 200 µg/ml. RNAs were extracted at 0 (lane 1), 1 (lane 2), 3 (lane 3) and 5 min (lane 4) after the addition of rifampicin. For measurement of the mRNA stability at 15° C., rifampicin was added 1 h after the temperature downshift, and then RNAs were extracted at 0 (lane 5), 5 (lane 6), 10 (lane 7), and 20 min (lane 8) after the addition of rifampicin. Primer extension was carried out. (B) Graphical presentation of the results shown in (A) for 37° C. and 15° C., respectively. The radioactivities of transcripts were measured using a Phosphorimager and plotted using the transcript at zero time point as 100%: pMM022 (●); pMM023 (□); pMM024 (■); pMM025 (Δ); and pMM026 (▲).
Figure 10C:
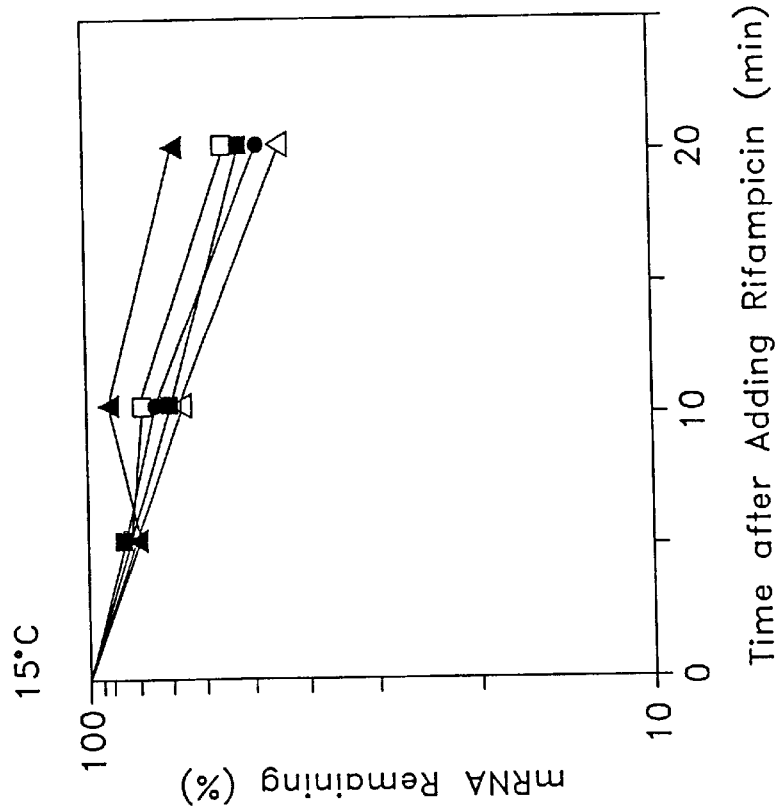
Figure 10B:
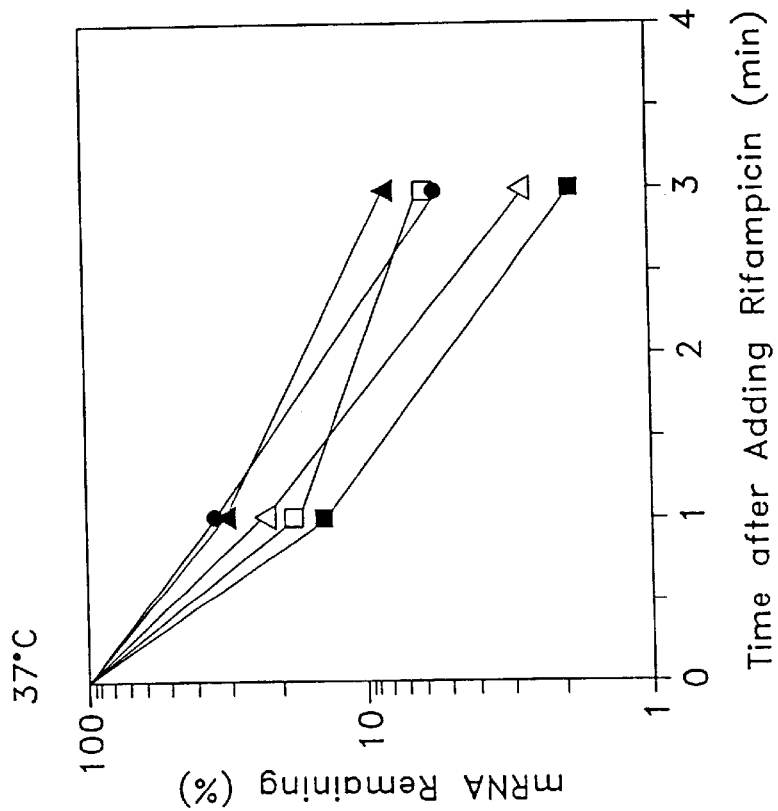

As described above, all deletion mutations of the 5'-UTR except for pMM022 (Δ2-27) affected on cold-shock induction of cspA. The cspA promoter is known to be active even at 37° C. (Goldenberg et al., 1997; Fang et al., 1997; Mitta et al., 1997). Since all the deletion constructs have the intact cspA promoter (FIG. 9A), transcription efficiencies of these constructs are likely to be identical. On the other hand, the cspA mRNA stability is significantly different depending on growth temperatures (Brandi et al., 1996; Goldenberg et al., 1996; Bae et al., 1997; Fang et al., 1997; Goldenberg et al., 1997; Mitta et al., 1997). Therefore the effect of the deletion mutations on the cspA expression at low temperature may be due to different mRNA stabilities of the constructs. To examine this aspect, the primer extension analysis was carried out to quantitate the amounts of the cspA-lacZ transcripts for each mutant at different time points after the addition of rifampicin at both 37° C. and 15° C. (FIG. 10A). Again, in order to avoid multicopy effects either positively or negatively, strain AR137, a pcnB mutant, was used. The amounts of transcripts at each time point were estimated by a phosphorimager, and the amounts of mRNA remained (per cent of the amount at zero time point) were plotted as shown in FIG. 10B. All the transcripts were unstable at 37° C. with their half-lives estimated between 30 and 45 s. At 15° C., however, they became very stable with half-lives between 20 and 40 min. These half-lives are similar to those for the wild-type construct pMM67 obtained previously (Mitta et al., 1997) as well as to those for the wild-type chromosomal cspA (Fang et al., 1997; Goldenberg et al., 1997). It is important to note that in contrast to the similar mRNA half-lives at low temperature, β-galactosidase activities induced at 15° C. were widely varied among all these constructs as shown in FIG. 9B.

Figure 11A:
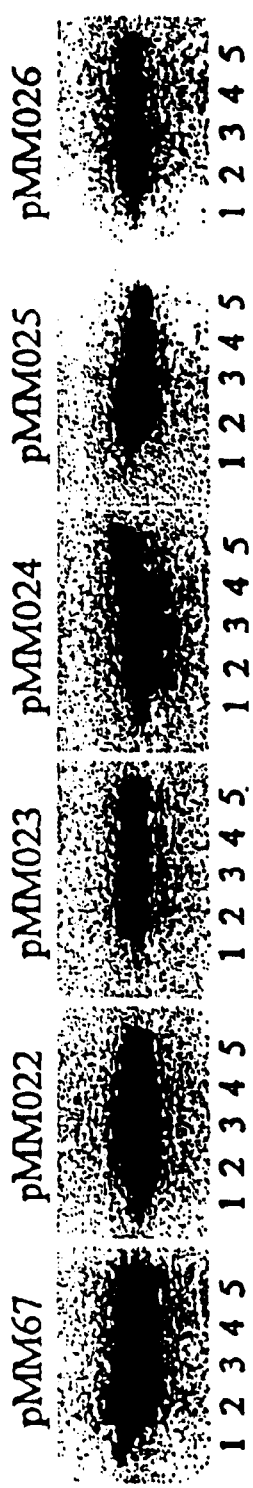
FIGS. 11A–11C show the analysis of the mRNA level and translational efficiency. (A) Primer extension analysis of the cspA-lacZ fusions. At mid-log phase, cultures of E. coli AR137 harboring various plasmids were shifted from 37° C. to 15° C. RNAs were prepared from the culture at 37° C. (0 h; lane 1) and at 0.5 (lane 2), 1 (lane 3), 2 (lane 4), and 3 h (lane 5) after the temperature downshift. Primer extension was carried out as described previously (Mitta et al., 1997). (B) Graphical presentation of the relative amounts of mRNA. Relative mRNA amounts were calculated from the radioactivities of transcripts shown in (A) using the transcript of pMM67 at 37° C. as 1. The relative amount is shown on the top of each column. Column 1, 0 h; column 2, after 0.5 h; column 3, after 1 h; column 4, after 2 h; and column 5, after 3 h. (C) Relative translational efficiencies of the cspA-lacZ mRNAs. Translational efficiencies at 15° C. were calculated by dividing the increment of β-galactosidase activity during the first 2 h after cold shock by the amount of mRNA using the following formula: [(Gal 2 h)×(OD 2 h)−(Gal 0 h)×(OD 0 h)]/(avg. mRNA) where (Gal 0 h) and (Gal 2 h) are β-galactosidase activities at 0 h and 2 h after temperature downshift, respectively; (OD 0 h) and (OD 2 h) are the optical densities at 600 nm of the cultures at 0 h and 2 h after temperature downshift, respectively; (avg. mRNA) is the average of relative mRNA amounts at 0.5, 1 and 2 h after temperature downshift. Relative translational efficiency of each mRNA was calculated using the efficiency of mRNA of pMM67 as 100%. Column 1, pMM67; column 2, pMM022; column 3, pMM023; column 4, pMM024; column 5, pMM025; and column 6, pMM026.
Figures 11B, 11C:
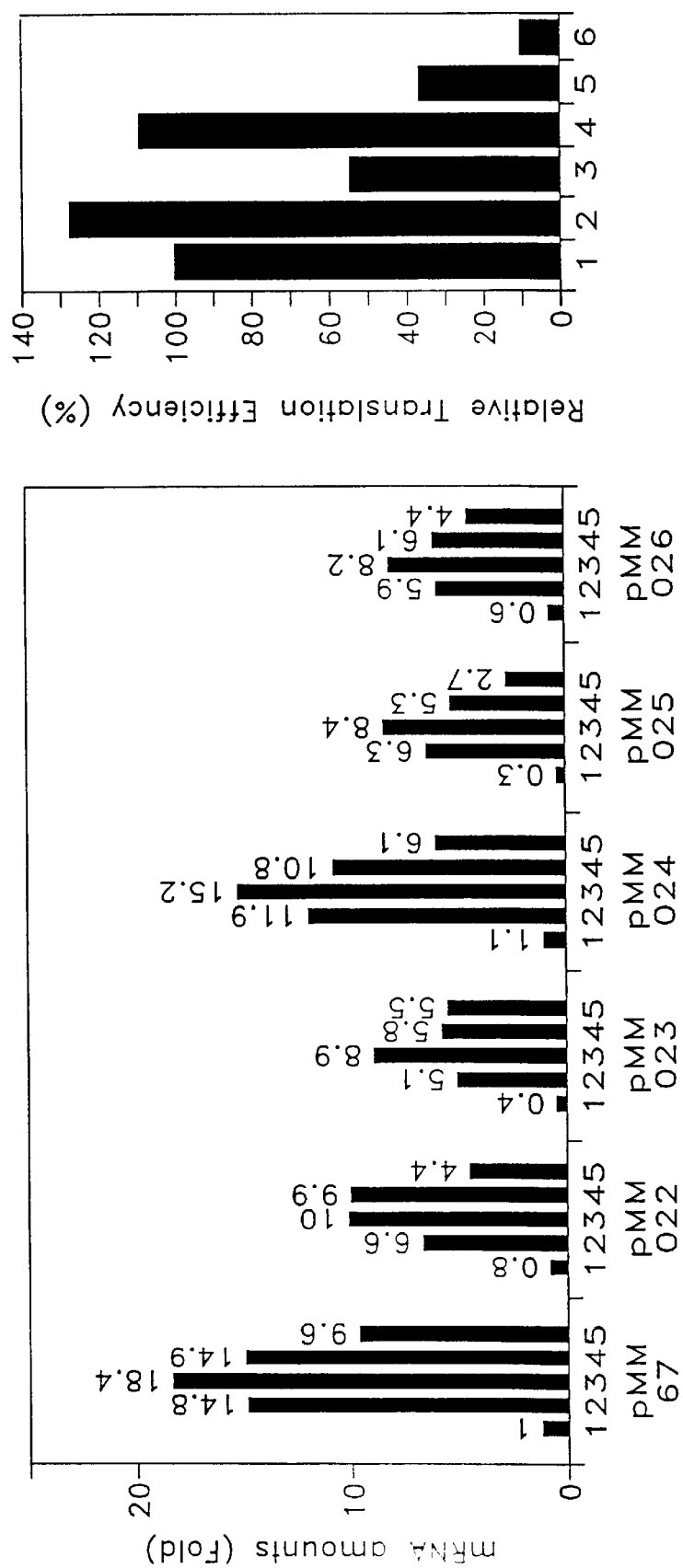

These results indicate that cspA induction efficiencies as measured by β-galactosidase activity are not correlated to the mRNA stability of each deletion construct, but rather to the amount of mRNA and/or its translation efficiency for each construct. Therefore, we next examined the amounts of mRNA for each construct at different time points after cold shock by the primer extension method. The results are shown in FIG. 11A and the amounts of transcripts were estimated by a phosphorimager. Their relative amounts were calculated using the amount of the transcript of pMM67 at zero time as 1 (FIG. 11B). At 37° C., the amounts of transcripts for pMM022 (Δ2-27) and pMM024 (Δ56-86) were very similar to that of the wild-type construct pMM67 (column 1 in FIG. 11B). It should be noted that β-galactosidase activity of pMM024 (Δ56-86) at 37° C. was more than 10 times higher than that of pMM022 (Δ2-27) (see FIG. 9B). In the case of pMM023 (Δ28-55), pMM025 (Δ86-117) and pMM026 (Δ118-143), the amounts of transcripts at 37° C. are approximately half of that of pMM67. Again it should be noted that β-galactosidase activity of pMM025 (Δ86-117) was 10 times higher than those of pMM023 (Δ28-55) and pMM026 (Δ118-143) (FIG. 9B). These results indicate that there is no correlation between the amounts of transcripts and the β-galactosidase activities at 37° C.

Example 10

Translational Regulation by the 5'-UTR

After temperature downshift, the amounts of the cspA-lacZ mRNAs dramatically increased in all the constructs and the induction patterns are shown in FIGS. 11A and 11B. They showed very similar pattern in accumulation of the transcripts as that of the wild-type pMM67, such that the maximal induction was observed at 1 h after temperature downshift. The patterns of mRNA levels were very similar between pMM67 and pMM024 (Δ56-86), while the others also showed a similar induction pattern although the amounts of their mRNAs were approximately a half of that of the pMM67 mRNA at each time point. Since the promoter activity of all the deletion constructs are considered to be the same, and in addition their mRNA stabilities were also very similar to that of the wild-type construct (FIG. 10B), lower amounts of mRNAs for all the deletion constructs except for pMM024 (Δ56-86) are probably due to their slower transcription elongation rate and/or transcription attenuation within the 5'-UTR. A remarkable finding was that the amounts of mRNA for pMM026 (Δ118-143) accumulated after cold shock were also identical to those for pMM022 (Δ2-27), pMM023 (Δ28-55) and pMM025 (Δ86-117) (see FIG. 11B). Nevertheless cold-shock induction of β-galactosidase activity was extremely low for pMM026 (Δ118-143) throughout cold-shock treatment (FIG. 9B), indicating that the mRNA for this construct was very poorly translated. Relative translation efficiencies at 15° C. was calculated for all the constructs from the increments of β-galactosidase activity during the cold shock and the amounts of mRNA (see the Brief Description of the Figures Legend to FIG. 11). As shown in FIG. 11C, the translation efficiency of pMM026 (Δ118-143) mRNA was extremely poor and calculated to be 9.5% of that of pMM67 mRNA (FIG. 11C column 6). Thus, it is clear that the deletion from base +118 to +143 of the 5'-UTR negatively affected on translation. Besides pMM026 (Δ118-143), the translation efficiencies of the mRNAs of pMM023 (Δ28-55) and pMM025 (Δ86-117) were relatively low and calculated to be 54 and 36% of that of pMM67 mRNA, respectively. These results clearly indicate that the translation efficiency of mRNA plays a crucial role in the regulation of cspA expression and that in particular, the region from base +118 to +143 of the 5'-UTR plays a major role in translation efficiency.

Figure 12:
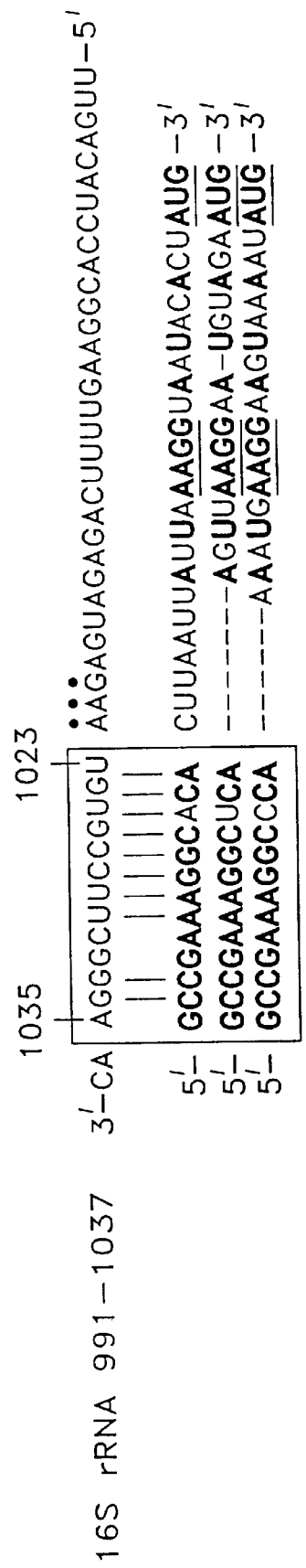
FIG. 12 shows sequence similarities of cspA, cspB, and cspG, mRNAs around the SD sequence and potential base pairing between cspA mRNA and 16S rRNA. Nucleotide numbers of cspA (Tanabe et al., 1992), cspB (Etchegaray et al., 1996), and cspG (Nakashima et al., 1996), are given starting from the major transcription initiation site as +1. The sequence of 16S rRNA is from Brosius et al., 1978. Nucleotides identical in the three csp mRNAs are shown in bold letters. The 13-base homologous sequence in cspA, cspB, and cspG are boxed (the upstream box). Positions of the SD sequence and the initiation codon are underlined. Potential base pairings between cspA mRNA and 16S rRNA are indicated by vertical lines. Positions of RNase VI sensitive sites (Powers et al., 1988) are dotted.

Nucleotide sequence comparison of the 5'-UTR regions of the cold-shock inducible genes, cspA, cspB and cspG, reveals that there is a 13-base sequence (from base +123 to +135 of cspA) conserved very well among these genes as shown in FIG. 12. Interestingly, these 13-base sequences are located immediately upstream of the Shine-Dalgarno sequence and contains a palindromic sequence to form a stable secondary structure ($\Delta G=-9.5$ kcal; see FIGS. 12 and 14). It is also complementary to the region from base 1023 to 1035 of 16S rRNA (FIG. 12). In the pMM026 (Δ118-143)

mRNA, this upstream-box region is deleted, which may be the major cause for the poor translation efficiency of the mRNA.

Figure 13A:
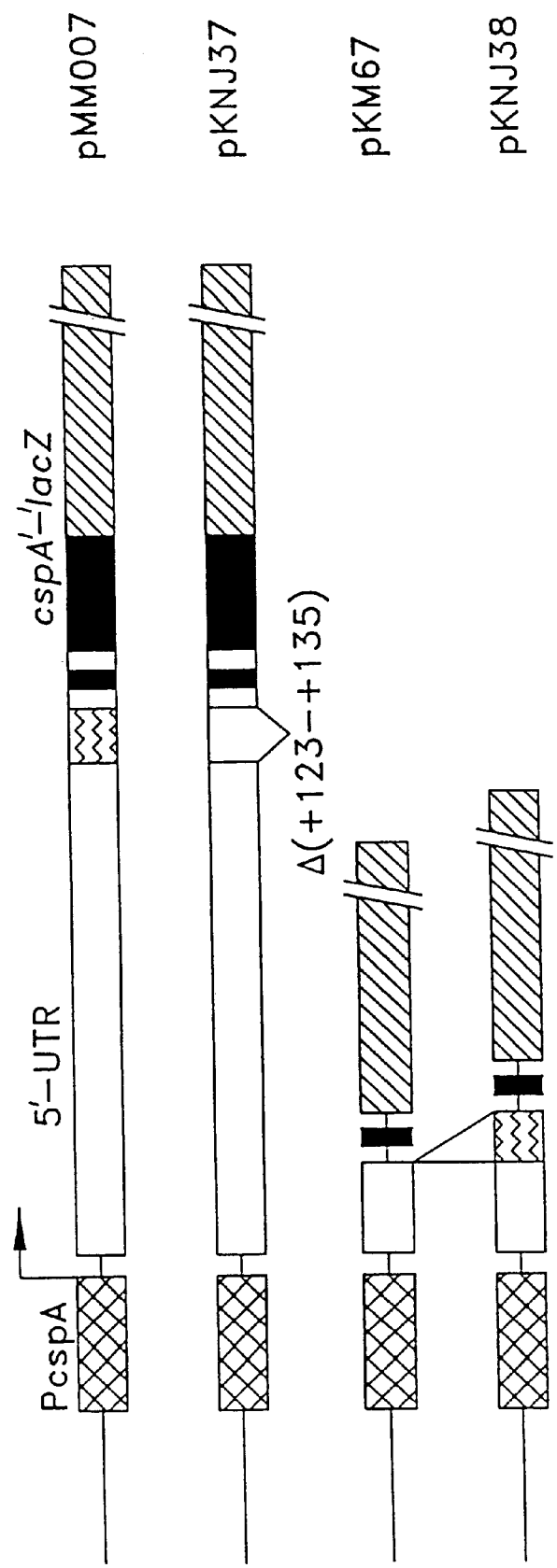
FIGS. 13A and 13B show the role of the 13-base upstream box sequence in the cspA 5'-UTR region in the cspA-lacZ expression. (A) Construction of cspA-lacZ fusions. The constructs are drawn in the same manner as shown in FIG. 9A except for a box with wavy lines, which represents the 13-base upstream box sequence, 5'-GCCGAAAGGCACA-3' (SEQ ID NO: 13) located upstream of the SD sequence. pKNJ37 is identical to pMM007 except for the deletion of the 13-base sequence. In both pMM007 and pKNJ37, cspA was translationally fused to lacZ. pKNJ38 is identical to pKM67 (Mitta, et al., 1997) except for the addition of the 13-base sequence by replacing the DNA fragment between XbaI and HindIII with synthesized oligonucleotides. In both pKM67 and pKNJ38, cspA was transcriptionally fused to lacZ. (B) Cold-shock induction of β-galactosidase. The cspA-lacZ fusions: pMM007 (○); pKNJ37 (●); pKM67 (Δ); and pKNJ38 (▼).
Figure 13B:
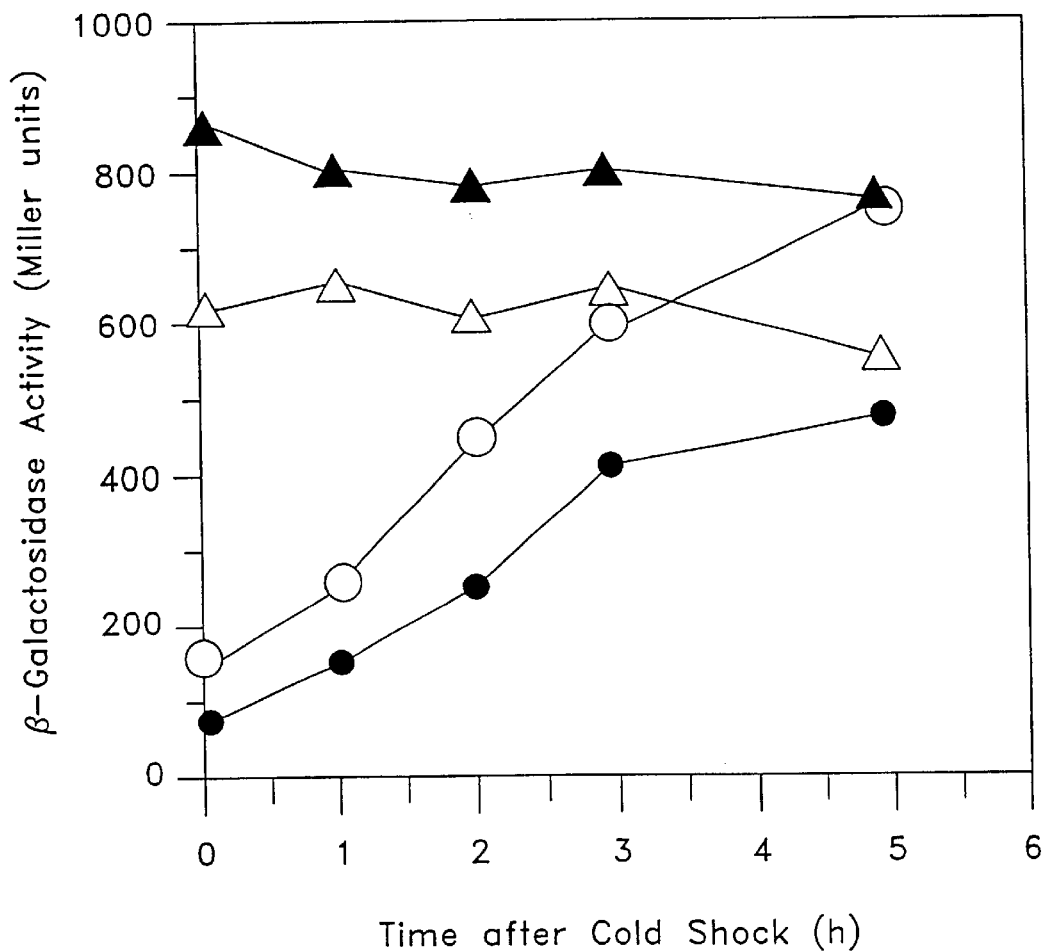
Figure 14A:
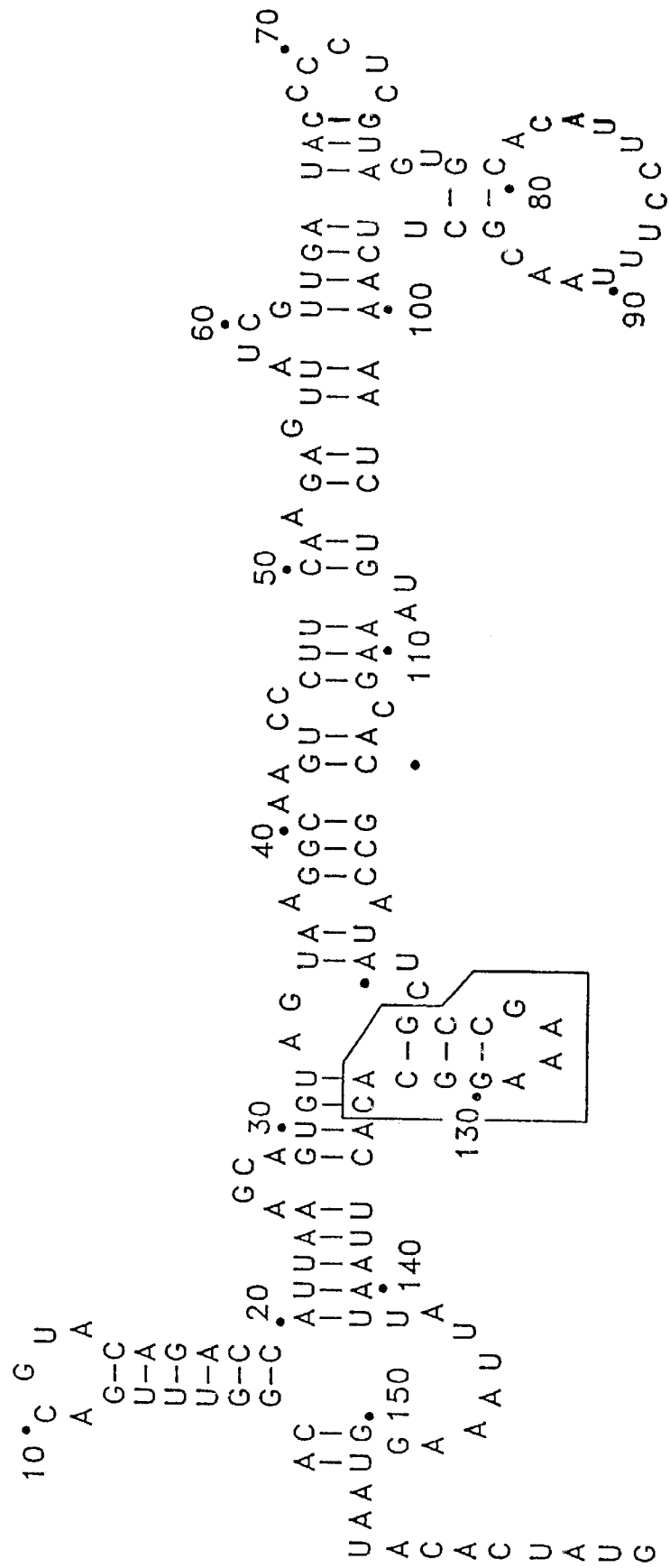
FIGS. 14A–14F show a comparison of the secondary structures of the 5'-UTRs for the deletion constructs. Secondary structures of the 5'-UTR for each deletion construct was predicted with a nucleotide sequence analysis program (DNASIS-Mac; Hitachi Software Engineering Co. Ltd.) based on the method of Zuker and Stieger, 1982. Nucleotides are numbered as the position in the cspA mRNA starting from the transcription initiation site as +1. The position of the deletion in each mutant is shown by an arrow with the nucleotide numbers of the deleted region. The highly conserved 13-base sequence upstream of the SD sequence designated the upstream box are boxed. The initiation codon and the SD sequence are also boxed.
Figure 14B:
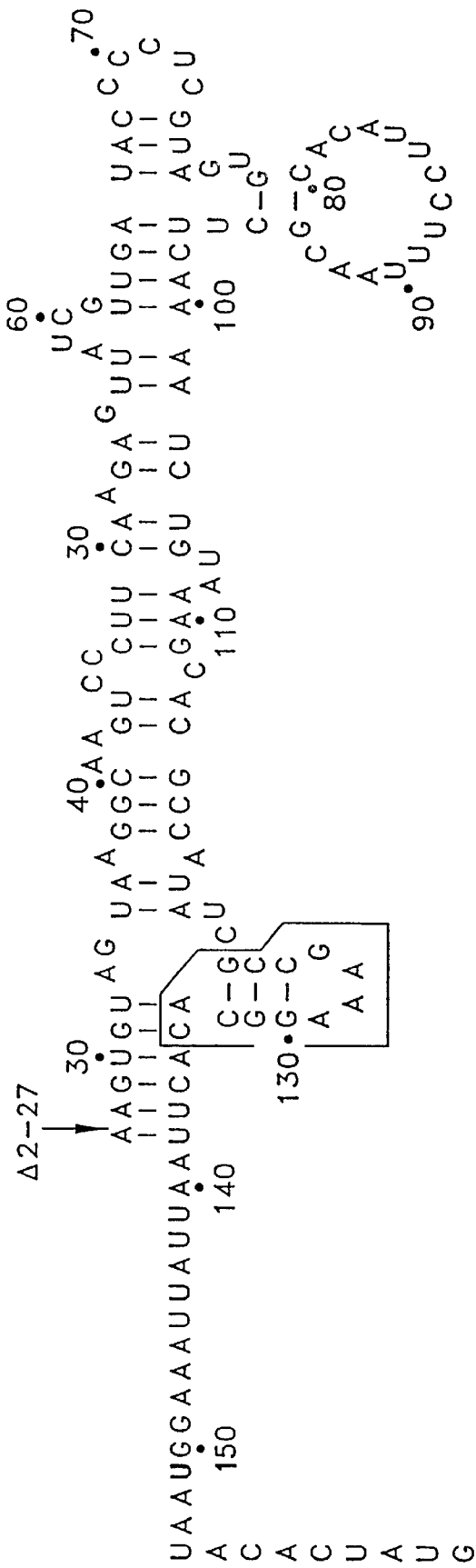
Figure 14C:
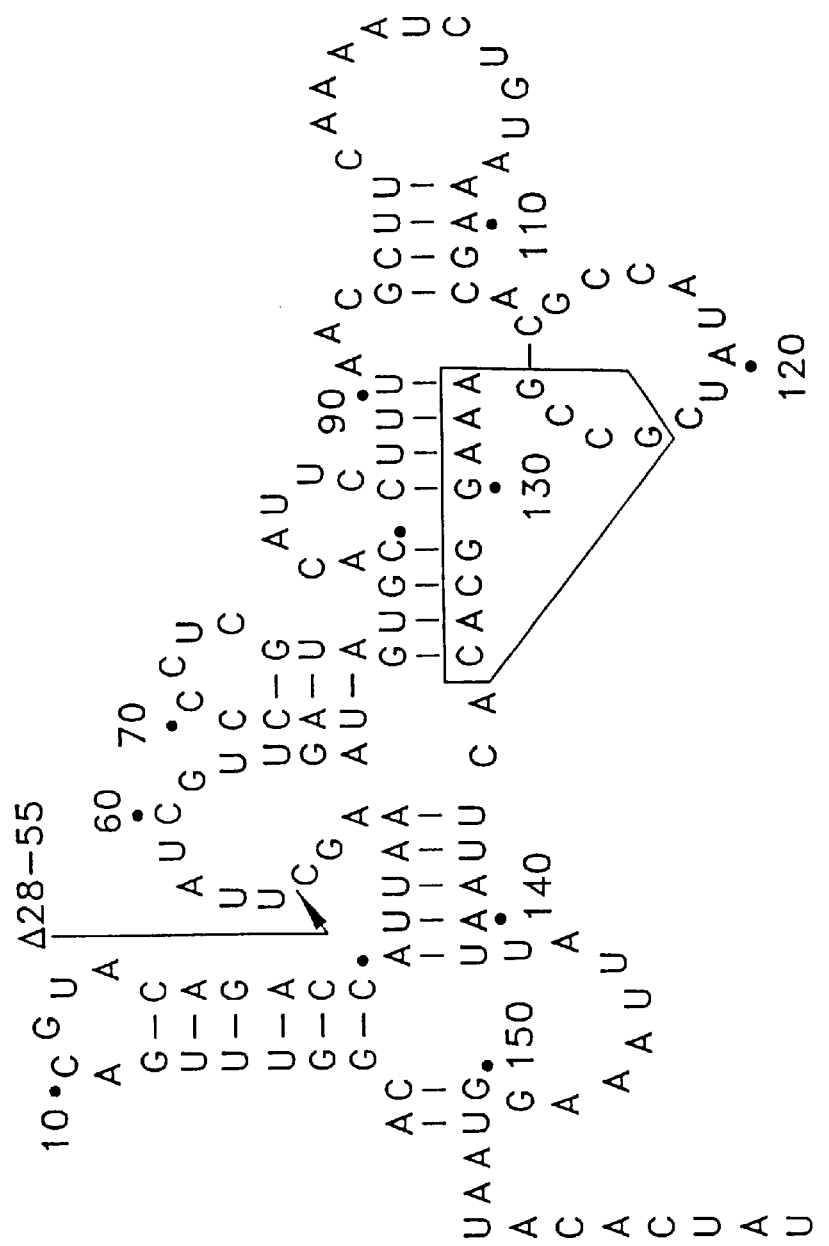
Figure 14D:
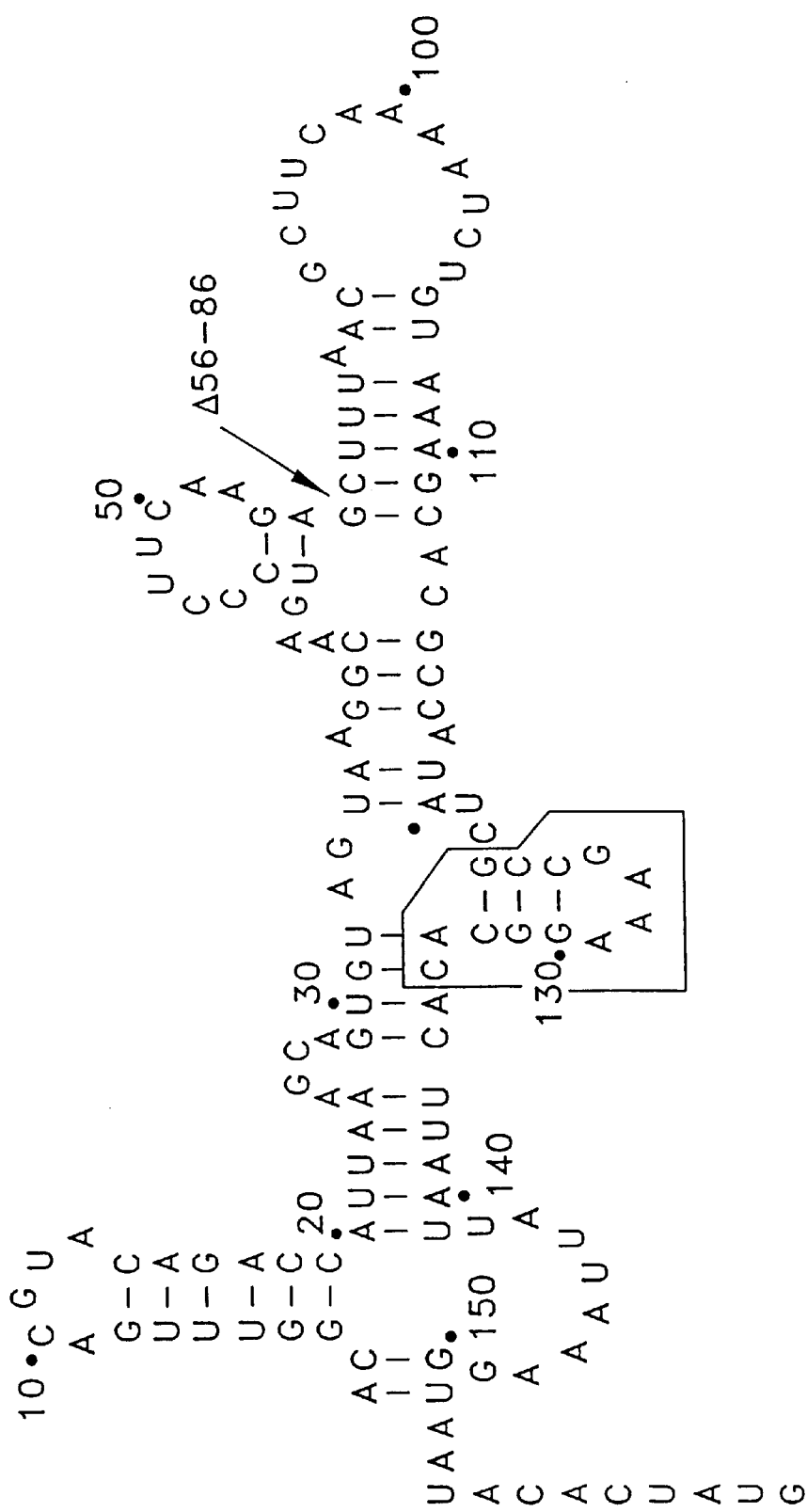
Figure 14E:
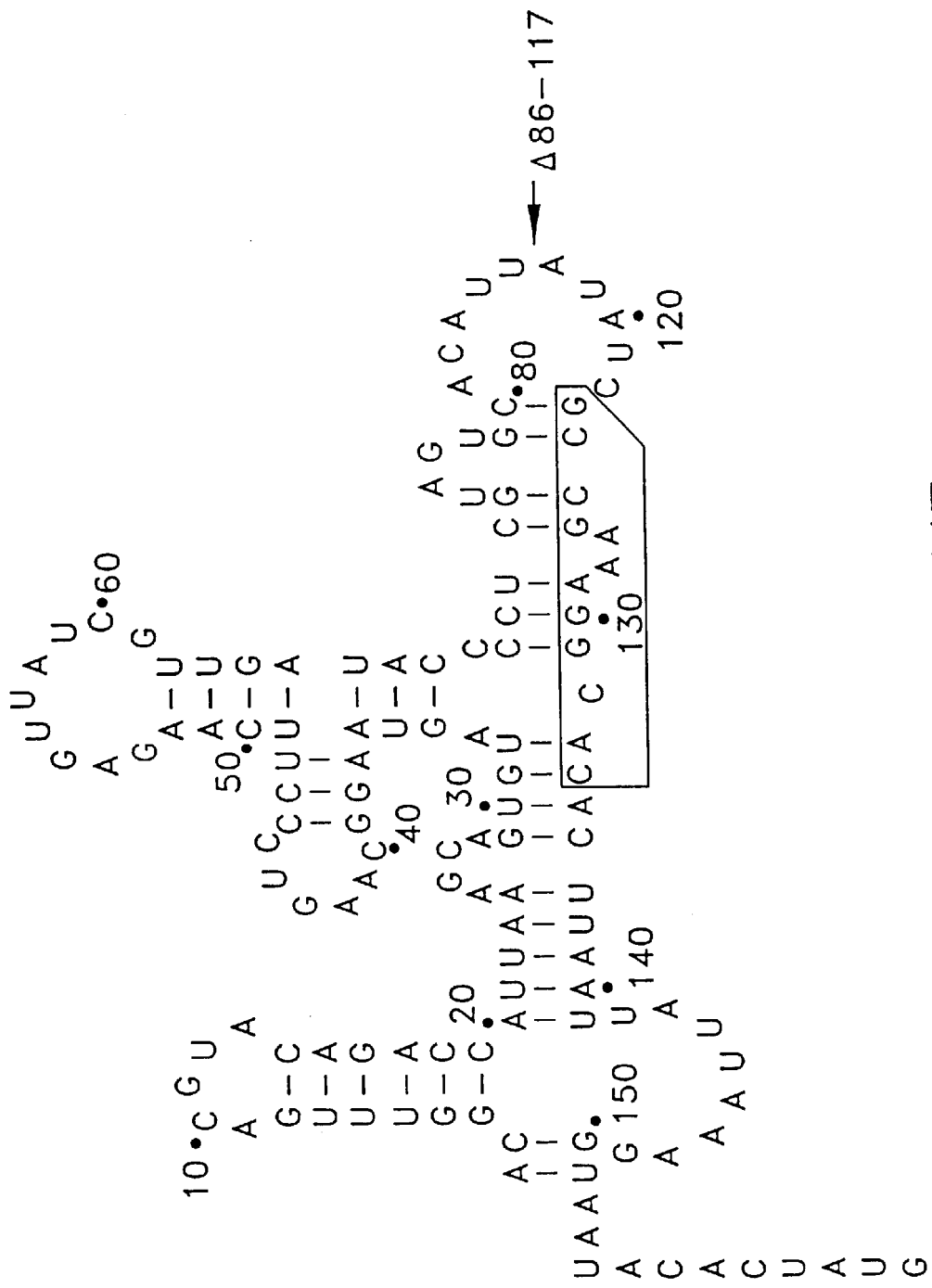
Figure 14F:
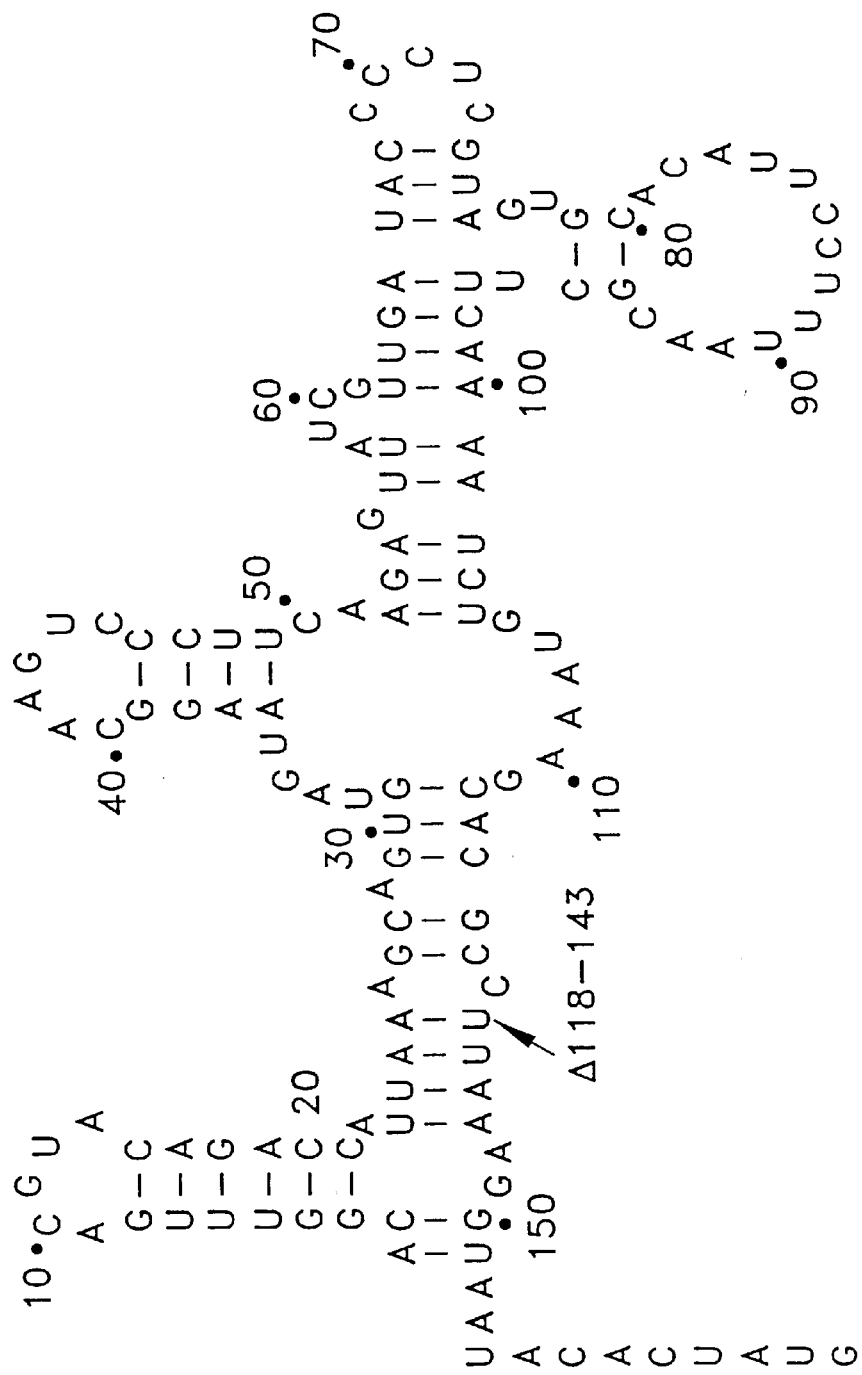

In order to characterize the role of the upstream box in translation efficiency, two new constructs were made; in one construct (pKNJ37) the exact 13-base upstream-box sequence was deleted from the wild-type cspA-lacZ construct (pMM007) and in another (pKNJ38) the 13-base sequence was added at the upstream region of SD of pKM67 (Mitta et al., 1997) as shown in FIG. 13A. In pKM67 the lacZ gene is fused at base +26, and it has been shown that as a result of the substantial deletion in the 5' UTR β-galactosidase became expressed even at 37° C. without any further induction upon cold shock (Mitta et al., 1997). Note that both pMM007 and pMM67 have the exactly identical insert of cspA in different vectors, pRS414 and pKM005, respectively. Cold-shock induction patterns of β-galactosidase activities of these two plasmids (pMM007 and pMM67) are similar (data not shown). Cells were transformed with pKNJ37, pMM007, pKNJ38 and pKM67, and cold-shock induction of β-galactosidase was examined. Deletion of the upstream box (pKNJ37) significantly lowered β-galactosidase activity not only at 37° C. but also upon cold shock (FIG. 13B). Contrary to the result, when the upstream box was inserted into pKM67 13 bases upstream of the SD sequence, the constitutive expression of β-galactosidase at 37° C. increased by approximately 20% (FIG. 13B). This increment was also kept upon cold shock. These results support the notion that the upstream-box sequence is associated with efficient translation of cspA. Specific sequences of the 5' UTR which are useful in the invention include 5'-GCCGAAAGGCACA-3' (SEQ ID NO: 9), 5'-GCCGAAAGGCUCA-3' (SEQ ID NO: 55), and 5'-GCCGAAAGGCCCA-3' (SEQ ID NO:56). (See FIG. 2).

It is currently considered that cspA expression is regulated at the levels of transcription, mRNA stability and translation as follows: (I) The cspA gene has a strong promoter equipped with the UP element, which works at both 37° C. and 15° C. (Fang et al., 1997; Goldenberg et al., 1997; Mitta et al, 1997), although transcription of the cspA gene does not require any de novo protein synthesis upon cold shock. (ii) The cspA mRNA contains the downstream-box (DB) sequence downstream of the initiation codon, which plays a major role in enhancement of translation initiation at low temperatures (Etchegaray and Inouye, unpublished; Mitta et al., 1997). (iii) It is very important to note that the cspA mRNA has an unusually long 5'-UTR (Tanabe et al., 1992), consisting of 159 bases, and is extremely unstable at 37° C. (Brandi et al., 1996; Goldenberg et al., 1996; Bae et al., 1997; Fang et al., 1997; Jiang et al., 1997; Goldenberg et al., 1997; Mitta et al., 1997). Immediately upon cold shock, the cspA mRNA becomes stable. Again, this stabilization of mRNA upon cold shock does not require any de novo protein synthesis. When the region from base +26 to +143 of the 5'-UTR was deleted from the cspA-lacZ fusion construct, high β-galactosidase activity was obtained even at 37° C. (Mitta et al., 1997). In the 5'-UTR, there is a putative RNaseE cleavage site immediately upstream of the SD sequence (Fang et al., 1997). This site is considered to be responsible for the extreme instability of the cspA mRNA, since the three-base substitution mutation at this region resulted in 150-fold stabilization of the mRNA, allowing a high CspA production even at 37° C. (Fang et al., 1997). Thus, it is clear that the unusually long 5'-UTR of the cspA mRNA is responsible for its instability at 37° C. It can be considered that the 5'-UTR makes the cspA mRNA extremely unstable at 37° C., in such a way as cspA is cold-shock inducible. It is worth mentioning that although the cspA mRNA becomes stable and is accumulated at the nonpermissive temperature in the temperature-sensitive RNaseE mutant, CspA production was not detected under this condition (Fang et al., 1997), suggesting that in addition to the stability of mRNA another role may exist in the 5'-UTR.

We have attempted to further elucidate the roles of the unusually long 5'-UTR of the cspA mRNA in cspA expression. We made a series of 26- to 32-base deletion mutations encompassing the entire 5'-UTR. These mutated 5'-UTR regions were translationally fused to lacZ at the 13th amino acid residue of CspA after the DB sequence. At 37° C., pMM022 (D2-27), pMM023 (D28-55) and pMM026 (D118-143) showed the similar β-galactosidase activities as the wild-type pMM67, while pMM024 (D56-86) and pMM025 (D86-117) showed more than 10 fold higher β-galactosidase activities than pMM67, indicating that the region from base +56 to +117 is involved in the repression of cspA expression at 37° C.

Based on the β-galactosidase activities after temperature downshift, mutants can be classified into three classes; those in Class I [pMM022 (D2-27) and pMM024 (D56-86)] in which β-galactosidase is induced in a similar fashion to pMM67, those in Class II [pMM023 (D28-55) and pMM025 (D86-117)] in which cold-shock induction of β-galactosidase is poor, and that in Class III [pMM026 (D118-143)] with very low β-galactosidase activities both before and after cold shock. It is worth mentioning that these differences were due to neither the amounts nor the stability of mRNA as evident from FIGS. 10 and 11. This supports the notion that the 5'-UTR has another role in translation efficiency in addition to the stability of mRNA as mentioned above.

The relative translation efficiencies after temperature downshift for different constructs showed surprisingly significant differences (FIG. 11C), which coincide well with the classification of the constructs at 15° C. as described above. The translation efficiencies with pMM022 (D2-27) and pMM024 (D56-86) (Class I) are a little better than that of the wild-type pMM67, those with pMM023 (D28-55) and pMM025 (D86-117) (Class II) are 40 to 50% of that of pMM67, and that with pMM026 (D118-143) (Class III) is less than 10% of that of pMM67.

In pMM026 (D118-143), the deletion mutation is clearly affecting the translation efficiency but not the stability of mRNA. The deleted region was found to contain a 13-base sequence (base +123 to +135) well conserved in the mRNAs for all the cold-shock inducible cspA family, cspA, cspB, cspG, and cspI (see FIG. 12). This sequence designated the upstream box may form a distinct secondary structure in both the wild-type pMM67 and Class I constructs [pMM022 (D2-27) and pMM024 (D56-86)] (FIG. 14). Class I constructs showed a similar translation efficiency to the wild-type. In Class II [pMM023 (D28-55) and pMM025 (D86-117)], which showed 50% of translation efficiency of the wild-type, this secondary structure disappears, however, the predicted secondary structures around the SD sequence in these constructs are still similar to that of the wild-type construct. In contrast, when the upstream-box region is deleted [pMM026 (D118-143); Class III, which showed a very poor translation efficiency], the SD region forms a more stable secondary structure. This likely prevents recognition of the mRNA by ribosomes, causing a very poor translation efficiency in pMM026 (D118-143). Therefore the upstream box may function to punctuate the formation of a stable secondary structure immediately upstream of the SD sequence, allowing it highly accessible to ribosomes. Alternatively, as the upstream-box sequence is complementary to the 16S rRNA sequence from base 1023 to 1035 (see FIG. 12), it is possible that the upstream-box sequence may be another cis-element, which may enhance translation efficiency by forming a duplex with 16S rRNA in addition to the SD sequence and the downstream box (Mitta et al. 1997). Since all the constructs use the identical site of cspA to fuse to lacZ, the observed differences in translation efficiency are considered to be at the level of translation initiation but not at the level of translation elongation. It has been suggested that such an interaction between mRNA and 16S rRNA plays an important role in translation initiation (McCarthy and Brimacombe, 1994). The region from base 1023 to 1035 of 16S rRNA has been shown to be near the site where 30S ribosomes interact with mRNA on the basis of the fact that the U residue at position 1052 directly interacts with the 6th base from the initiation codon (Dontsova et al., 1992; Rinke-Appel et al., 1993). Furthermore, it has been reported that RNase VI sensitivity at G1020, A1021 and A1022 increased immediately after the assembly of 30S ribosomal subunits, indicating that the site encompassing these residues is exposed to the surface (Powers et al., 1988).

Consistent with the proposed role of the upstream box in the translation, the addition of an upstream-box sequence to pKM67 resulted in increase of β-galactosidase activity approximately by 20%. On the other hand, the deletion of the exact 13-base upstream-box sequence [pKNJ37 (D123-135) in FIG. 13] resulted in 50% reduction of β-galactosidase activity at 37° C. and a lower level of induction upon cold shock. Note that the predicted secondary structure surrounding the SD sequence of pKNJ37 (D123-135) is the same as the wild-type (FIG. 14).

In the heat shock response, the synthesis of the heat-shock sigma factor, $\sigma^{32}$, is regulated at the level of translation and the secondary structure of the rpoH mRNA plays a crucial role in this regulation (Nagi et al., 1991; Yuzawa et al., 1993). Very recently, the secondary structure of the rpoH mRNA has been determined by chemical and enzymatic probing assays and the results are completely consistent with the predicted rpoH secondary structure proposed previously (Morita et al., 1999). It has also been shown that mutations in the rpoH mRNA, which are predicted to decrease the mRNA stability, increased rpoH expression and vice versa (Morita et al., 1999). Toeprinting assays using the wild-type rpoH mRNA and 30S ribosomes showed that the toeprinting appearance totally depends on temperature, indicating that the rpoH mRNA secondary structure at 42° C., which is accessible to ribosomes, is different from that at 30° C., and that the rpoH mRNA structure itself is a determinant for rpoH expression without any other factors (Morita et al., 1999). Thus, it was proposed that the rpoH mRNA acts as an RNA thermosensor (Morita et al., 1999). Storz (1999) discussed that the lcrF mRNA of *Yersinia pestis* (Hoe et al., 1993) and the 1 phage cIII mRNA (Altuvia et al., 1989) might be other examples for RNA thermosensor.

In summary, stabilization of the cspA mRNA upon cold shock is prerequisite for CspA production. This stabilization does not require any de novo protein synthesis. As presented here, translation efficiency, which may involve the secondary structure of the 5'-UTR, in particular surrounding the SD sequence, of cspA mRNA, is turned out to play an important role in cspA expression in addition to the mRNA stabilization. It is thus possible that the cspA mRNA might act as an RNA thermometer as proposed for the rpoH mRNA. To know the more precise molecular mechanism of the regulation of cspA expression, determination of the secondary structure of the cspA mRNA and the relationship between the secondary structure and the translation efficiency remain to be addressed. The point mutation analysis in addition to the deletion analysis presented here will give us information on the molecular anatomy of the structure and function of 5'-UTR of the cspA mRNA.

Example 11

Figure 15A:
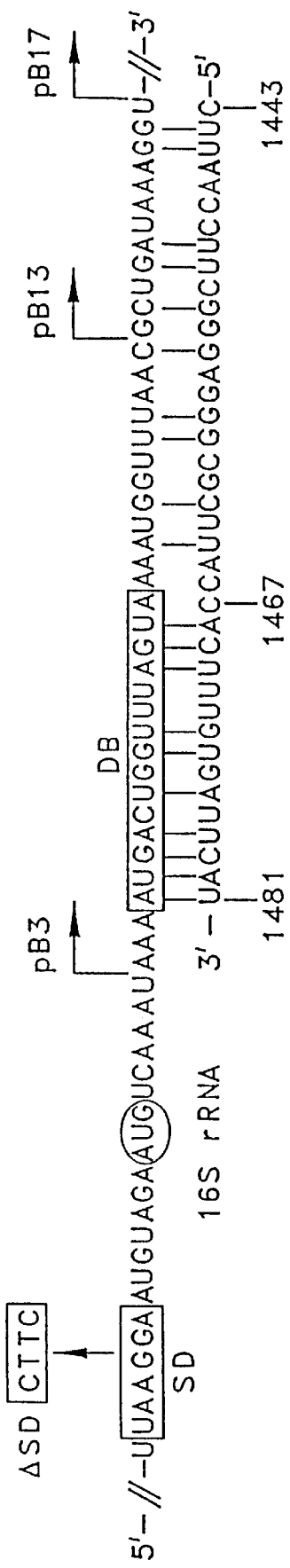
FIGS. 15A–15E show enhancement of cspB translation by DB. (A) cspB-DB-anti-DB complementarity: the cspB-DB sequence is boxed and encompasses the region from codons 5 to 9 (Mitta et al., 1997). Additional cspB mRNA-16S rRNA possible base pairings downstream of DB are also shown. The AUG codon is circled, the SD sequence is boxed and L-shaped arrows show the positions where the cspB gene was fused to lacZ. (B) Translational cspB-lacZ fusion constructs. On the top, the E. coli csp gene is depicted with its 5' end. In pB3, pB13 and pB17, the lacZ gene is fused to cspB at residue +177 (3 aa), +200 (13 aa) and +212 (17 aa), respectively. The pB13sd and pB17sd are the same as pB13 and pB17, respectively, except that their SD sequences are changed from 5'-AGGA-3' to 5'-CTTC-3'. (C) β-galactosidase activity of the cspB-lacZ constructs obtained before (time 0) and after (1, 2 and 3 hr) temperature shift from 37 to 15° C. E. coli AR137 cells were transformed with pB3, pB13, pB13sd, pB17 and pB17sd were grown in medium, and at mid-log phase ($OD_{600}$=0.4) cultures were shifted from 37 to 15° C. β-galactosidase activity was measured. (D) mRNA levels of pB3, pB13, pB17 or pB13sd after temperature shift from 37 to 15° C.: the cspB-lacZ mRNAs were detected by primer extension before temperature downshift (time 0) and at 1, 2 and 3 hrs after temperature shift. (E) mRNA stability from pB3, pB13, pB17 and pB13sd: E. coli AR137 cells transformed with pB3, pB13, pB17 and pB13sd were grown under the same conditions described above. At mid log phase, the culture was shifted to 15° C. and after 30 min., rifampicin was added to a final concentration of 0.2 mg/ml (time 0). Total RNA was extracted at 5, 10 and 20 min. after rifampicin addition. The cspB-lacZ mRNAs were detected by primer extension.
Figure 15B:
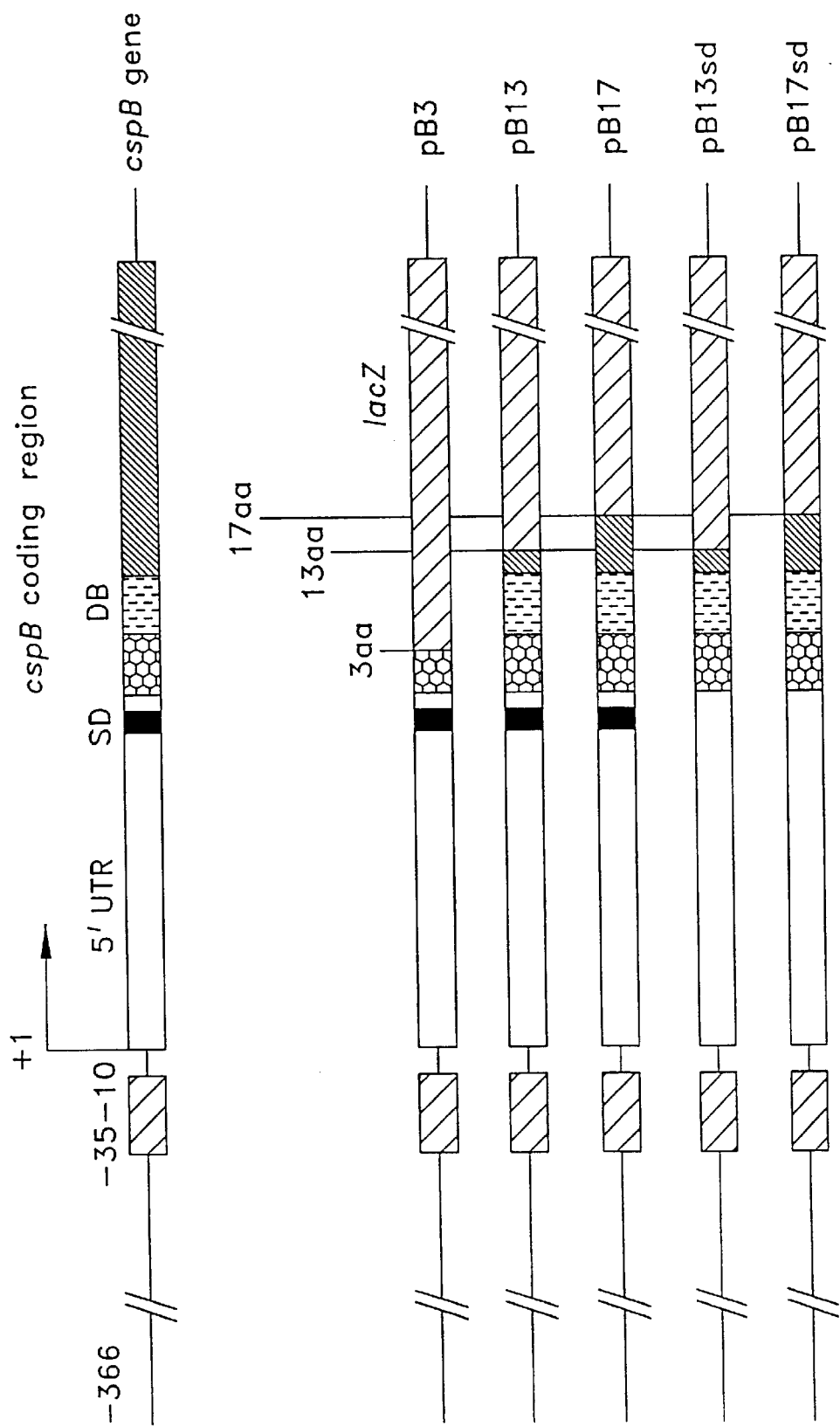
Figure 15C:
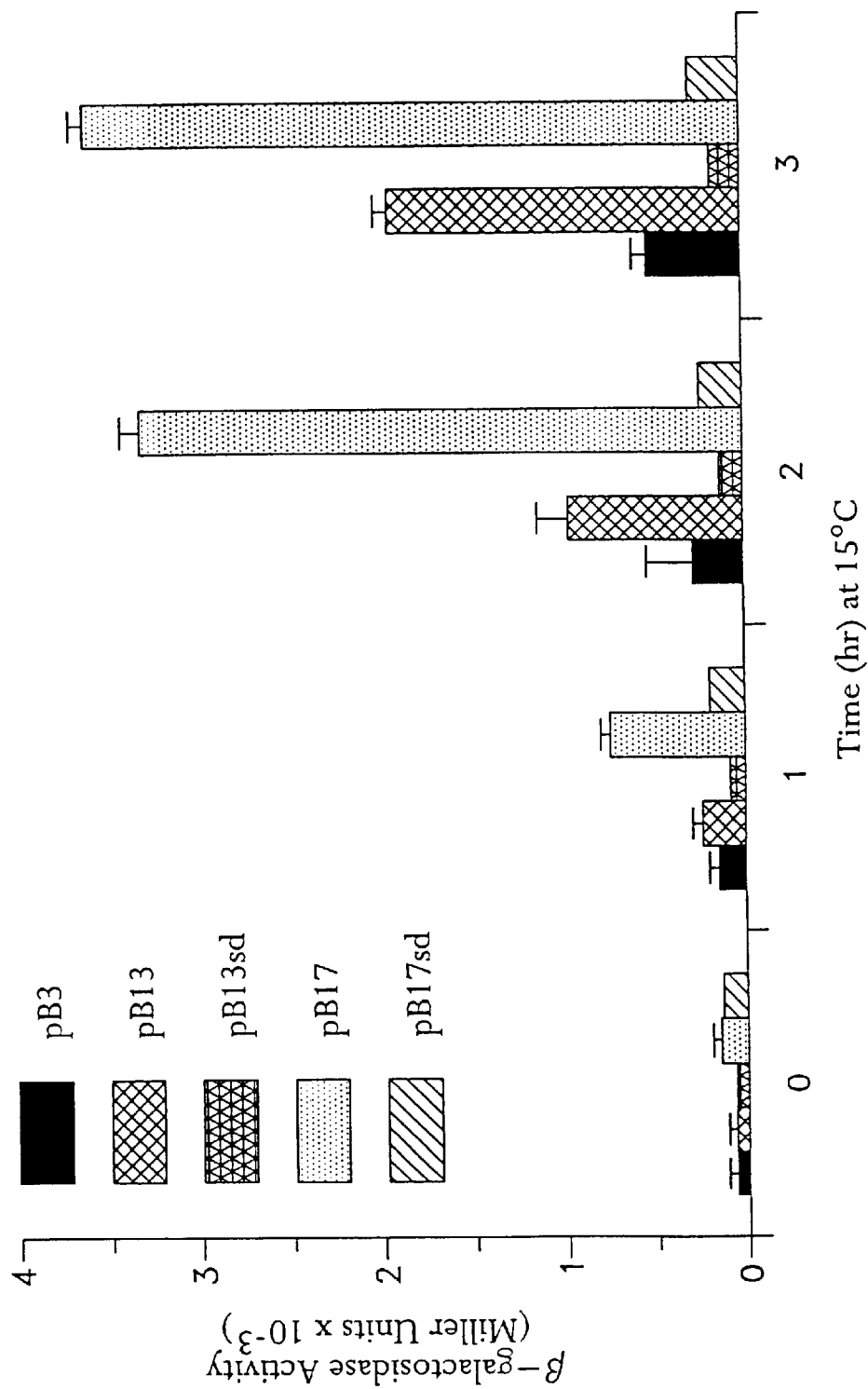
Figure 15D:
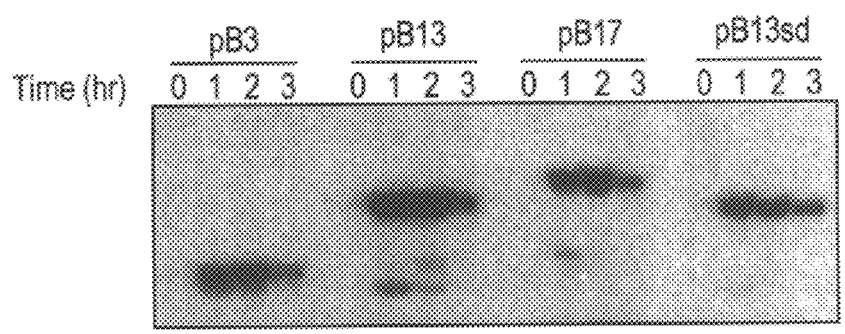

The Role of DB in the Cold-shock Induction of cspB, and the Effect of a Perfectly Matching DB Previously, we have demonstrated that the expression of cspB at low temperature is primarily regulated at the mRNA level (Etchegaray et al., 1996). Here, we first show that DB is an important contributor to the translational induction of cspB at low temperature. *E. coli* AR137, a pcnB mutant which maintains pBR322 derivative plasmids at low copy (Lopilato et al., 1986) was transformed with a series of cspB-lacZ translational fusions (FIGS. 15A and 15B). FIG. 15C shows β-galactosidase activity at various time points after temperature shift from 37 to 15° C. After 3 hr at 15° C., pB13 and pB17 show the highest levels of β-galactosidase activity, indicating that a region from codon 3 and 13 (containing DB) plays a major role in high expression of cspB at low temperature. Levels of β-galactosidase units from the SD-deletion constructs pB13sd and pB17sd demonstrate that SD is also required for the induction of cspB. Primer extension analysis (FIG. 15D) shows that the mRNA levels of pB3 and pB17 are almost identical, while the β-galactosidase activity of pB17 is 7 times higher than that of pB3 (FIG. 15C), demonstrating that the differences in the sequence downstream of the initiation codon cause a significant effect on the efficacy of mRNA translation but not on the amount of the mRNAs. Based on the amounts of mRNA estimated using a phosphorimager and the increments of β-galactosidase activity between 1 and 2 hr. after cold-shock induction, the translational capability of pB17 was calculated to be 6 times higher than that of pB13 and 18 times higher than that of pB3. This could be explained by the potential to form additional base-pairing between the cspB-mRNA (pB17) and the 16S rRNA as shown in FIG. 15A. This suggests that a longer DB (pB17) could be more effective for translation than a shorter DB (pB13). When the SD sequence was deleted from pB13, the translational efficiency became even lower than that of pB3, indicating that both SD and DB are required for the full expression of cspB at low temperature.

Figure 15E:
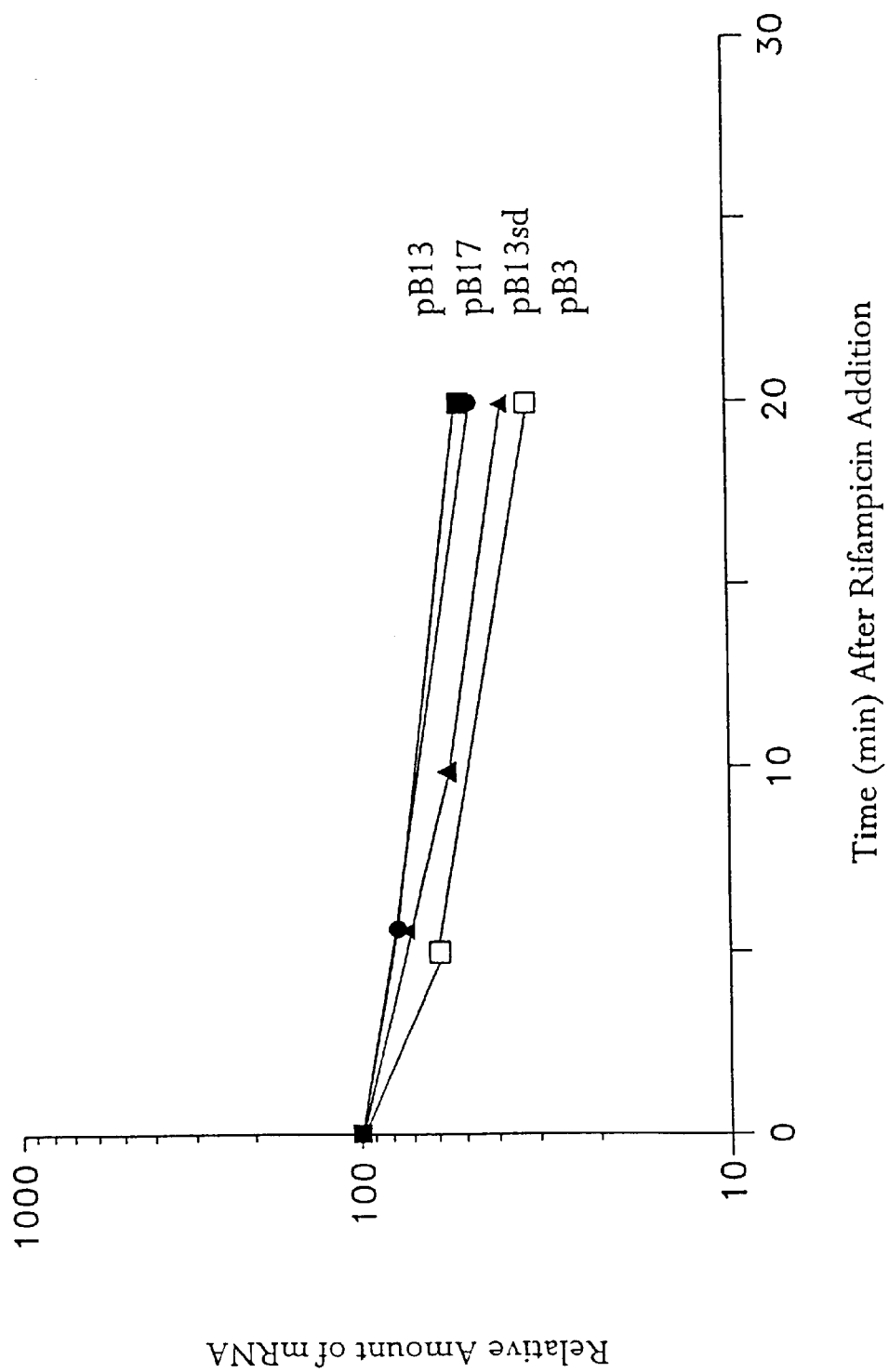

It has been shown that mRNA stability plays a role in the cold-shock inducibility of cspA (Brandi et al., 1996; Goldenberg et al., 1997; Fang et al., 1997). However, the dramatic effect of DB on the lacZ expression cannot account for the differences of the mRNA stabilities at 15° C. between the constructs with and without DB. FIG. 15E shows the half-life for pB3, pB13, pB13sd and pB17 to be 12, 22, 15 and 20 minutes, respectively.

It has been shown that mRNA stability plays a role in the cold-shock inducibility of cspA (Brandi et al., 1996; Goldenberg et al.,1997; Fang et al., 1997). However, the dramatic effect of DB on the lacZ expression cannot account for the differences of the mRNA stabilities at 15° C. between the constructs with and without DB. FIG. 1E shows the half life for pB3, pB13, pB13sd, and pB17 to be 12, 22, 15 and 20 minutes, respectively.

It has been previously shown that DB is essential for the production of CspA at low temperature (Mitta et al., 1997).

However, the wild-type DB of cspA has 10 matches out of possible matches to the anti-DB in 16S rRNA (Mitta et al., 1997). Therefore, we added DBs of 12 (pJJG78DB1) or 15 (pJJG78DB2) bases that are complementary with the anti-DB of 16S rRNA to the site after the 5th codon of lacZ under the cspA regulatory system in pJJG78 (see FIG. 15A) to examine if they enhance lacZ expression at 15° C. Mid-log phase cells (pcnB⁻) grown at 37° C. were shifted to 15° C. and β-galactosidase activity was measured at 1, 2 and 3 hr after the shift. FIG. 15B shows that at 1 hr at 15° C. the β-galactosidase activity was 3 and 8 fold higher with pJJG78DB1 and pJJG78DB2, respectively than with pJJG78. After 2 and 3 hr at 15° C., the β-galactosidase activity was increased 3.5 and 10.5 times with pJJG78DB1 and pJJG78DB2, respectively than with pJJG78. Moreover, the effect of the DB was observed at 37° C. in which the β-galactosidase activity of pJJG78DB1 and pJJG78DB2 was 2 and 4 fold higher as compared with pJJG78. The amount of the lacZ mRNA (FIG. 15C) as well as the mRNA stability did not vary significantly between these constructs. The lacZ mRNA half-life from pJJG78, pJJG78DB1 and pJJG78DB2 was calculated to be 27, 23 and 25 min respectively. In addition, computer analysis (Zuker and Stieger 1982) revealed no significant differences in the mRNA secondary structures among pJJG78, pJJG78DB1 and pJJG78DB2, suggesting that the insertion of the perfectly matching DB may not have a particular effect in the mRNA secondary structures that could account for the difference in their β-galactosidase expression. These results indicate that DB function as a translational enhancer and that greater complementarity to the anti-DB improves translational efficiency and/or that specific base-pairings like the first 3 nucleotides of the DB from pJJG78DB2 may play an important role for the DB activity.

Example 12

Analysis of DB Function

Figure 16A:
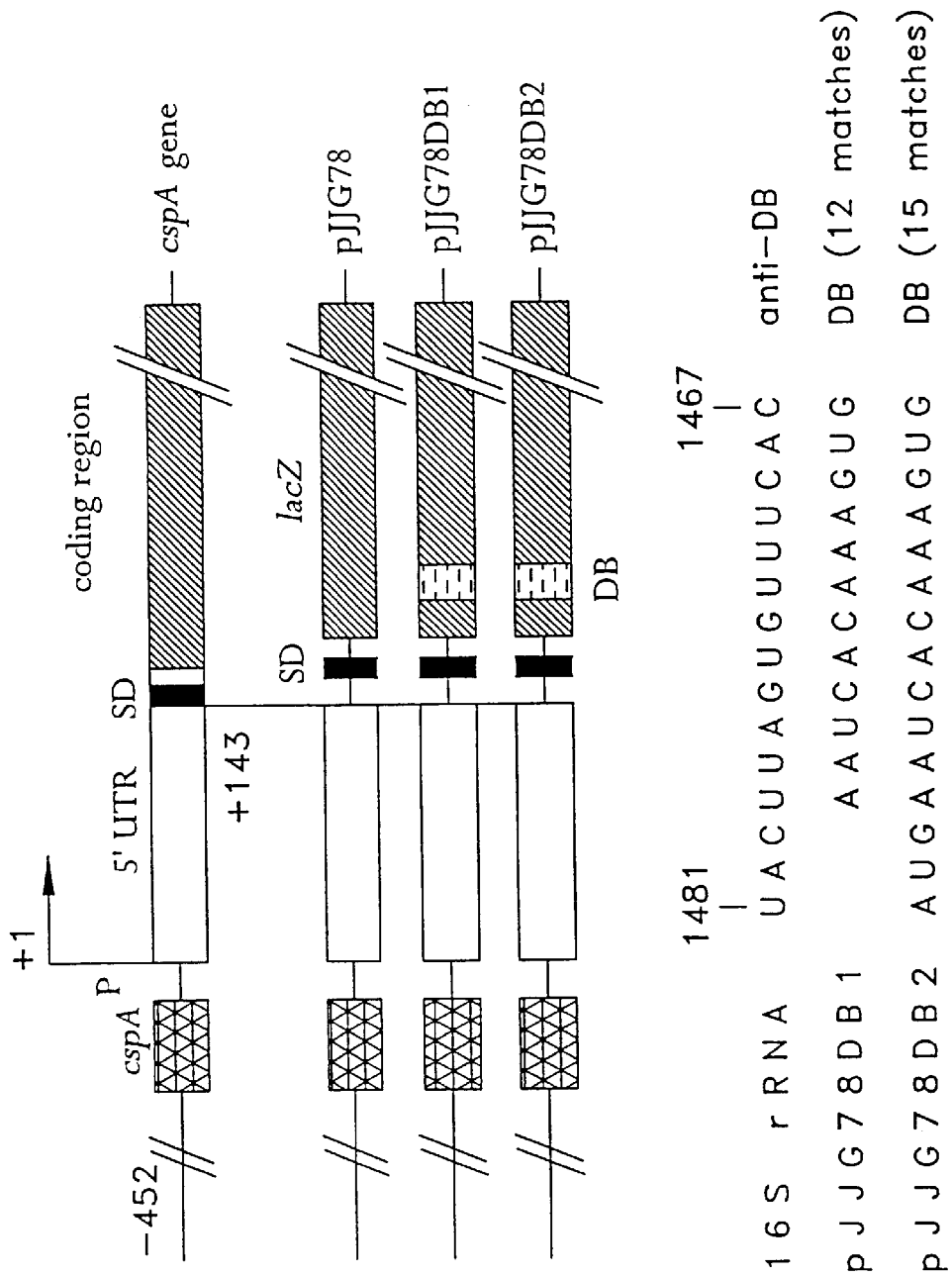
FIGS. 16A–16D show the effect of a perfectly matching DB enhancing the translation of cspA. (A) Translational cspA-lacZ fusion constructs. The cspA gene structure from its 5'-end is showed at the top. pJJG78DB1 and pJJG78DB2 were constructed from pJJG78 as described in Experimental Procedures. The DB sequences of pJJG78DB1 (12 matches) and pJJG78DB2 (15 matches) are shown at the bottom.
Figure 16B:
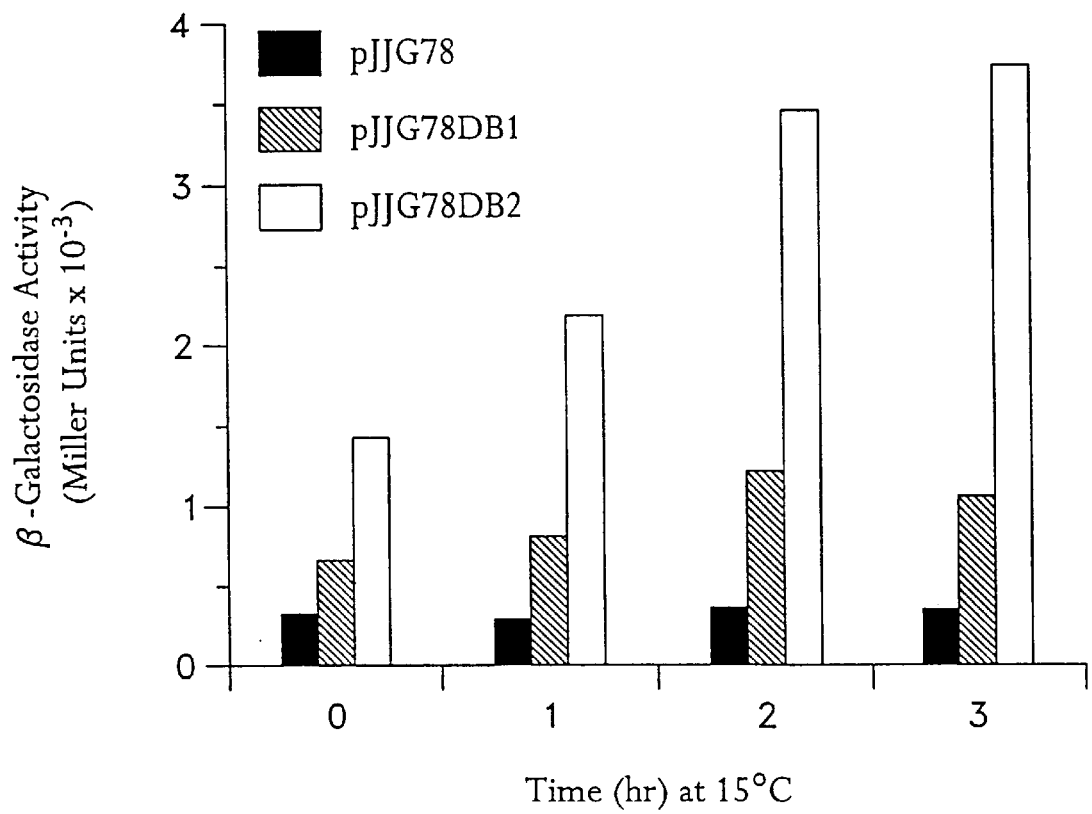
Figure 16C:
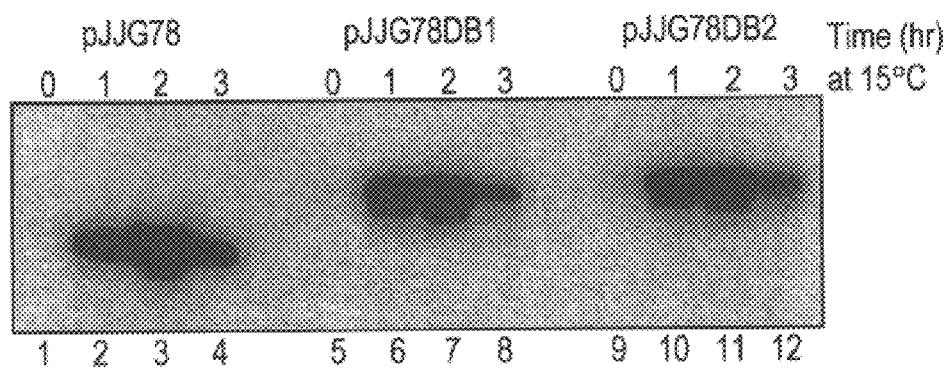
Figure 16D:
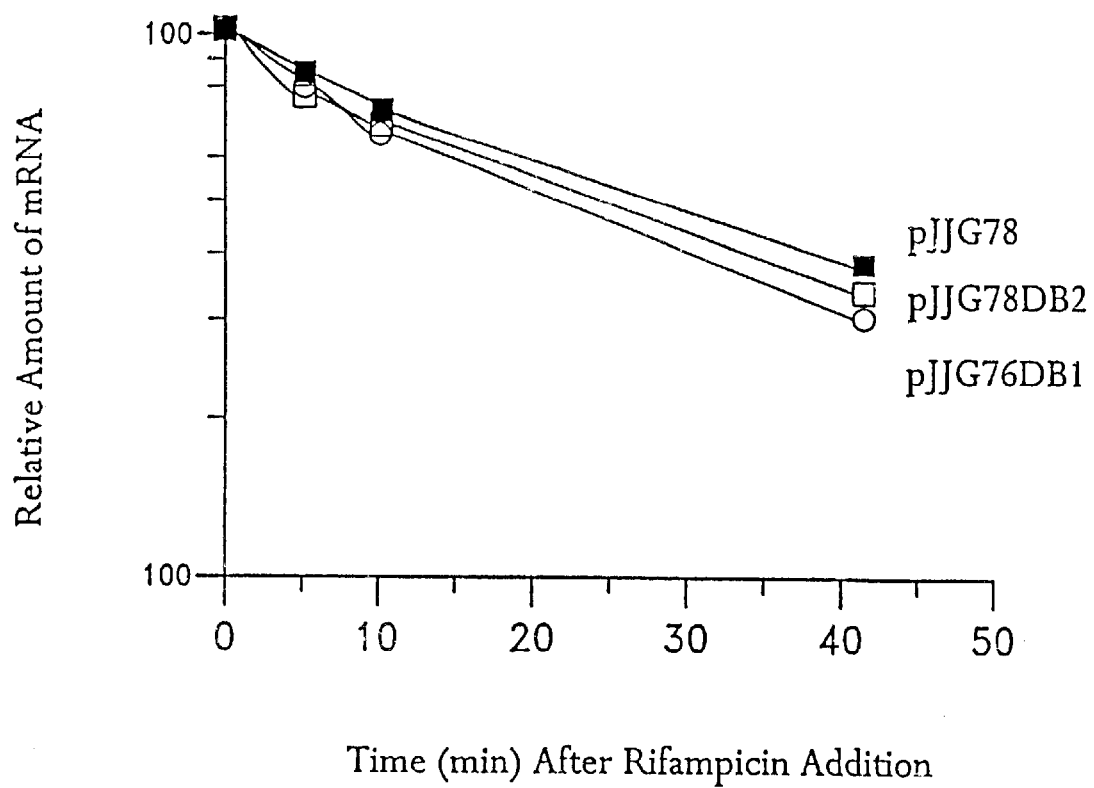
Figure 17A:
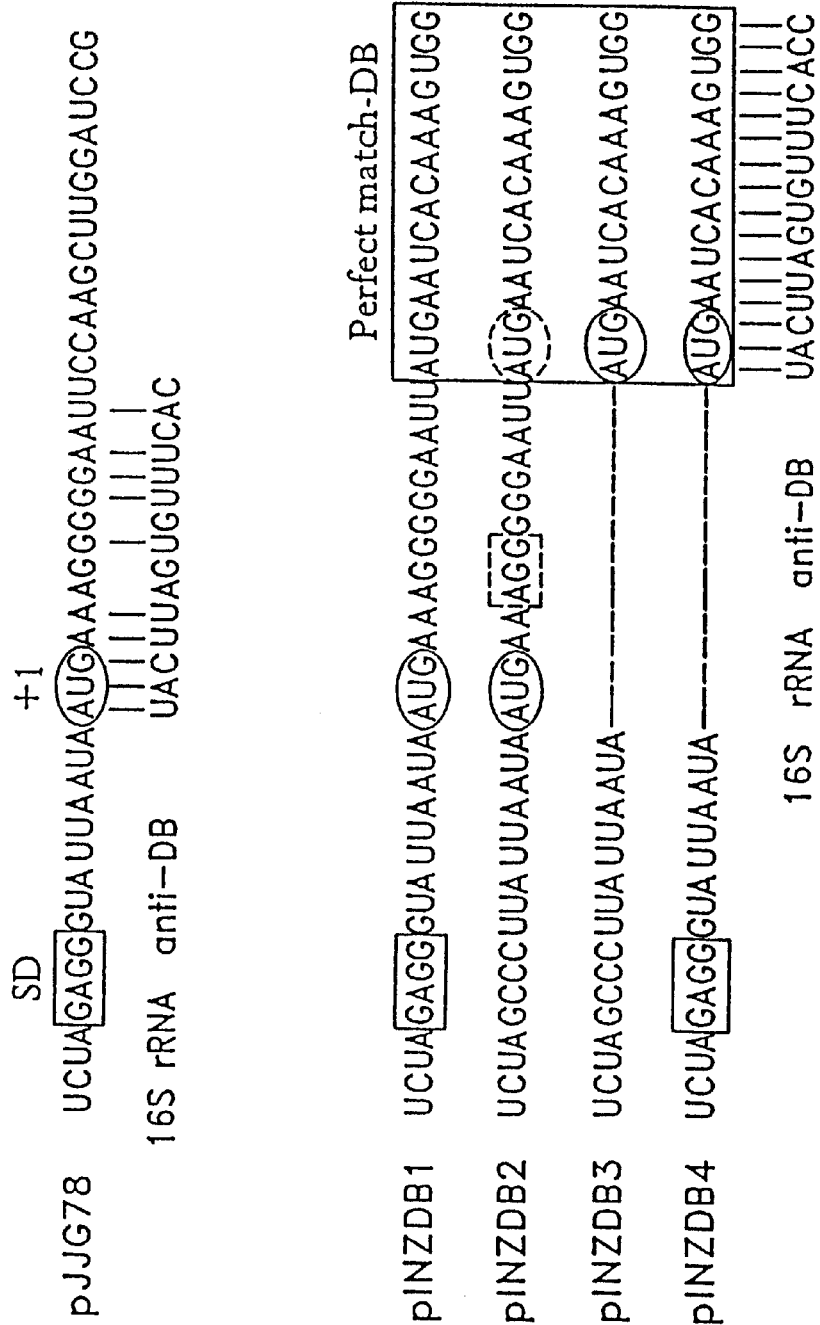

The experiments described above were carried out at 15° C. In order to examine whether DB also works at 37° C., the cspA cold-shock regulatory regions upstream of SD of pJJG78 and pJJG78DB2 were replaced with the constitutive lpp promoter and the lac promoter-operator fragment using a pINIII vector (Inouye, M. 1983), yielding pINZ and pINZDB1, respectively (FIG. 17A). Cells (pcnB⁻) transformed with pINZ or pINZDB1 showed very low β-galactosidase activity in the absence of IPTG, an inducer of the lac promoter (FIG. 1C, time 0). Upon the addition of 1 mM IPTG, β-galactosidase activity was induced in both cells. After 3 hr induction, β-galactosidase activity increased 18 and 37 folds for pINZ and pINZDB1, respectively (FIG. 16C). However, the levels of β-galactosidase activity show a dramatic difference between the two; the activity with DB (pINZDB1) was 34 times higher than that without DB (pINZ), demonstrating that DB functions at 37° C. as well. Specific activities of β-galactosidase produced from vector pINZ and pINZDB1 are almost identical (data not shown) and thus the addition of the 5 amino acid residues in the β-galactosidase sequence of pINZDB1 (due to DB) does not affect the enzymatic activity. Furthermore, the stabilities of β-galactosidase from pINZ and pINZDB1 are also identical with a half-life of approximately 3 hr (data not shown).

Figure 17C:
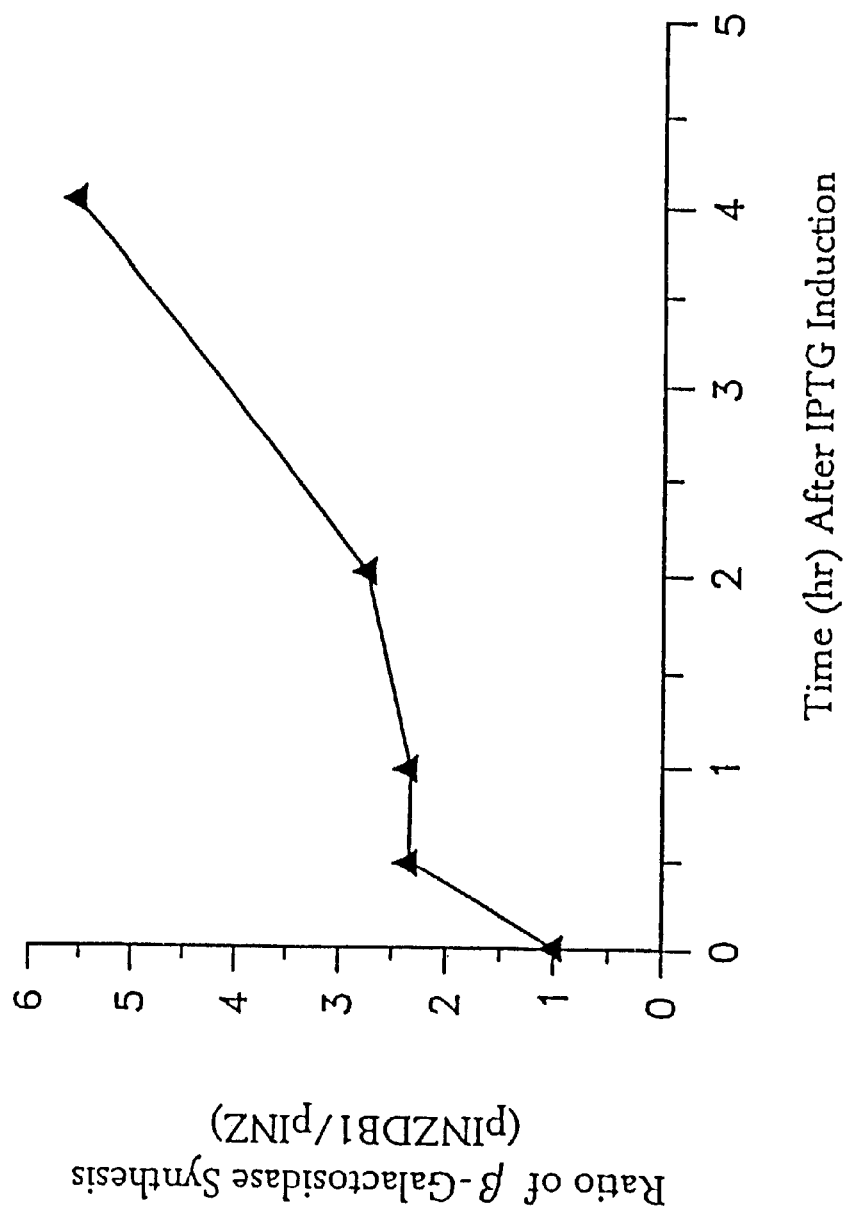

Next, we examined whether DB functions independently from SD, the initial ribosome binding site. For this purpose, the SD sequence of pINZDB1, GAGG was changed to GCCC, yielding pINZDB2 (FIGS. 17A and 17B). The β-galactosidase level of pINZDB2 induction was reduced to ⅐ of that of pINZDB1, but still 3 fold higher than that of pINZ at 3 hr after IPTG induction (FIG. 17C). However, since pINZDB2 has the second AUG codon 6 codons downstream as a result of DB insertion it might serve as a secondary initiation codon for the lacZ gene. Indeed, the N-terminal sequence analysis showed that 100% of the β-galactosidase produced from pINZDB2 is initiated at the second AUG codon as compared with pINZDB1, which is more than 90% initiated at the first AUG codon (data not shown). Furthermore, the second AUG codon is preceded by a potential but poor SD sequence (AAGG) at the region corresponding to the 2nd and 3th codons (underlined; FIG. 17A). Indeed, when this secondary SD was removed by deletion of the 15-base sequence (codon 1 to 5; pINZDB3 in FIG. 17A), β-galactosidase activity at all time points was reduced to the background level (FIG. 17C), indicating that the secondary SD played a crucial role in the translation of the pINZDB2 lacZ mRNA. When the SD sequence was recreated by 5 base substitution in pINZDB3 (pINZDB4; FIG. 17A), β-galactosidase activity of this construct was recovered to a comparable level to that of pINZDB1 (FIG. 17B). It is important to notice that the DB sequence starting from the first AUG codon was eliminated in pINZDB4 (FIG. 17A). Therefore, the high expression of β-galactosidase from pINZDB1 and pINZDB4 is due to the perfectly matching DB sequence (FIG. 17A). These results indicate that (a) DB functions only in the presence of SD, (b) the position of DB is flexible starting from either codon 1 or 6.

Example 13

Enhancement of Translation by DB

The β-galactosidase activity showed in FIG. 17B indicates that DB enhances the translation of pINZDB1. Therefore, in order to test the effect the DB in translation efficiency the rate of β-galactosidase synthesis from pINZ and pINZDB1 was analyzed. The rate of β-galactosidase synthesis was measured by pulse-labeling cells for 5 min with [³⁵S]-methionine after the addition of IPTG using cells harboring pINZ and pINZDB1. After SDS-PAGE, the amounts of radioactive β-galactosidase were estimated using a phosphorimager (FIG. 17D). Prior to the addition of IPTG, the rate of β-galactosidase synthesis from pINZ and pINZDB1 was identical. However, upon IPTG induction the rates of β-galactosidase synthesis from pINZDB1 was continuously increasing at each time point while the rate of β-galactosidase synthesis from pINZ was almost non affected. After 4 hr of IPTG addition the rate of β-galactosidase synthesis from pINZDB1 was 6.5 times higher than that of pINZ. This result demonstrate that DB enhances the translation efficiency of pINZDB1 as reflected by the increment in the synthesis of β-galactosidase.

Figure 18B:
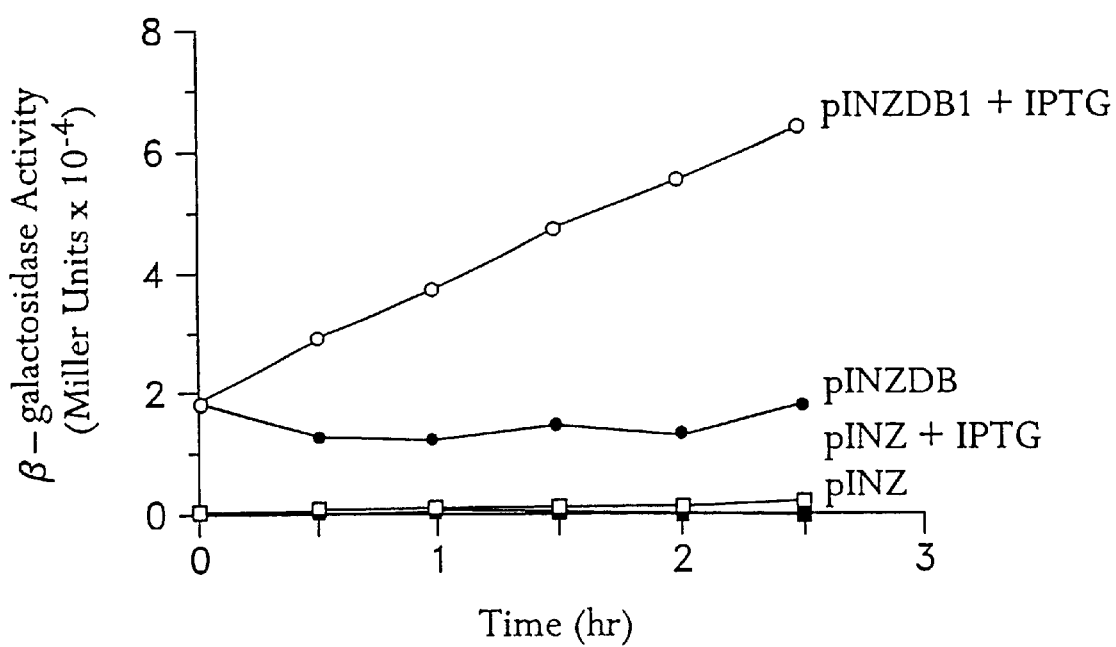

In order to examine whether DB enhances translation initiation we next analyze the ability of lacZ mRNA from pINZ and pINZDB1 to form polysomes. For this experiment, pcnB⁺ cells were used to amplify the effect of DB. Interestingly, cells with pINZDB1 could not form colonies on LB plates in the presence of 1 mM IPTG, while cells with pINZ formed colonies. The lethal effect of IPTG on the cells with pINZDB1 is considered to be due to overexpression of β-galactosidase. After the addition of IPTG, cell growth was stopped by the addition of chloramphenicol (0.1 mg/ml) at 15, 30 and 60 min and then polysome profiles were examined as shown in FIG. 18. From each gradient fraction (500 ml), 200 ml were spotted on a nitrocellulose membrane and the amount of the lacZ mRNA analyzed using a 24-base antisense oligonucleotide (M13-47 oligonucleotide). The amounts of the lacZ mRNA were quantified by a phosphorimager and are displayed in FIG. 18. While the polysome profiles are similar, there are significant differences in the distribution of the lacZ mRNA; at 15 min the lacZ mRNA mainly exists in the upper half of the gradient (fraction 8 to 14, corresponding to 70S to 30S ribosomes) with pINZ, while with pINZDB1 a major peak (fraction 3 to 8) is formed in the lower half of the gradient. At 30 min, the lacZ mRNA from pINZ moved to the position of 70S ribosome, while the lacZ mRNA from pINZDB1 maintained a similar pattern as that at 15 min. At 60 min a major fraction of the lacZ mRNA from pINZ remained in the upper half of the gradient, while the lacZ mRNA from pINZDB1 was broadly distributed from higher order polysomes to 70S ribosome fraction. Therefore, the reason why cells harboring pINZDB1 could not form colonies on LB plates containing 1 mM IPTG may be due to a decrease in the concentration of free ribosomes as a result of the massive expression of a highly translatable DB-containing mRNA (Vind et al., 1993). These results indicate that DB enhances the efficiency of polysome formation probably due to a translation initiation enhancement.

In order to estimate the exact effect of DB from the above experiment, the amount of the lacZ mRNA and the β-galactosidase activity were measured at the same time points taken in the polysome profiles (15, 30 and 60 min after IPTG induction). As shown in FIG. 19A, the amounts of the lacZ mRNA reached almost the maximal level at 15 min for both pINZ and pINZDB1. The phosphorimager analysis of this result revealed that the amounts of the pINZDB1 mRNA are 1.5, 1.4 and 1.3 times higher than those of the pINZ mRNA at 15, 30 and 60 min, respectively. The higher mRNA levels for pINZDB1 are probably attributable to the highly efficient polysome formation of pINZDB1 that may stabilize the mRNA (Iost and Dreyfus 1995). The induction of β-galactosidase activity is shown in FIG. 19B. In the case of pINZDB1, the activity is very high even in the absence of IPTG, and upon the addition of IPTG, it increased from 18,500 to 64,400 units (3.5 fold) after 2.5 hr incubation. In the case of pINZ, the background activity prior to IPTG induction was much lower, and it increased from 900 to 2,900 units (3 fold) at the 2.5 hr time point. The increment of the β-galactosidase activity of pINZDB1 between 30 and 60 min is 35 times higher than that of pINZ, and therefore the efficiency of β-galactosidase production for pINZDB1 is calculated to be 26 times higher than that for pINZ on the bases of the amount of mRNA. Therefore, the higher levels of β-galactosidase production from pINZDB1 are due to a high efficiency of polysome formation.

Next, in order to more directly demonstrate the translation-enhancement effect of DB the β-galactosidase synthesis was examined in a cell-free system using pINZ and pINZDB1. The [$^{35}$S]methionine incorporation into β-galactosidase (band G) with pINZDB1 (lane 2, FIG. 19) was 8 fold higher than that with pINZ (lane 1), while the β-lactamase (band L) production was almost identical in both lanes.

It has been proposed that in the absence of ribosomal protein S2, structural changes in 16S rRNA result in the release of the anti-DB sequence from the penultimate stem making it more accessible to base-pair with DB (Shean and Gottesman 1992; Powers et al., 1988). We analyzed the β-galactosidase expression of pINZ, pINZDB1 in *E. coli* CS239 that carries a S2 temperature-sensitive mutation (Shean and Gottesman, 1992). FIG. 20A shows that the β-galactosidase activity of pINZDB1 significantly increases upon shifting the temperature from 30 to 42° C. in the $S2^{ts}$ strain (CS239) (6.3 fold from 0 to 3.5 hr), while the activity in the type strain (CS240) slightly increased (1.1 fold from 0 to 3.5 hr). If the initial ratio of the activity of CS239 to that of CS240 at time 0 is taken as one, the ratio dramatically increased, reaching 5.8 at 3.5 hr after temperature shift (FIG. 21B). In contrast, the lacZ gene without DB did not show any significant differences in its expression between CS240 and CS239, and the ratios of the activity of CS239 to that of CS240 remained also at the initial level throughout the incubation time (FIG. 21B). A similar experiment was carried out with pINZDB3 (SD$^-$, DB$^+$), and the ratio of the activity in CS239 to that in CS240 increased 3.4 fold at 3.5 hr after the temperature shift (data not shown). These results clearly demonstrate that the low levels of S2 protein at 42° C. causes significant stimulation of the lacZ expression only if the lacZ gene contains DB, consistent to the proposal of Shean and Gottesman (1992).

Sequence comparison among CspA, CspB, CspG, and CspI. The *E. coli* genome-sequencing project has revealed the ninth member of the CspA family, which we designated CspI. CspI shows the highest identity to CspG (79%) (FIG. 21A), and on the phylogenetic tree it belongs to the same group as CspA, CspB, and CspG, all of which are cold shock inducible as described previously. The three-dimensional structure of CspA has been determined. It consists of five antiparallel-strands forming a -barrel structure with two-sheets. CspI contains well-conserved hydrophobic residues including V9, 121, V30, V32, and V51 (FIG. 21A), which form a hydrophobic core in CspA. In addition, two RNA binding motifs, RNP1 and RNP2, are well conserved in CspI (FIG. 21A). These facts suggest that CspI may form a conformation similar to that of CspA and may also bind to RNA and single-stranded DNA, as CspA does.

FIG. 21A and 21B show a sequence comparison of four cold shock-inducible members of the *E. coli* CspA family. Part A shows amino acid sequence alignments of CspI (SEQ ID NO. 79), CspG (SEQ ID NO. 80), CspB (SEQ ID NO. 81), and CspA (SEQ ID NO. 82). Residues identical to CspI are shown as dots. The residues forming the hydrophobic core in the β-barrel structure are indicated by solid circles above the sequences. The RNA binding motifs, RNP1 and RNP2, are boxed. Their amino acid sequence homologies are shown on the right, with CspI set at 100%. Part B shows sequence alignment of the promoter, 5'-UTR, and the first 13 codon nucleotides of cspI, cspG, cspB, and cspA. Nucleotides identical to cspI are shown as dots. To maximize the alignment, some gaps have been introduced; these are indicated by dashes. The transcription start sites are in bold letters and are marked as +1. The translation start codon ATGs are also in bold letters and are underlined. The most homologous sequences (UP element, −35 region, −10 region, cold box, upstream sequence, Shine-Dalgarno [SD] sequence, and downstream box) are boxed and labeled above the boxes.

Cold Shock-inducible Expression of cspI.

The cspI gene is located at 35.2 min on the *E. coli* chromosome and transcribed counterclockwise. To determine the regulation of cspI expression, the 387-bp DNA fragment containing the 346-bp upstream sequence of the cspI coding region and the region for the first 13 codons of cspI was amplified and cloned, to translationally and transcriptionally fuse to lacZ on pRS414 and pRS415, yielding pNWI3 and pNWI4, respectively. These fusion constructs were introduced into AR134, and the β-galactosidase activity was measured. AR134 is a pcnB mutant, which keeps pBR322 derivatives at low copy number to minimize any positive or negative effects of the multicopy plasmids on cspI-lacZ expression.

FIG. 22 shows cold shock induction of β-galactosidase activity. Strain AR134, harboring various plasmids, was grown to mid-log phase at 37° C. in LB medium containing ampicillin (50 μg/ml) and then transferred to 15° C. Samples were taken at 0, 1, 2, 3, and 5 h after the temperature downshift, and β-galactosidase activity was measured. The assay was carried out at least in duplicate at each time point. Symbols: ○, pNWI3; ●, pNWI4; □, pCspA-LacZ; Δ, pRS414.

β-Galactosidase activities of both fusion constructs were very low at 37° C. at mid-log phase (zero time point in FIG. 22). Since cspI shows the highest identity to cold shock-inducible CspG, we analyzed the effect of temperature downshift on cspI-lacZ expression. After the temperature downshift from 37 to 15° C., the β-galactosidase activities of both the transcriptional and the translational fusion constructs dramatically increased and were both approximately twofold higher than that of the cspA-lacZ translational fusion, as shown in FIG. 22, indicating that cspI is a cold shock-inducible gene like cspA, cspB, and cspG.

FIG. 23 shows primer extension analysis of the cspI mRNA. Strain JM83 was grown in LB medium at 37° C. RNA extraction and primer extension analysis were carried out as described in Materials and Methods. The primer corresponds to the complementary strand for codons 14 to 19 of cspI. Lanes: 1, without RNA; 2, with RNA extracted from exponentially growing cells at 37° C.; 3, with RNA extracted from cells at 0.5 h after the temperature downshift to 15° C.; 4, with RNA extracted from cells at 3 h after the shift; 5, with RNA extracted from stationary-phase cells at 37° C. Primer extension products were analyzed on a denatured polyacrylamide gel together with a sequencing ladder. The sequence is shown at the right; the arrow indicates the transcription start site.

Although the expression of cspA, cspB, cspG, and cspI is cold shock inducible and the primary amino acid sequence of CspI is highly homologous to those of CspA, CspB, and CspG, a putative 5'-UTR sequence for cspI does not show high similarity to those for cspA, cspB, and cspG, suggesting that cspI might be regulated somewhat differently. To identify the 5'-UTR of cspI, the transcription start site of cspI was determined by primer extension analysis with primer 8272, which is specific for cspI. This primer corresponds to the complementary strand for cspI codons 14 through 19. Total RNA of strain JM83 was extracted from cells grown at 37° C. and from cells grown for 0.5 and 3 h after the temperature downshift to 15° C. Primer extension products of cspI from pre-cold-shocked cells were hardly detected (FIG. 23, lane 2). However, at 0.5 h after the temperature downshift, the amounts of primer extension products dramatically increased (lane 3), indicating that the amount of cspI mRNA greatly increased upon cold shock. At 3 h after the temperature downshift, the amount of cspI mRNA was reduced to a new basal level (lane 4), which is slightly higher than that at 37° C. The pattern of cold shock induction of the cspI mRNA is very similar to those of the cspA, cspB, and cspG mRNAs, indicating that cspI is also transiently induced upon cold shock. The cspI mRNA was not induced during stationary phase at 37° C. (lane 5).

On the basis of the primer extension experiment described above, the possible transcription start site and the deduced promoter region, the −35 and −10 sequences (TTGCTA and GTTAAT, respectively) are identified as shown in FIG. 21B. The promoter sequence of cspI is very similar to those of cspA, cspB, and cspG. Upstream of the −35 region of cspA, cspB, and cspG is an AT-rich region called the UP element, which is believed to play an important role in maintaining the high promoter activity of cspA at both 37 and 15° C. The UP element also exists in the cspI gene and is likely to play an important role in cspI transcription at low temperature.

The primer extension experiment (FIG. 23) also reveals that the cspI mRNA contains a long 5'-UTR consisting of 145 bases, which is comparable to the 5'-UTRs of cspA (159 bases), cspB (161 bases), and cspG (156 bases). Although the sequence of the 5'-UTR of cspI is not highly homologous to those of cspA, cspB, and cspG, the 5'-UTR of cspI still contains a well-conserved motif, termed the cold box, which is believed to be involved in autoregulation at the end of the acclimation phase (6, 14, see below). Farther downstream in the 5'-UTR, there is a 12-base conserved sequence designated the upstream sequence, which may be involved in the translation efficiency of cspA. It should be noted that cspA, cspB, and cspG all have a downstream box downstream of the translation initiation codon, which has been shown to play an important role in cold shock induction at the level of translation. As shown in FIG. 21B, cspI has exactly the same downstream box as cspB and cspG, suggesting that the cspI downstream box also plays an essential role in translation at low temperature.

cspI mRNA Stabilization Upon Cold Shock.

Based on the analysis of the cspI-lacZ fusion constructs, cspI expression seems to be regulated by transcription and/or mRNA stability (FIG. 22). It has been shown that mRNA stability plays a critical role in the cold inducibility of cspA and that the stability of mRNA is regulated by its long 5'-UTR. Therefore, we examined the stability of the cspI mRNA at both 37 and 15° C. by primer extension analyses. As shown in FIG. 24, the cspI mRNA was very unstable at 37° C., with a half-life of approximately 30 s, somewhat more stable than the cspA mRNA (half-life, approximately 20 s). However, at 1 h after the temperature downshift, the cspI mRNA and the cspA mRNA were stabilized with half-lives of 14 and 12 min, respectively. These results suggest that mRNA stability also plays a major role in the cold shock induction of cspI.

FIG. 24 shows an analysis of mRNA stability. A culture of strain JM83 grown in LB medium at 37° C. was shifted to 15° C. Part A shows measurement of mRNA stability at 37° C. A culture preincubated at 15° C. for 30 min was shifted back to 37° C. Rifampin was added to the culture to a final concentration of 200 μg/ml at the point of the temperature upshift. RNAs were extracted at 0 (lanes 1 and 6), 1 (lanes 2 and 7), 2 (lanes 3 and 8), 3 (lanes 5 and 10) min after the addition of rifampin. Part B shows measurement of the mRNA stability at 15° C. Rifampin was added 1 h after the temperature downshift and RNAs were extracted at 0 (lanes 1 and 6), 5 (lanes 2 and 7), 10 (lanes 3 and 8), 20 (lanes 4 and 9), and 30 (lanes 5 and 10) min after the addition of rifampin. Primer extension was carried out with a primer for cspI (lanes 1 to 5) and with a primer for cspA (lanes 6 to 10) as described in Materials and Methods. Panels C and D show graphical presentations based on the results obtained in panels A and B, respectively. The radioactivities of primer extension products were measured and plotted, with the product at time zero set to 100%. Symbols used in the figure represent: ○, cspI; ●, cspA.

When the 5'-UTR of the cspA mRNA was deleted, cspA expression was observed even at 37° C., indicating that the 5'-UTR has a negative effect on cspA expression at 37° C. To elucidate the effect of cspI 5'-UTR on cspI expression, another transcriptional cspI-lacZ fusion construct, pNWI5, which does not contain the 5'-UTR, was prepared. At 37° C., the β-galactosidase activity in the cells harboring pNWI5 was 980 U, which was much higher than that in the cells harboring pNWI4 (29 U), which contains the 5'-UTR. This indicates that the cspI 5'-UTR has a negative effect on its own gene expression at 37° C., as the cspA 5'-UTR does.

CspI induction at lower temperatures. CspA, CspB, CspG, and CspI are all cold shock inducible. However, upon cold shock, the temperature dependence of CspA induction is broader while that of CspB and CspG is restricted to lower temperatures and to a narrower temperature range. To examine the optimal temperature for CspI induction, two-dimensional (2D) gel electrophoresis was carried out with cells labeled with [$^{35}$S]methionine at different temperatures. For this purpose, we first determined the spot corresponding to CspI by using a plasmid which overproduces CspI. As shown in FIG. 25A, CspI migrated very close to CspB and its production was indeed induced upon cold shock.

FIG. 25 shows an analysis of CspI protein by 2D gel electrophoresis. Panel A shows cultures of strain JM83 harboring pUC19 or pNWI2 were labeled with [$^{35}$S] methionine at 37° C. and labeled 30 min after the temperature downshift to 15° C. Total-cell extracts were analyzed by 2D gel electrophoresis, and autoradiograms were obtained. Only a portion corresponding to low-molecular-weight proteins is shown. (B) Cultures of strain JM83 were labeled with [$^{35}$S]methionine 30 min after the temperature downshift from 37° C. to 30, 25, 20, 15, and 10C, and the one indicated by "15° C. 3 hr" is a sample labeled at 3 h after the temperature downshift to 15° C. CspI is indicated by an arrowhead. The positions of CspA, CspB, and CspG are shown by labeled arrowheads in one of the panels in A and B: 1, CspA; 2, CspB; 3, CspG; and 4, CspI.

CspI production from the chromosomal cspI gene could not be detected at 37° C. but became clearly detectable at 15° C. (FIG. 25B), unambiguously demonstrating that cspI is a cold shock-inducible gene. Next, cells grown at 37° C. to mid-log phase was transferred to different temperatures, i.e., 30, 25, 20, 15, and 10° C. At 30 min after the temperature shift, cells were labeled with [$^{35}$S]methionine for 30 min and total cellular proteins were analyzed by 2D gel electrophoresis. In contrast to CspA, CspB, and CspG, cspI was induced only when the temperature was shifted to or below 15° C. (FIG. 25B), indicating that CspI has the narrowest and lowest temperature range for its induction. CspI production was reduced to a lower level at 3 h after the temperature downshift, as can be seen from the gel (FIG. 25B), which is in good agreement with the results of the primer extension analysis as shown in FIG. 23. This indicates that CspI production is transiently induced during the acclimation phase upon cold shock, as for CspA, CspB, and CspG.

It is interesting that the rate of CspI synthesis is much lower than that of CspA (FIG. 25), although the β-galactosidase activity of the cspI-lacZ translational fusion construct is higher than that of the cspA-lacZ translational fusion construct (FIG. 22). In both fusion constructs, the first 13 codons of cspI or cspA were translationally fused to lacZ as mentioned above. Since transcription initiation and translation initiation from the fusion constructs are likely to occur in the same manner as those from the chromosomal copy of cspA and cspI, we examined any difference in protein stability between CspA and CspI. Their half-lives were measured by pulse-chase experiments 30 min after the temperature downshift and found to be longer than 5 h, although CspI was somewhat less stable than CspA (data not shown). The chasing in the 2D electrophoresis in FIG. 25 was only 5 min. Therefore, it is unlikely that the low production of CspI is due to protein stability. These results therefore suggest that the difference between CspA and CspI production at low temperature may be at the level of translation elongation.

Derepression by overexpression of the cspA or cspI 5'-UTR. It has been reported that when the cspA 5'-UTR was overproduced during cold shock treatment, CspA and CspB expression were no longer transient and a high level of CspA and CspB expression was still observed after the acclimation phase. This phenomenon, called derepression, was also observed when the region from +1 to +25 of the cspA 5'-UTR was overexpressed. Within this region, a highly conserved sequence, designated the cold box sequence, was found (FIG. 21B). Conversely, deletion of the cold box region abolished the derepression effect of the cspA 5'-UTR. It has been proposed that a factor might bind to the cold box to repress the cspA expression at the level of transcription at the end of the acclimation phase. The overproduction of the 5'-UTR containing the cold box is thus expected to sequester this factor to derepress cspA expression.

Figure 26B:
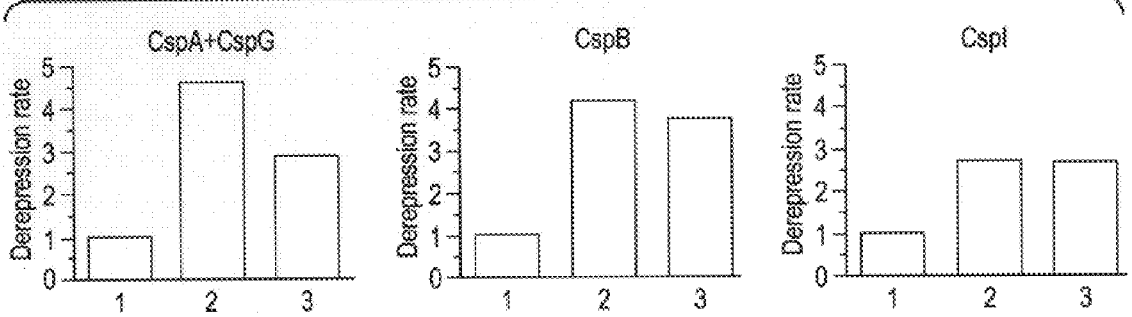

As mentioned above, the cspI 5'-UTR possesses a cold box sequence. To investigate whether the cspI cold box has a similar effect as that of cspA, we constructed a plasmid pNW16 that is able to overexpress the cspI 5'-UTR from +1 to +113. By primer extension analysis, we confirmed that the cspI 5'-UTR was effectively overexpressed (data not shown). pUC19-600 that can overexpress the cspA 5'-UTR (14) was used as a positive control, and pUC19 was used as a negative control. Before and at 1 h after temperature downshift, the patterns of CspA, CspB, CspG, and CspI expression were essentially the same among cells harboring pUC19, pUC19-600, and pNWI6 (FIG. 26A, panels a to f). At 3 h after the temperature downshift, all four proteins were greatly repressed in cells harboring pUC19 (FIG. 26A, panel G) while production of all four proteins became derepressed in cells overexpressing either the cspA or the cspI 5'-UTR (FIG. 26A, panels h and i, respectively). As shown in FIG. 26B, overexpression of both the cspA and the cspI 5'-UTRs has a derepression effect, although the effect of the cspI 5'-UTR is weaker than that of the cspA 5'-UTR. These results suggest that the cspI 5'-UTR probably plays a role in the autoregulation of the cspI gene at the end of the acclimation phase.

FIG. 26 shows the effect of cspI 5'-UTR overexpression on CspA, CspB, CspG, and CspI expression. Panel A shows cultures of strain JM83 harboring pUC19 (a, d, and g), pUC19-600 (b, e, and h), or pNWI6 (c, f, and i) were labeled with [$^{35}$S]methionine at 37° C. (a, b, and c), and at 1 h (d, e, and f) and 3 h (g, h, and i) after the temperature downshift to 15° C. Total-cell extracts were analyzed by 2D gel electrophoresis, and autoradiograms were obtained. Only a portion corresponding to low-molecular-weight proteins is shown. The cold shock proteins are indicated: 1, CspA; 2, CspB; 3, CspG; 4, cspI. Panel B shows the amounts of the four proteins were quantitated with a phosphorimager, with ribosomal protein L11 as a reference. The amounts of the proteins at each time point upon cold shock are given as the ratio to the amount of the L11 spot. Since the CspA and CspG spots are not separated, we counted them together. The ratio of the amount of protein at 1 h upon cold shock to that at 3 h upon cold shock is its repression rate. The derepression rate is the ratio of repression rate in control cells to that in the 5'-UTR overexpression cells. Lanes: 1, control cells; 2, cells overproducing cspA 5'-UTR; 3, cells overproducing cspI 5'-UTR.

The following conclusions are offered: *E. coli* has nine csp genes, cspA to cspI Of these, cspA, cspB, cspG, and cspI are cold shock inducible. All these csp genes share several important features. (i) They all contain a UP element immediately upstream of the promoter, which contributes to maintain the high promoter activity even at low temperatures. (ii) They all contain a long 5'-UTR in their mRNAs (159, 161, 156, and 145 bases for cspA, cspB, cspG, and cspI, respectively). As found for the cspA mRNA (22), these 5'-UTRs are believed to exert a negative effect on their expression at 37° C., while they cause a positive effect on their cold shock inducibility. (iii) They all have the cold box at the 5'-end region of their 5'-UTRs, which plays a role in autoregulation to repress their own gene expression at the end of the acclimation phase. (iv) They all contain a downstream box downstream of the translation initiation codon, which plays an essential role in the cold shock induction by enhancing translation. Taken together, expression of all four csp genes appears to be regulated essentially in the same manner. It should be mentioned, however, that the optimal temperature ranges for the induction of these genes are different. CspI is induced at a relatively lower temperature range than the others.

We claim:

1. An isolated nucleic acid molecule that prolongs the expression of cold shock inducible genes under conditions that elicit the cold shock response in a bacterium, said nucleic acid molecule comprising the 5'-UTR of cspI operably linked to a non-native promoter.

2. The isolated nucleic acid molecule of claim 1, wherein said cold shock inducible gene interacts with CspI protein.

3. The isolated nucleic acid molecule of claim 1, wherein said nucleic acid molecule is placed in a recombinant expression vector, and wherein said recombinant expression vector further comprises a translation enhancer, a downstream box, and a heterologous gene, and wherein the nucleic acid molecule directs prolonged expression and enhanced translation of the heterologous gene under conditions that elicit a cold shock response in bacterium.

4. The isolated nucleic acid molecule of claim 1 wherein said non-native promoter is LacZ.

5. An isolated nucleic acid molecule that prolongs the expression of cold shock inducible genes under conditions that elicit the cold shock response in a bacterium, said nucleic acid molecule comprising a cold box of cspI, wherein said nucleic acid molecule includes not more than 998 base pairs.

6. The nucleic acid molecule of claim 2, wherein said cold box consists of nucleotides +3 to +18 of the csp 5'-UTR (nucleotides 59–74 of SEQ ID NO: 83).

7. A nucleic acid construct for regulation of the expression of cold shock inducible genes to elicit the cold shock response in bacterium, said nucleic acid construct comprising the 5'-UTR of cspI operably linked to a promoter, wherein said promoter is functional under conditions of physiological stress.

8. An isolated nucleic acid molecule that prolongs the expression of cold shock inducible genes under conditions that elicit the cold shock response in a bacterium, said nucleic acid molecule comprising a cold box of cspI, wherein said nucleic acid molecule includes not more than 346 base pairs.

9. An isolated nucleic acid molecule that prolongs the expression of cold shock inducible genes under conditions that elicit the cold shock response in a bacterium, said nucleic acid molecule comprising a cold box of cspI, wherein said nucleic acid molecule includes not more than 387 base pairs.

* * * * *

SEQUENCE LISTING

```
<160> NUMBER OF SEQ ID NOS: 87

<210> SEQ ID NO 1
<211> LENGTH: 14
<212> TYPE: RNA
<213> ORGANISM: Artificial Sequence
<220> FEATURE:
<223> OTHER INFORMATION: Description of Artificial Sequence: ADB

<400> SEQUENCE: 1
acuuugugau ucau                                                       14

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: DB

<400> SEQUENCE: 2
augacuggua ucgu                                                       14

<210> SEQ ID NO 3
<211> LENGTH: 14
<212> TYPE: RNA
<213> ORGANISM: Artificial Sequence
<220> FEATURE:
<223> OTHER INFORMATION: Description of Artificial Sequence: DB

<400> SEQUENCE: 3
augacugguu ucgu                                                       14

<210> SEQ ID NO 4
<211> LENGTH: 14
<212> TYPE: RNA
<213> ORGANISM: Artificial Sequence
<220> FEATURE:
<223> OTHER INFORMATION: Description of Artificial Sequence: DB

<400> SEQUENCE: 4
augacugguu uagu                                                       14

<210> SEQ ID NO 5
<211> LENGTH: 14
<212> TYPE: RNA
<213> ORGANISM: Artificial Sequence
<220> FEATURE:
<223> OTHER INFORMATION: Description of Artificial Sequence: DB

<400> SEQUENCE: 5
augaguuaug uaga                                                       14

<210> SEQ ID NO 6
<211> LENGTH: 14
```

```
<212> TYPE: RNA
<213> ORGANISM: Artificial Sequence
<220> FEATURE:
<223> OTHER INFORMATION: Description of Artificial Sequence: DB

<400> SEQUENCE: 6
auggcgaaaa gaau                                                    14

<210> SEQ ID NO 7
<211> LENGTH: 47
<212> TYPE: RNA
<213> ORGANISM: Artificial Sequence
<220> FEATURE:
<223> OTHER INFORMATION: Description of Artificial Sequence: DB
<223> OTHER INFORMATION: "n" bases may be g, c, u or a and may range
      from 0 to 30

<400> SEQUENCE: 7
augnnnnnnn nnnnnnnnnn nnnnnnnnnn nnnaugacug guaucgu                47

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: DB
<223> OTHER INFORMATION: "n" bases may be g, g, t or a and may range
      from 0 to 30

<400> SEQUENCE: 8
atgnnnnnnn nnnnnnnnnn nnnnnnnnnn nnatgactg gtatcgt                 47

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gccgaaaggc aca                                                     13

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
acggttctag acgta                                                   15

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 11
cggcattaag taagcagttg                                              20

<210> SEQ ID NO 12
<211> LENGTH: 33
<212> TYPE: DNA
```

```
<213> ORGANISM: Artificial Sequence
<220> FEATURE:
<223> OTHER INFORMATION: Description of Artificial Sequence: primer

<400> SEQUENCE: 12
ctggatcctt taatggtctg tacgtcaaac cgt                             33

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 13
cggaattcag cctgtaatct ct                                         22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14
ctgtcgactt acttacggcg ttgc                                       24

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gacaggatta aaaatcgag                                             19

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 16
aaccgttgat gtgca                                                 15

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 17
ccttgctagc cgattaatca taaatatg                                   28

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 18
ccggatccag gttgaaccat ttt                                        23
```

```
<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 19
actacacttt gatgtgcatt agc                                              23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 20
caacgataag ctttaatggt ctgt                                             24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 21
taaaggctct tgaagggact t                                                21

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 22
cggcgatata atgtgcacta cgaggg                                           26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 23
tacctttaag gcgtgcttta cagatt                                           26

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 24
gcacatcaaa gtgtagtaag gcaa                                             24

<210> SEQ ID NO 25
<211> LENGTH: 21
<212> TYPE: DNA
<213> ORGANISM: Artificial Sequence
<220> FEATURE:
```

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25
taaagcttat cgttgatacc c                                             21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 26
tcaagagcct ttaacgcttc aaaa                                          24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 27
gcacattata tcgccgaaag gc                                            22

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 28
aaagcacgcc ttaaaggtaa tacact                                        26

<210> SEQ ID NO 29
<211> LENGTH: 53
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
ctagccgaaa ggcacaaatt aagagggtat taataatgaa aggggaatt cca           53

<210> SEQ ID NO 30
<211> LENGTH: 53
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
agcttggaat tcccccttc attattaata ccctcttaat ttgtgccttt cgg           53

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31

-continued aattaatcac aaagtggg                                            18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
aattcccact ttgtgatt                                            18

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
aattatgaat cacaaagtgg g                                        21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
aattcccact ttgtgattca t                                        21

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35 ctagcccctta ttaataatga aagggggaat tatgaatcac aaagtggg          48

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
aattcccact ttgtgattca taattccccc tttcattatt aataaggg           48

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37 ctagcccctta ttaataatga atcacaaagt ggg                          33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
aattcccact ttgtgattca ttattaataa ggg           33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
ctagagggta ttaataatga atcacaaagt ggg           33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
aattcccact ttgtgattca ttattaatac cct           33

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
cgccagggtt ttcccagtca cgac           24

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence:
      oligonucleotide
<221> NAME/KEY: modified_base
<222> LOCATION: (6)
<223> OTHER INFORMATION: a to t
<221> NAME/KEY: modified_base
<222> LOCATION: (7)
<223> OTHER INFORMATION: t to c
<221> NAME/KEY: modified_base
<222> LOCATION: (10)
<223> OTHER INFORMATION: a to g

<400> SEQUENCE: 42
aatttnntan aggtaa           16

<210> SEQ ID NO 43
<211> LENGTH: 23
<212> TYPE: DNA

-continued

```
<213> ORGANISM: Artificial Sequence
<220> FEATURE:
<223> OTHER INFORMATION: Description of Artificial Sequence:
      oligonucleotide

<400> SEQUENCE: 43
ccggatccag ctttaatata gct                                           23

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
ccggatccag atttgacatt ctaca                                         25

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
ccggatccag gttaaaccat ttt                                           23

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
ccggatccag acctttatca gcgtt                                         25

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
gaaaggctca agttacttca tgtagaatg                                     29

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
cattctacat gaagtaactt gagcctttc                                     29

<210> SEQ ID NO 49
<211> LENGTH: 26
<212> TYPE: DNA
<213> ORGANISM: Artificial Sequence
```

```
<220> FEATURE:
<223> OTHER INFORMATION: Description of Artificial Sequence: primer

<400> SEQUENCE: 49
aagaattcaa catttacatc gcggaa                                          26

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 50
ttgggatcct caaagcgcca cta                                             23

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 51
gggggatccg ggttaaacca tttcact                                         27

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 52
ggggatccag aacaccatta acgc                                            24

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 53
ccaaaacctt tttcaggg                                                   18

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 54
acatagtgta ttacctttaa                                                 20

<210> SEQ ID NO 55
<211> LENGTH: 13
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 55
gccgaaaggc uca                                                        13
```

<210> SEQ ID NO 56
<211> LENGTH: 13
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
gccgaaaggc cca                                                          13

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
gcccaagggc ta                                                           12

<210> SEQ ID NO 58
<211> LENGTH: 47
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 58
uugacaucca cggaaguuuu cagagaugag aaugugccuu cgggaac                     47

<210> SEQ ID NO 59
<211> LENGTH: 40
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 59
gccgaaaggc acacuuaauu auuaaaggua auacacuaug                             40

<210> SEQ ID NO 60
<211> LENGTH: 32
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 60
gccgaaaggc ucaaguuaag gaauguagaa ug                                     32

<210> SEQ ID NO 61
<211> LENGTH: 34
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 61
gccgaaaggc ccaaaaugaa ggaaguaaaa uaug                                   34

<210> SEQ ID NO 62
<211> LENGTH: 162
<212> TYPE: RNA
<213> ORGANISM: Artificial Sequence
<220> FEATURE:
<223> OTHER INFORMATION: Description of Artificial Sequence: deletion
      construct

<400> SEQUENCE: 62
acgguuugac guacagacca uuaaagcagu guaguaaggc aagucccuuc aagaguuauc      60
guugauaccc cucguagugc acauuccuuu aacgcuucaa aaucuguaaa gcacgccaua    120
ucgccgaaag gcacacuuaa uuauuaaagg uaauacacua ug                       162

<210> SEQ ID NO 63
<211> LENGTH: 136
<212> TYPE: RNA
<213> ORGANISM: Artificial Sequence
<220> FEATURE:
<223> OTHER INFORMATION: Description of Artificial Sequence: deletion
      construct

<400> SEQUENCE: 63
aaguguagua aggcaagucc cuucaagagu uaucguugau accccucgua gugcacauuc      60
cuuuaacgcu ucaaaaucug uaaagcacgc cauaucgccg aaaggcacac uuaauuauua    120
aagguaauac acuaug                                                    136

<210> SEQ ID NO 64
<211> LENGTH: 134
<212> TYPE: RNA
<213> ORGANISM: Artificial Sequence
<220> FEATURE:
<223> OTHER INFORMATION: Description of Artificial Sequence: deletion
      construct

<400> SEQUENCE: 64
acgguuugac guacagacca uuaaagcuua ucguugauac cccucguagu gcacauuccu      60
uuaacgcuuc aaaaucugua aagcacgcca uaucgccgaa aggcacacuu aauuauuaaa    120
gguaauacac uaug                                                      134

<210> SEQ ID NO 65
<211> LENGTH: 131
<212> TYPE: RNA
<213> ORGANISM: Artificial Sequence
<220> FEATURE:
<223> OTHER INFORMATION: Description of Artificial Sequence: deletion
      construct

<400> SEQUENCE: 65
acgguuugac guacagacca uuaaagcagu guaguaaggc aagucccuuc aagagcuuua      60
acgcuucaaa aucuguaaag cacgccauau cgccgaaagg cacacuuaau uauuaaaggu    120
aauacacuau g                                                         131

<210> SEQ ID NO 66
<211> LENGTH: 130
<212> TYPE: RNA
<213> ORGANISM: Artificial Sequence
<220> FEATURE:
<223> OTHER INFORMATION: Description of Artificial Sequence: deletion
      construct

<400> SEQUENCE: 66

```
acgguuugac guacagacca uuaaagcagu guaguaaggc aagucccuuc aagaguuauc      60
guugauaccc cucguagugc acauuauauc gccgaaaggc acacuuaauu auuaaaggua     120
auacacuaug                                                           130
```

<210> SEQ ID NO 67
<211> LENGTH: 136
<212> TYPE: RNA
<213> ORGANISM: Artificial Sequence
<220> FEATURE:
<223> OTHER INFORMATION: Description of Artificial Sequence: deletion
      construct

<400> SEQUENCE: 67

```
acgguuugac guacagacca uuaaagcagu guaguaaggc aagucccuuc aagaguuauc      60
guugauaccc cucguagugc acauuccuuu aacgcuucaa aaucuguaaa gcacgccuua    120
aagguaauac acuaug                                                    136
```

<210> SEQ ID NO 68
<211> LENGTH: 65
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 68

```
uuaaggaaug uagaauguca aauaaaauga cugguuuagu aaaaugguuu aacgcugaua     60
aaggu                                                                65
```

<210> SEQ ID NO 69
<211> LENGTH: 39
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 69

```
cuuaaccuuc gggagggcgc uuaccacuuu gugauucau                            39
```

<210> SEQ ID NO 70
<211> LENGTH: 15
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 70

```
uacuuagugu uucac                                                      15
```

<210> SEQ ID NO 71
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 71

```
aaucacaaag ug                                                         12
```

<210> SEQ ID NO 72

```
<211> LENGTH: 15
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 72
augaaucaca aagug                                                  15

<210> SEQ ID NO 73
<211> LENGTH: 47
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 73
ucuagagggu auuaauaaug aaaggggggaa uuccaagcuu ggauccg              47

<210> SEQ ID NO 74
<211> LENGTH: 48
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 74
ucuagagggu auuaauaaug aaaggggggaa uuaugaauca caaagugg             48

<210> SEQ ID NO 75
<211> LENGTH: 48
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 75
ucuagcccuu auuaauaaug aaaggggggaa uuaugaauca caaagugg             48

<210> SEQ ID NO 76
<211> LENGTH: 33
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 76
ucuagcccuu auuaauaaug aaucacaaag ugg                              33

<210> SEQ ID NO 77
<211> LENGTH: 33
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 77
ucuagagggu auuaauaaug aaucacaaag ugg                              33

<210> SEQ ID NO 78
<211> LENGTH: 16
```

```
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 78
uacuuagugu uucacc                                                    16

<210> SEQ ID NO 79
<211> LENGTH: 70
<212> TYPE: PRT
<213> ORGANISM: E. coli

<400> SEQUENCE: 79
```

Met Ser Asn Lys Met Thr Gly Leu Val Lys Trp Phe Asn Pro Glu Lys
 1               5                  10                  15

Gly Phe Gly Phe Ile Thr Pro Lys Asp Gly Ser Lys Asp Val Phe Val
            20                  25                  30

His Phe Ser Ala Ile Gln Ser Asn Asp Phe Lys Thr Leu Thr Glu Asn
        35                  40                  45

Gln Glu Val Glu Phe Gly Ile Glu Asn Gly Pro Lys Gly Pro Ala Ala
    50                  55                  60

Val His Val Val Ala Leu
65                  70

```
<210> SEQ ID NO 80
<211> LENGTH: 70
<212> TYPE: PRT
<213> ORGANISM: E. coli

<400> SEQUENCE: 80
```

Met Ser Asn Lys Met Thr Gly Leu Val Lys Trp Phe Asn Ala Asp Lys
 1               5                  10                  15

Gly Phe Gly Phe Ile Thr Pro Asp Asp Gly Ser Lys Asp Val Phe Val
            20                  25                  30

His Phe Thr Ala Leu Gln Ser Asn Glu Phe Arg Thr Leu Asn Glu Asn
        35                  40                  45

Gln Lys Val Glu Phe Ser Ile Glu Gln Gly Gln Arg Gly Pro Ala Ala
    50                  55                  60

Ala Asn Val Val Thr Leu
65                  70

```
<210> SEQ ID NO 81
<211> LENGTH: 71
<212> TYPE: PRT
<213> ORGANISM: E. coli

<400> SEQUENCE: 81
```

Met Ser Asn Lys Met Thr Gly Leu Val Lys Trp Phe Asn Ala Asp Lys
 1               5                  10                  15

Gly Phe Gly Phe Ile Ser Pro Val Asp Gly Ser Lys Asp Val Phe Val
            20                  25                  30

His Phe Ser Ala Ile Gln Asn Asp Asn Tyr Arg Thr Leu Phe Glu Gly
        35                  40                  45

Gln Lys Val Thr Phe Ser Ile Glu Ser Gly Ala Lys Gly Pro Ala Ala
    50                  55                  60

Ala Asn Val Ile Ile Thr Asp
65                  70

<210> SEQ ID NO 82
<211> LENGTH: 70
<212> TYPE: PRT
<213> ORGANISM: E. coli

<400> SEQUENCE: 82

Met Ser Gly Lys Met Thr Gly Ile Val Lys Trp Phe Asn Ala Asp Lys
 1               5                  10                  15

Gly Phe Gly Phe Ile Thr Pro Asp Asp Gly Ser Lys Asp Val Phe Val
                20                  25                  30

His Phe Ser Ala Ile Gln Asn Asp Gly Tyr Lys Ser Leu Asp Glu Gly
            35                  40                  45

Gln Lys Val Ser Phe Thr Ile Glu Ser Gly Ala Lys Gly Pro Ala Ala
        50                  55                  60

Gly Asn Val Thr Ser Leu
 65                  70

<210> SEQ ID NO 83
<211> LENGTH: 240
<212> TYPE: DNA
<213> ORGANISM: E. coli

<400> SEQUENCE: 83
ttttctttac aaaagtaatc cttgctatgg gtggttaatc atgcgttaat ggtgttctgg      60
tttgttacaa atttatctga agcagtcatt gttataattt tattatttgt acctcttgag     120
atttccttgt tggtttttct ctctgatatt tttttttcgga ccattctgcc caagggctaa    180
tttcttcaaa agtaataat tatgtctaac aaaatgactg gtttagtgaa atggtttaac     240

<210> SEQ ID NO 84
<211> LENGTH: 251
<212> TYPE: DNA
<213> ORGANISM: E. coli

<400> SEQUENCE: 84
gccggacggc taaaataaaa tttgcttaat ctcaattatc atgcgttaat agctgcgtcg      60
gtttgaaaga cagacagcat acaaagtagt ttactaaagc agttctcatt atcaggcatt     120
atccccttct tttgagtctc tctcctgaac actaagtagt ttctgtatta aagccctgtt     180
tgccgaaagg cccaaaatga aggaagtaaa atatgtctaa taaatgact ggtttagtaa     240 aatggtttaa c                                                          251

<210> SEQ ID NO 85
<211> LENGTH: 255
<212> TYPE: DNA
<213> ORGANISM: E. coli

<400> SEQUENCE: 85
gctggatgtc taaataaac attgcttcat atgttcaact atgcgttaat gattgcgtcg      60
gttgaagaac agacgatata cgaagtagtt tactaaagca gttctcattt cagctgttat     120
tcacttattc cttctttgag tctctccaat taagtacgaa gtcgtttctg ttatgcaaac     180
catttatgcc gaaaggctca agttaaggaa tgtagaatgt caaataaaat gactggttta    240
gtaaaatggt ttaac                                                      255

<210> SEQ ID NO 86
<211> LENGTH: 256
<212> TYPE: DNA

```
<213> ORGANISM: E. coli

<400> SEQUENCE: 86
cataaatatg aaaaataatt gttgcatcac ccgccaatgc gtggcttaat gcacatcaac      60
ggtttgacgt acagaccatt aaagcagtgt agtaaggcaa gtcccttcaa gagttatcgt     120 tgataccct cgtagtgcac attcctttaa cgcttcaaaa tctgtaaagc acgccatatc     180
gccgaaaggc acacttaatt attaaaggta atacactatg tccggtaaaa tgactggtat    240
cgtaaaatgg ttcaac                                                     256

<210> SEQ ID NO 87
<211> LENGTH: 13
<212> TYPE: DNA
<213> ORGANISM: Artificial Sequence
<220> FEATURE:
<223> OTHER INFORMATION: Description of Artificial Sequence: primer

<400> SEQUENCE: 87
ccacaagacc aaa                                                         13
```